(12) United States Patent
Bischoff et al.

(10) Patent No.: US 8,835,482 B2
(45) Date of Patent: Sep. 16, 2014

(54) SUBSTITUTED INDAZOLE AND AZA-INDAZOLE DERIVATIVES AS GAMMA SECRETASE MODULATORS

(75) Inventors: François Paul Bischoff, Vosselaar (BE); Henricus Jacobus Maria Gijsen, Breda (NL); Serge Maria Aloysius Pieters, Hulst (NL); Garrett Berlond Minne, Kalken (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 267 days.

(21) Appl. No.: 13/263,860

(22) PCT Filed: May 5, 2010

(86) PCT No.: PCT/EP2010/056074
§ 371 (c)(1),
(2), (4) Date: Oct. 11, 2011

(87) PCT Pub. No.: WO2010/145883
PCT Pub. Date: Dec. 23, 2010

(65) Prior Publication Data
US 2012/0095036 A1    Apr. 19, 2012

(30) Foreign Application Priority Data
May 7, 2009   (EP) ..................................... 09159615

(51) Int. Cl.
| | | |
|---|---|---|
| A61K 31/4178 | (2006.01) | |
| A61K 31/437 | (2006.01) | |
| C07D 471/04 | (2006.01) | |
| C07D 413/14 | (2006.01) | |
| A61P 25/28 | (2006.01) | |
| C07D 413/12 | (2006.01) | |
| C07D 417/12 | (2006.01) | |
| C07D 403/12 | (2006.01) | |
| C07D 403/14 | (2006.01) | |

(52) U.S. Cl.
CPC ............ *C07D 403/12* (2013.01); *C07D 413/12* (2013.01); *C07D 417/12* (2013.01); *C07D 413/14* (2013.01); *C07D 471/04* (2013.01); *C07D 403/14* (2013.01)
USPC ........... 514/406; 514/338; 514/359; 514/283; 546/119; 548/356.1; 548/358.1

(58) Field of Classification Search
USPC .................. 514/406, 338, 359, 283; 546/119; 548/356.1, 358.1
See application file for complete search history.

(56) References Cited

U.S. PATENT DOCUMENTS

| | | |
|---|---|---|
| 5,767,144 A | 6/1998 | Winn et al. |
| 7,923,563 B2 | 4/2011 | Kushida et al. |
| 2002/0128319 A1 | 9/2002 | Koo et al. |
| 2006/0004013 A1 | 1/2006 | Kimura et al. |
| 2008/0280948 A1 | 11/2008 | Baumann et al. |
| 2009/0062529 A1 | 3/2009 | Kimura et al. |
| 2010/0137320 A1 | 6/2010 | Huanag et al. |

FOREIGN PATENT DOCUMENTS

| | | |
|---|---|---|
| EP | 1757591 A1 | 2/2007 |
| JP | 2003/502313 | 1/2003 |
| WO | 01/78721 A1 | 10/2001 |
| WO | 01/87845 A2 | 11/2001 |
| WO | 2004/017963 A1 | 3/2004 |
| WO | WO 2004/076448 | 9/2004 |
| WO | 2004/110350 A2 | 12/2004 |
| WO | 2005/016892 A1 | 5/2005 |
| WO | 2005/085245 A1 | 9/2005 |
| WO | 2005/115990 A1 | 12/2005 |
| WO | 2006/135667 A1 | 12/2006 |
| WO | WO 2007/034252 | 3/2007 |
| WO | 2007/044895 A2 | 4/2007 |
| WO | WO 2007/038314 | 4/2007 |
| WO | WO 2007/043786 | 4/2007 |
| WO | 2007/105053 A2 | 9/2007 |
| WO | 2007/113276 A1 | 10/2007 |
| WO | 2007/131991 A1 | 11/2007 |
| WO | 2008/065199 A1 | 6/2008 |

(Continued)

OTHER PUBLICATIONS

Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.

(Continued)

*Primary Examiner* — Sreeni Padmanabhan
*Assistant Examiner* — Sahar Javanmard
(74) *Attorney, Agent, or Firm* — Baker & Hostetler LLP

(57) ABSTRACT

The present invention is concerned with novel substituted indazole and aza-indazole derivatives of Formula (I)

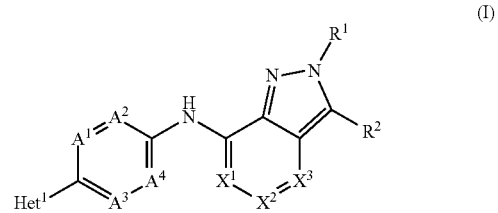

wherein $R^1$, $R^2$, $R^3$, $R^4$, Y, $A^1$, $A^2$, $A^3$, $A^4$, $X^1$, $X^2$, $X^3$ and $Het^1$ have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

10 Claims, No Drawings

(56) References Cited

FOREIGN PATENT DOCUMENTS

| WO | WO 2008/082490 | | 7/2008 |
|---|---|---|---|
| WO | 2008/097538 | A1 | 8/2008 |
| WO | 2008/099210 | A1 | 8/2008 |
| WO | 2008/100412 | A1 | 8/2008 |
| WO | 2008/137139 | A1 | 11/2008 |
| WO | 2008/156580 | A1 | 12/2008 |
| WO | WO 2009/005729 | A1 | 1/2009 |
| WO | WO 2009/032277 | A1 | 3/2009 |
| WO | 2009/050277 | A1 | 4/2009 |
| WO | 2009/073777 | A1 | 6/2009 |
| WO | 2009/076352 | A1 | 6/2009 |
| WO | 2009/103652 | A1 | 8/2009 |
| WO | 2010/010188 | A1 | 1/2010 |
| WO | 2010/137320 | A1 | 2/2010 |
| WO | WO 2010/052199 | | 5/2010 |
| WO | WO 2010/054067 | | 5/2010 |
| WO | 2010/065310 | A1 | 6/2010 |
| WO | 2010/070008 | A1 | 6/2010 |
| WO | 2010/083141 | A1 | 7/2010 |
| WO | 2010/089292 | A1 | 8/2010 |
| WO | 2010/094647 | A1 | 8/2010 |
| WO | 2010/098495 | A1 | 9/2010 |
| WO | 2010/100606 | A1 | 9/2010 |
| WO | WO 2010/098487 | | 9/2010 |
| WO | WO 2010/098488 | | 9/2010 |
| WO | 2010/106745 | A1 | 11/2010 |
| WO | 2010/126745 | A1 | 11/2010 |
| WO | 2010/145883 | A1 | 12/2010 |
| WO | 2011/006903 | A1 | 1/2011 |
| WO | 2011/086098 | A1 | 7/2011 |
| WO | 2011/086099 | A1 | 7/2011 |
| WO | 2012/126984 | A1 | 9/2012 |
| WO | 2012/131539 | A1 | 10/2012 |
| WO | 2013/010904 | A1 | 1/2013 |

OTHER PUBLICATIONS

Larner, a., "Secretases as Therapeutic Targets in Alzheimer's Disease: Patents 2000-2004", Exp. Opinion Ther. Patents 14, p. 1403 (2004).
Marjaux, E., et al. "γ-Secretase Inhibitors: Still in the Running as Alzheimer's Therapeutics", Drug Discovery Today: Therapeutics Strategies 1, p. 1 (2004).
Peretto, D., et al. "Synthesis and Biological Activity of Fluriprofen Analogues as Selective Inhibitors of β-Amylid 1-42 Secretion", J. Med. Chem. 48 p. 5705 (2005).
Schweisguth, F., et al. Regulation of Notch Signaling Activity, Curr. Biol. 14, p. R129 (2004).
Steiner, H., "Uncovering y-Sucretase", Curr. Alzheimer Research 1(3), p. 175 (2004).
Tanzi, R., et al. "Twenty Years of the Alzlheimer's Disease Amyloid Hypothesis: A Genetic Perspective", Cell, vol. 120, (2005) p. 545-555.
Citron, M., et al. "Mutant Presenilins of Alzheimer's Disease Increase Production of 42-Residue Amyloid β-Protein in Both Transfected Cells and Transgenic Mice", Nature Medicine, vol. 3, No. 1, pp. 67-72 (1997).
Dorwald "Side Reactions in Organic Synthesis" 2005, Wiley: VCH Weinheim Preface, pp. 1-15 & Chapter 8, pp. 279-308.
Dyatkin, A., et al., "Determination of the Absolute Configuration of a Key Tricyclic Component of a Novel Vasopressin Receptor Antagonist by Use of Vibrational Circular Dichroism", Chirality, vol. 14, No. 215, pp. 215-219 (2002).
Jadhav, G., et al. "Ammonium metavanadate: A novel catalyst for synthesis of 2-substituted benzimidazole derivatives", Chinese Chemical Letters, vol. 20, (2009), pp. 292-295.
Matthews, D., et al. "A convenient procedure for the preparation of 4(5)-cyanoimidazoles" Journal of Organic Chemistry, vol. 51 (1986), pp. 3228-3231.
Moechars, D., et al., "Early Phenotypic Changes in Transgenic Mice That Overexpress Different Mutants of Amyloid Precursor Protein in Brain", Journal of Biological Chemistry, vol. 274, No. 10, pp. 6483-6492 (1999).
Morihara, T., et al. "Selective Inhibition of Aβ42 Production by NSAID R-Enantiomers", Journal of Neurochemistry, 83, pp. 1009-1012 (2002).
Oumata, N., et al. "Roscovitine-Derived, Dual-Specificity Inhibitors of Cyclin-Dependent Kinases and Casein Kinases 1", Journal of Medicinal Chemistry, vol. 51, pp. 5229-5242 (2008).
Sechi, M., et al., "Design and Synthesis of Novel Indole β-Diketo Acid Derivatives as HIV-1 Integrase Inhibitors", J. Medicinal Chemistry, vol. 42, pp. 5298-5319 (2004).
Vippagunta et al., "Crystalline Solids" Advanced Drug Delivery Reviews 48 (2001) 3-26.
Weggen, S., et al. "A subset of NSAIDs Lower Amyloidegenic Aβ42 Independently of Cyclooxygenase Activity" Letters to Nature vol. 414, *Nov. (2001), pp. 212-216.
West, Anthony R., Solid State Chemistry and its Applications, Wiley, New York, 1988, pp. 358 & 365.
Yu et al. "Physical characterization of, etc." PSTT, vol. 1(3), 118-127 (1998).
Zettl, H., "Exploring the Chemical Space of γ-Secretase Modulators" Trends in Pharmaceutical Sciences, vol. 31, No. 9, pp. 402-210 (2010).
International Search Report re: PCT/EP2010/056074 dated Jun. 16, 2010.
"Crystallization", Kirk-Othmer Encyclopedia of Chemical Technology, 2002, 8, 95-147.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Greene et al., "Protective Groups in Organic Synthesis", John Wiley & Sons, Inc., Third Edition, 1999, 3 pages.
Guillory (Brittain Ed.). "Polymorphism in Pharmaceutical Solids" Marcel Dekker. Inc., NY, 1999, 50 pages.
Jain et al., "Polymorphism in Pharmacy", Indian Drugs, 1986, 23(6), 315-329.
Wang et al., "Preparation of a-Chloroketones by the Chloracetate Claisen Reaction", Synlett, 2000, 6, 902-904.

SUBSTITUTED INDAZOLE AND AZA-INDAZOLE DERIVATIVES AS GAMMA SECRETASE MODULATORS

CROSS-REFERENCE TO RELATED APPLICATIONS

The present application claims the benefits of the filing of Application Nos. EP 09159615.5 filed May 7, 2009, and PCT/EP2010/056074 filed May 5, 2010. The complete disclosures of the aforementioned related patent applications are hereby incorporated herein by reference for all purposes.

FIELD OF THE INVENTION

The present invention is concerned with novel substituted indazole and aza-indazole derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or A$\beta$) peptides of various lengths. A variant thereof, which is the A$\beta$1-42-peptide (Abeta-42), is believed to be the major causative agent for amyloid formation. Another variant is the A$\beta$1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the $\beta$-amyloid precursor protein ($\beta$-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (A$\beta$), specifically A$\beta$42, and have given strong support to the "amyloid cascade hypothesis" of AD (Tanzi and Bertram, 2005, Cell 120, 545). The likely link between A$\beta$ peptide generation and AD pathology emphasizes the need for a better understanding of the mechanisms of A$\beta$ production and strongly warrants a therapeutic approach at modulating A$\beta$ levels.

The release of A$\beta$ peptides is modulated by at least two proteolytic activities referred to as $\beta$- and $\gamma$-secretase cleavage at the N-terminus (Met-Asp bond) and the C-terminus (residues 37-42) of the A$\beta$ peptide, respectively. In the secretory pathway, there is evidence that $\beta$-secretase cleaves first, leading to the secretion of s-APP$\beta$ (s$\beta$) and the retention of a 11 kDa membrane-bound carboxy terminal fragment (CTF). The latter is believed to give rise to A$\beta$ peptides following cleavage by $\gamma$-secretase. The amount of the longer isoform, A$\beta$42, is selectively increased in patients carrying certain mutations in a particular protein (presenilin), and these mutations have been correlated with early-onset familial Alzheimer's disease. Therefore, A$\beta$42 is believed by many researchers to be the main culprit of the pathogenesis of Alzheimer's disease.

It has now become clear that the $\gamma$-secretase activity cannot be ascribed to a single protein, but is in fact associated with an assembly of different proteins.

The gamma ($\gamma$)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the $\gamma$-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on $\gamma$-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2009/032277 relates to heterocyclic compounds useful as gamma secretase modulators.

US 2008/0280948 A1 relates to aminophenyl derivatives which are modulators for amyloid beta.

WO-2009/005729 relates to heterocyclic compounds and their use as gamma secretase modulators.

There is a strong need for novel compounds which modulate $\gamma$-secretase activity thereby opening new avenues for the treatment of Alzheimer's disease. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention are useful as gamma secretase modulators. The compounds according to the invention and the pharmaceutically acceptable compositions thereof, may be useful in the treatment or prevention of Alzheimer's disease.

The present invention concerns novel compounds of Formula (I):

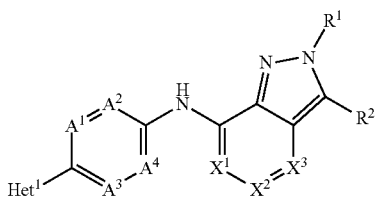

and stereoisomeric forms thereof, wherein $R^1$ is $C_{1-6}$alkyl optionally substituted with one or more substituents each independently selected from the group consisting of halo, $C_{1-4}$alkyloxy, cyclo$C_{3-7}$alkyl, tetrahydropyranyl, tetrahydrofuranyl and phenyl; cyclo$C_{3-7}$alkyl; tetrahydropyranyl; tetrahydrofuranyl; 1,3-benzodioxolyl; or phenyl;

wherein each phenyl independently is optionally substituted with one or more substituents each independently selected from the group consisting of halo, cyano, $C_{1-4}$alkyl optionally substituted with one or more halo substituents, and $C_{1-4}$alkyloxy optionally substituted with one or more halo substituents;

$R^2$ is hydrogen; cyano; or $C_{1-4}$alkyl optionally substituted with one or more substituents each independently selected from the group consisting of $C_{1-4}$alkyloxy, halo and $NR^3R^4$;

$X^1$ is CH or N;

$X^2$ is $CR^5$ or N;

$R^5$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

$X^3$ is $CR^6$ or N;

$R^6$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

wherein each $R^3$ is independently hydrogen; $C_{1-4}$alkyl; or $C_{1-4}$acyl;

wherein each $R^4$ is independently hydrogen; $C_{1-4}$alkyl; or $C_{1-4}$acyl;

provided that no more than two of $X^1$, $X^2$ and $X^3$ are N;

$A^1$ is $CR^7$ or N; wherein $R^7$ is hydrogen, halo or $C_{1-4}$alkyloxy;

$A^2$, $A^3$ and $A^4$ each independently are CH or N; provided that no more than two of $A^1$, $A^2$, $A^3$ and $A^4$ are N;

Het$^1$ is a 5-membered aromatic heterocycle, having formula (a-1), (a-2), (a-3) or (a-4)

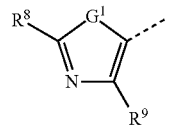

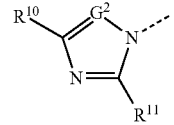

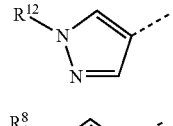

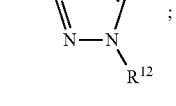

$R^8$ is hydrogen or $C_{1-4}$alkyl;
$R^9$ is hydrogen or $C_{1-4}$alkyl;
$R^{10}$ is hydrogen or $C_{1-4}$alkyl;
$R^{11}$ is hydrogen or $C_{1-4}$alkyl;
$R^{12}$ is $C_{1-4}$alkyl;
$G^1$ is O or S;
$G^2$ is CH or N;

and the pharmaceutically acceptable addition salts, and the solvates thereof.

The present invention also concerns methods for the preparation of compounds of Formula (I) and pharmaceutical compositions comprising them.

The present compounds surprisingly were found to modulate the γ-secretase activity in vitro and in vivo, and therefore may be useful in the treatment or prevention of Alzheimer's disease (AD), traumatic brain injury (TBI), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably AD and other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of Alzheimer's disease, cerebral amyloid angiopathy, multi-infarct dementia, dementia pugilistica or Down syndrome.

The invention also relates to a compound according to the general Formula (I), the stereoisomeric forms thereof and the pharmaceutically acceptable acid or base addition salts and the solvates thereof, for use in the modulation of γ-secretase activity.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" or "halogen" as a group or part of a group is generic for fluoro, chloro, bromo, iodo unless otherwise is indicated.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$acyl" alone or in combination refers to a radical containing from 1 to 4 carbon atoms in which carbonyl is bound to hydrogen or to a straight-chain or branched-chain hydrocarbon having from 1 to 3 carbon atoms. Non-limiting examples of suitable $C_{1-4}$acyl include formyl, acetyl, propionyl, butyryl and iso-butyryl.

The term "$C_{1-4}$alkyloxy" as a group or part of a group refers to a radical having the Formula $-OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The chemical names of the compounds of the present invention were generated according to the nomenclature rules agreed upon by the Chemical Abstracts Service.

In case of tautomeric forms, it should be clear that the non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

The terms described above and others used in the specification are well understood to those in the art.

Preferred features of the compounds of this invention are now set forth. The present invention relates in particular to novel compounds of Formula (I):

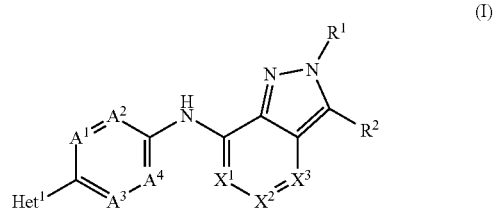

(I)

and stereoisomeric forms thereof, wherein $R^1$ is $C_{1-6}$alkyl optionally substituted with one or more substituents each independently selected from the group consisting of halo, $C_{1-4}$alkyloxy, cyclo$C_{3-7}$alkyl, tetrahydropyranyl, tetrahydrofuranyl and phenyl; cyclo$C_{3-7}$alkyl; tetrahydropyranyl; tetrahydrofuranyl; 1,3-benzodioxolyl; or phenyl;

wherein each phenyl independently is optionally substituted with one or more substituents each independently selected from the group consisting of halo, cyano, $C_{1-4}$alkyl optionally substituted with one or more halo substituents, and $C_{1-4}$alkyloxy optionally substituted with one or more halo substituents;

$R^2$ is hydrogen; cyano; or $C_{1-4}$alkyl optionally substituted with one or more substituents each independently selected from the group consisting of $C_{1-4}$alkyloxy, halo and $NR^3R^4$;

$X^1$ is CH or N;

$X^2$ is $CR^5$ or N;

$R^5$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

$X^3$ is $CR^6$ or N;

$R^6$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

wherein each $R^3$ is independently hydrogen; $C_{1-4}$alkyl; or $C_{1-4}$acyl;

wherein each $R^4$ is independently hydrogen; $C_{1-4}$alkyl; or $C_{1-4}$acyl;

provided that no more than two of $X^1$, $X^2$ and $X^3$ are N;

$A^1$ is $CR^7$ or N; wherein $R^7$ is hydrogen, halo or $C_{1-4}$alkyloxy;

$A^2$, $A^3$ and $A^4$ each independently are CH or N; provided that no more than two of $A^1$, $A^2$, $A^3$ and $A^4$ are N;

$Het^1$ is a 5-membered aromatic heterocycle, having formula (a-1), (a-2), (a-3) or (a-4)

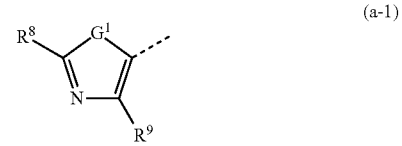

(a-1)

-continued

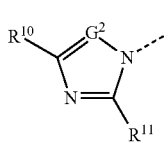
(a-2)

(a-3)

(a-4)

R⁸ is hydrogen or $C_{1-4}$alkyl;
R⁹ is hydrogen or $C_{1-4}$alkyl;
R¹⁶ is hydrogen or $C_{1-4}$alkyl;
R¹¹ is hydrogen or $C_{1-4}$alkyl;
R¹² is $C_{1-4}$alkyl;
G¹ is O or S;
G² is CH or N;
and the pharmaceutically acceptable addition salts, and the solvates thereof.

An embodiment of the present invention relates to those compounds of formula (I)

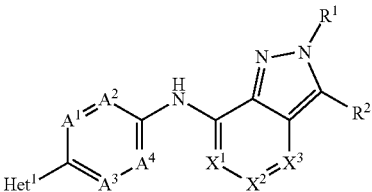
(I)

and stereoisomeric forms thereof, wherein
R¹ is $C_{1-6}$alkyl optionally substituted with one or more substituents selected from the group consisting of halo, $C_{1-4}$alkyloxy, cyclo$C_{3-7}$alkyl, tetrahydropyranyl, tetrahydrofuranyl, and phenyl;
  cyclo$C_{3-7}$alkyl; tetrahydropyranyl; tetrahydrofuranyl; 1,3-benzodioxolyl; or phenyl;
  wherein each phenyl independently is optionally substituted with one or more substituents each independently selected from the group consisting of halo; cyano; $C_{1-4}$alkyl optionally substituted with one or more substituents each independently selected from halo; and $C_{1-4}$alkyloxy optionally substituted with one or more substituents each independently selected from halo;
R² is hydrogen; cyano; $C_{1-4}$alkyl optionally substituted with one or more substituents each independently selected from the group consisting of $C_{1-4}$alkyloxy, halo, and NR³R⁴;
X¹ is CH or N;
X² is CR⁵ or N;
R⁵ is hydrogen; halo; cyano; $C_{1-4}$alkyloxy; or $C_{1-4}$alkyl optionally substituted with one or more substituents each independently selected from the group consisting of halo, $C_{1-4}$alkyloxy, and NR³R⁴;
X³ is CR⁶ or N;
R⁶ is hydrogen; halo; cyano; $C_{1-4}$alkyloxy; or $C_{1-4}$alkyl optionally substituted with one or more substituents each independently selected from the group consisting of halo, $C_{1-4}$alkyloxy, and NR³R⁴;

wherein each R³ is independently H; $C_{1-4}$alkyl; or $C_{1-4}$acyl;
wherein each R⁴ is independently H; $C_{1-4}$alkyl; or $C_{1-4}$acyl;
provided that no more than two of X¹, X² and X³ are N;
A¹ is CR⁷ or N; wherein R⁷ is hydrogen, halo or $C_{1-4}$alkyloxy;
A², A³ and A⁴ each independently are CH or N; provided that no more than two of A¹, A², A³ and A⁴ are N;
Het¹ is a 5-membered aromatic heterocycle, having formula (a-1), (a-2), (a-3) or (a-4)

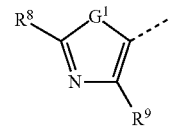
(a-1)

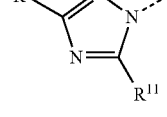
(a-2)

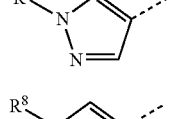
(a-3)

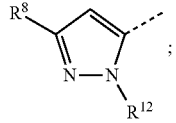
(a-4)

R⁸ is hydrogen or $C_{1-4}$alkyl;
R⁹ is hydrogen or $C_{1-4}$alkyl;
R¹⁰ is hydrogen or $C_{1-4}$alkyl;
R¹¹ is hydrogen or $C_{1-4}$alkyl;
R¹² is $C_{1-4}$alkyl;
G¹ is O or S;
G² is CH or N;
and the pharmaceutically acceptable addition salts, and the solvates thereof.

Another embodiment of the present invention relates to those compounds of formula (I) or any subgroup thereof as mentioned in any of the other embodiments wherein one or more, preferably all, of the following restrictions apply:
(a) R¹ is $C_{1-6}$alkyl optionally substituted with one or more substituents each independently selected from the group consisting of halo, $C_{1-4}$alkyloxy, cyclo$C_{3-7}$alkyl and phenyl;
  cyclo$C_{3-7}$alkyl; tetrahydropyranyl; 1,3-benzodioxolyl; or phenyl;
  wherein each phenyl independently is substituted with one or more substituents each independently selected from the group consisting of halo, $C_{1-4}$alkyl and $C_{1-4}$alkyloxy;
(b) R² is hydrogen; cyano; or $C_{1-4}$alkyl optionally substituted with one or more NH₂ substituents;
(c) X² is CR⁵ or N; in particular X² is CR⁵;
(d) R⁵ is hydrogen; halo; cyano; or $C_{1-4}$alkyl optionally substituted with one or more NH₂ substituents;
(e) X³ is CH or N;
(f) A² is CH or N, and A³ and A⁴ are CH; in particular A², A³ and A⁴ are CH;
(g) Het¹ is a 5-membered aromatic heterocycle, having formula (a-1), (a-2), (a-3) or (a-4); in particular Het¹ is a 5-membered aromatic heterocycle, having formula (a-1), (a-2) or (a-3);

(h) $R^{10}$ is $C_{1-4}$alkyl;
(i) $R^{11}$ is hydrogen;
(j) $R^8$ is hydrogen;
(k) $R^{12}$ is $C_{1-4}$alkyl.

Another embodiment of the present invention relates to those compounds of formula (I) or any subgroup thereof as mentioned in any of the other embodiments wherein one or more, preferably all, of the following restrictions apply:
(a) $R^1$ is $C_{1-4}$alkyl optionally substituted with one or more substituents each independently selected from the group consisting of fluoro, methoxy, cyclopropyl and phenyl; cyclobutyl; tetrahydropyranyl; 1,3-benzodioxolyl; or phenyl;
   wherein each phenyl independently is substituted with one or more substituents each independently selected from the group consisting of methoxy, ethoxy, $C_{1-4}$alkyl and fluoro;
(b) $R^2$ is hydrogen; cyano; methyl optionally substituted with one $NH_2$ substituent;
(c) $X^2$ is $CR^5$ or N; in particular $X^2$ is $CR^5$;
(d) $R^5$ is hydrogen; fluoro; cyano; methyl optionally substituted with one $NH_2$ substituent;
(e) $X^3$ is CH or N;
(f) $R^7$ is hydrogen, fluoro or methoxy;
(g) $A^2$ is CH or N, and $A^3$ and $A^4$ are CH; in particular $A^2$, $A^3$ and $A^4$ are CH;
(h) $Het^1$ is a 5-membered aromatic heterocycle, having formula (a-1), (a-2), (a-3) or (a-4); in particular (a-1), (a-2) or (a-3);
(i) $R^{10}$ is methyl;
(j) $R^{11}$ is hydrogen;
(k) $R^8$ is hydrogen;
(l) $R^{12}$ is methyl.

Another embodiment of the present invention relates to those compounds of formula (I) or any subgroup thereof as mentioned in any of the other embodiments wherein one or more, preferably all, of the following restrictions apply:
(a) $R^1$ is phenyl substituted with one $C_{1-4}$alkyloxy substituent; or $R^1$ is $C_{1-6}$alkyl substituted with one or more halo substituents;
(b) $R^2$ is hydrogen;
(c) $X^1$, $X^2$ and $X^3$ are CH;
(d) $A^1$ is $CR^7$; wherein $R^7$ is $C_{1-4}$alkyloxy;
(e) $A^2$, $A^3$ and $A^4$ are CH;
(f) $Het^1$ has formula (a-1) or (a-2);
(g) $G^1$ is O;
(h) $G^2$ is CH;
(i) $R^8$ is $C_{1-4}$alkyl;
(j) $R^{10}$ is $C_{1-4}$alkyl;
(k) $R^9$ is hydrogen.

Another embodiment of the present invention relates to those compounds of formula (I) or any subgroup thereof as mentioned in any of the other embodiments wherein one or more, preferably all, of the following restrictions apply:
(a) $R^1$ is phenyl substituted with one $C_{1-4}$alkyloxy substituent;
(b) $R^2$ is hydrogen;
(c) $X^1$, $X^2$ and $X^3$ are CH;
(d) $A^1$ is $CR^7$; wherein $R^7$ is $C_{1-4}$alkyloxy;
(e) $A^2$, $A^3$ and $A^4$ are CH;
(f) $Het^1$ has formula (a-2);
(g) $G^2$ is CH;
(h) $R^{10}$ is $C_{1-4}$alkyl;
(i) $R^9$ is hydrogen.

Another embodiment of the present invention relates to those compounds of formula (I) or any subgroup thereof as mentioned in any of the other embodiments wherein one or more, preferably all, of the following restrictions apply:
(a) $R^1$ is $C_{1-6}$alkyl substituted with one or more halo substituents; in particular $R^1$ is $C_{1-6}$alkyl substituted with 3 halo substituents;
(b) $R^2$ is hydrogen;
(c) $X^1$, $X^2$ and $X^3$ are CH;
(d) $A^1$ is $CR^7$; wherein $R^7$ is $C_{1-4}$alkyloxy;
(e) $A^2$, $A^3$ and $A^4$ are CH;
(f) $Het^1$ has formula (a-1);
(g) $G^1$ is O;
(h) $R^8$ is $C_{1-4}$alkyl;
(i) $R^9$ is hydrogen.

In a further embodiment, the invention relates to compounds according to any of the other embodiments, wherein $R^1$ is phenyl substituted with one or more substituents each independently selected from the group consisting of $C_{1-4}$alkyl optionally substituted with one or more halo substituents, and $C_{1-4}$alkyloxy optionally substituted with one or more halo substituents.

In a further embodiment, the invention relates to compounds according to any of the other embodiments, wherein $R^1$ is phenyl substituted with one or more substituents each independently selected from the group consisting of $C_{1-4}$alkyl and $C_{1-4}$alkyloxy.

In a further embodiment, the invention relates to compounds according to any of the other embodiments, wherein $R^1$ is $C_{1-6}$alkyl optionally substituted with one or more halo substituents.

In a further embodiment, the invention relates to compounds according to any of the other embodiments, wherein $R^1$ is $C_{1-6}$alkyl optionally substituted with one or more fluoro substituents.

In a further embodiment, the invention relates to compounds according to any of the other embodiments, wherein $R^1$ is 2,2,2-trifluoroethyl.

In a further embodiment, the invention relates to compounds according to any of the other embodiments, wherein $X^1$ is CH.

In a further embodiment, the invention relates to compounds according to any of the other embodiments, wherein $X^1$ is N.

In a further embodiment, the invention relates to compounds according to any of the other embodiments, wherein $X^2$ is CH.

In a further embodiment, the invention relates to compounds according to any of the other embodiments, wherein $X^2$ is N.

In a further embodiment, the invention relates to compounds according to any of the other embodiments, wherein $X^3$ is N.

In a further embodiment, the invention relates to compounds according to any of the other embodiments, wherein $X^3$ is $CR^6$.

In a further embodiment, the invention relates to compounds according to any of the other embodiments, wherein $R^6$ is hydrogen.

In a further embodiment, the invention relates to compounds according to any of the other embodiments, wherein $A^1$ is $CR^7$.

In a further embodiment, the invention relates to compounds according to any of the other embodiments, wherein $A^1$ is N.

In a further embodiment, the invention relates to compounds according to any of the other embodiments, wherein $A^2$, $A^3$ and $A^4$ each independently are CH.

In a further embodiment, the invention relates to compounds according to any of the other embodiments, wherein Het¹ has formula (a-3).

In a further embodiment, the invention relates to compounds according to any of the other embodiments, wherein Het¹ has formula (a-4).

In a further embodiment, the invention relates to compounds according to any of the other embodiments, wherein G¹ is S.

In a further embodiment, the invention relates to compounds according to any of the other embodiments, wherein G² is N.

Another embodiment of the present invention relates to those compounds of formula (I) or any subgroup thereof as mentioned in any of the other embodiments, wherein 1,3-benzodioxolyl is restricted to 1,3-benzodioxol-5-yl.

In an embodiment the compound of Formula (I) is selected from the group comprising:

N-[3-methoxy-4-(4-methyl-1H-imidazol-1-yl)phenyl]-2-(3-methoxyphenyl)-2H-indazol-7-amine,
2-[(4-fluorophenyl)methyl]-N-[3-methoxy-4-(4-methyl-1H-imidazol-1-yl)phenyl]-2H-indazol-7-amine,
N-[3-methoxy-4-(4-methyl-1H-imidazol-1-yl)phenyl]-2-(3-methoxyphenyl)-3-methyl-2H-indazol-7-amine,
N-[3-methoxy-4-(3-methyl-1H-1,2,4-triazol-1-yl)phenyl]-2-(3-methoxyphenyl)-2H-indazol-7-amine,
2-butyl-N-[3-methoxy-4-(4-methyl-1H-imidazol-1-yl)phenyl]-2H-indazol-7-amine,
2-butyl-N-[3-methoxy-4-(4-methyl-1H-imidazol-1-yl)phenyl]-2H-indazol-7-amine .2HCl,
2-butyl-N-[3-methoxy-4-(4-methyl-1H-imidazol-1-yl)phenyl]-3-methyl-2H-indazol-7-amine,
2-butyl-N-[3-methoxy-4-(4-methyl-1H-imidazol-1-yl)phenyl]-3-methyl-2H-indazol-7-amine .2HCl,
2-(4-fluorophenyl)-N-[3-methoxy-4-(2-methyl-5-oxazolyl)phenyl]-3-methyl-2H-indazol-7-amine,
2-(3-methoxyphenyl)-3-methyl-N-[6-(4-methyl-5-oxazolyl)-3-pyridinyl]-2H-indazol-7-amine,
2-(4-fluorophenyl)-3-methyl-N-[6-(4-methyl-5-oxazolyl)-3-pyridinyl]-2H-indazol-7-amine,
N-[3-fluoro-4-(3-methyl-1H-1,2,4-triazol-1-yl)phenyl]-3-methyl-2-(4,4,4-trifluorobutyl)-2H-indazol-7-amine,
N-[3-methoxy-4-(4-methyl-1H-imidazol-1-yl)phenyl]-2-methyl-2H-indazol-7-amine,
2-(4-fluorophenyl)-3-methyl-N-[4-(2-methyl-5-oxazolyl)phenyl]-2H-indazol-7-amine,
2-(4-fluorophenyl)-3-methyl-N-[4-(2-methyl-5-oxazolyl)phenyl]-2H-indazol-7-amine .1.5HCl,
2-(3-methoxyphenyl)-3-methyl-N-[4-(2-methyl-5-oxazolyl)phenyl]-2H-indazol-7-amine,
2-(2,4-difluorophenyl)-N-[3-methoxy-4-(4-methyl-1H-imidazol-1-yl)phenyl]-3-methyl-2H-indazol-7-amine,
2-(2,4-difluorophenyl)-3-methyl-N-[4-(2-methyl-5-oxazolyl)phenyl]-2H-indazol-7-amine,
2-[4-ethoxy-2-methyl-5-(1-methylethyl)phenyl]-3-methyl-N-[4-(2-methyl-5-oxazolyl)phenyl]-2H-indazol-7-amine,
2-(2,4-difluorophenyl)-N-[3-fluoro-4-(3-methyl-1H-1,2,4-triazol-1-yl)phenyl]-3-methyl-2H-indazol-7-amine,
2-[4-ethoxy-2-methyl-5-(1-methylethyl)phenyl]-N-[3-methoxy-4-(4-methyl-1H-imidazol-1-yl)phenyl]-3-methyl-2H-indazol-7-amine,
2-[4-ethoxy-2-methyl-5-(1-methylethyl)phenyl]-N-[3-methoxy-4-(3-methyl-1H-1,2,4-triazol-1-yl)phenyl]-3-methyl-2H-indazol-7-amine,
2-(2,4-difluorophenyl)-N-[3-methoxy-4-(2-methyl-5-thiazolyl)phenyl]-3-methyl-2H-indazol-7-amine,
N-[3-methoxy-4-(4-methyl-5-oxazolyl)phenyl]-2-(3-methoxyphenyl)-3-methyl-2H-indazol-7-amine,
N-[3-methoxy-4-(4-methyl-5-oxazolyl)phenyl]-2-(3-methoxyphenyl)-3-methyl-2H-indazol-7-amine .1.9HCl,
N-[3-methoxy-4-(3-methyl-1H-1,2,4-triazol-1-yl)phenyl]-2-(3-methoxyphenyl)-3-methyl-2H-indazol-7-amine,
N-[3-methoxy-4-(3-methyl-1H-1,2,4-triazol-1-yl)phenyl]-2-(3-methoxyphenyl)-3-methyl-2H-indazol-7-amine. 1.9HCl,
N-[3-methoxy-4-(3-methyl-1H-1,2,4-triazol-1-yl)phenyl]-2-methyl-2H-indazol-7-amine,
2-methyl-N-[4-(2-methyl-5-oxazolyl)phenyl]-2H-indazol-7-amine,
N-[3-methoxy-4-(2-methyl-5-oxazolyl)phenyl]-2-(3-methoxyphenyl)-3-methyl-2H-pyrazolo[3,4-c]pyridin-7-amine,
2-(cyclopropylmethyl)-N-[3-methoxy-4-(4-methyl-1H-imidazol-1-yl)phenyl]-2H-indazol-7-amine,
2-(cyclopropylmethyl)-N-[3-methoxy-4-(4-methyl-1H-imidazol-1-yl)phenyl]-2H-indazol-7-amine .2HCl,
N-[3-methoxy-4-(2-methyl-5-oxazolyl)phenyl]-2-(2,2,2-trifluoroethyl)-2H-indazol-7-amine,
N-[4-[2-(1-methylethyl)-5-oxazolyl]phenyl]-2-(2,2,2-trifluoroethyl)-2H-indazol-7-amine,
N-[3-methoxy-4-(2-methyl-5-thiazolyl)phenyl]-2-methyl-2H-indazol-7-amine,
2-butyl-7-[[3-methoxy-4-(4-methyl-1H-imidazol-1-yl)phenyl]amino]-2H-indazole-5-carbonitrile,
2-butyl-7-[[3-methoxy-4-(4-methyl-1H-imidazol-1-yl)phenyl]amino]-2H-indazole-5-carbonitrile .2HCl,
2-cyclobutyl-N-[4-(2-methyl-5-oxazolyl)phenyl]-2H-indazol-7-amine,
2-cyclobutyl-N-[4-(2-methyl-5-oxazolyl)phenyl]-2H-indazol-7-amine .1.2HCl,
2-(4-fluorophenyl)-7-[[4-(2-methyl-5-oxazolyl)phenyl]amino]-2H-indazole-3-carbonitrile,
2-(2-methoxyethyl)-N-[4-(2-methyl-5-oxazolyl)phenyl]-2H-indazol-7-amine,
2-(2-methoxyethyl)-N-[4-(2-methyl-5-oxazolyl)phenyl]-2H-indazol-7-amine .1.5HCl .1.25H₂O,
2-(2-methoxyethyl)-N-[3-methoxy-4-(4-methyl-5-oxazolyl)phenyl]-2H-indazol-7-amine,
2-(2-methoxyethyl)-N-[3-methoxy-4-(4-methyl-5-oxazolyl)phenyl]-2H-indazol-7-amine .1.5HCl .0.18H₂O,
2-(cyclopropylmethyl)-N-[4-(2-methyl-5-oxazolyl)phenyl]-2H-indazol-7-amine,
2-(cyclopropylmethyl)-N-[4-(2-methyl-5-oxazolyl)phenyl]-2H-indazol-7-amine .2HCl,
2-(1,3-benzodioxol-5-yl)-N-[4-(2-methyl-5-oxazolyl)phenyl]-2H-indazol-7-amine,
2-(cyclopropylmethyl)-N-[3-methoxy-4-(4-methyl-5-oxazolyl)phenyl]-2H-indazol-7-amine,
2-(cyclopropylmethyl)-N-[3-methoxy-4-(4-methyl-5-oxazolyl)phenyl]-2H-indazol-7-amine .2HCl,
2-(3-methoxyphenyl)-3-methyl-N-[4-(2-methyl-5-oxazolyl)phenyl]-2H-pyrazolo[3,4-c]pyridin-7-amine,
N-[3-fluoro-4-(1-methyl-1H-pyrazol-4-yl)phenyl]-2-(3-methoxyphenyl)-3-methyl-2H-indazol-7-amine,
2-(cyclopropylmethyl)-N-[3-methoxy-4-(2-methyl-5-oxazolyl)phenyl]-2H-indazol-7-amine,
2-(cyclopropylmethyl)-N-[3-methoxy-4-(2-methyl-5-oxazolyl)phenyl]-2H-indazol-7-amine HCl,
2-(4-fluorophenyl)-7-[[4-(2-methyl-5-oxazolyl)phenyl]amino]-2H-indazole-3-methanamine,
2-butyl-7-[[3-methoxy-4-(4-methyl-1H-imidazol-1-yl)phenyl]amino]-2H-indazole-5-methanamine, 2-butyl-7-[[3-methoxy-4-(4-methyl-1H-imidazol-1-yl)phenyl]amino]-2H-indazole-5-methanamine .4HCl,
2-(cyclopropylmethyl)-N-[6-(2-methyl-5-oxazolyl)-3-pyridinyl]-2H-indazol-7-amine,
2-(cyclopropylmethyl)-N-[6-(2-methyl-5-oxazolyl)-3-pyridinyl]-2H-indazol-7-amine .2HCl,
N-[4-(2-methyl-5-oxazolyl)phenyl]-2-(tetrahydro-2H-pyran-4-yl)-2H-indazol-7-amine,
N-[6-(2-methyl-5-oxazolyl)-3-pyridinyl]-2-(2,2,2-trifluoroethyl)-2H-indazol-7-amine,
N-[3-methoxy-4-(3-methyl-1H-1,2,4-triazol-1-yl)phenyl]-2-(2,2,2-trifluoroethyl)-2H-indazol-7-amine,
N-[3-methoxy-4-(2-methyl-5-oxazolyl)phenyl]-5-methyl-2-(2,2,2-trifluoroethyl)-2H-pyrazolo[3,4-c]pyridin-7-amine,
N-[3-methoxy-4-(3-methyl-1H-1,2,4-triazol-1-yl)phenyl]-5-methyl-2-(2,2,2-trifluoroethyl)-2H-pyrazolo[3,4-c]pyridin-7-amine,
2-(5-methoxy-2-methylphenyl)-3-methyl-N-[6-(2-methyl-5-oxazolyl)-3-pyridinyl]-2H-indazol-7-amine,
5-fluoro-2-(4-fluorophenyl)-3-methyl-N-[6-(2-methyl-5-oxazolyl)-3-pyridinyl]-2H-indazol-7-amine,
N-[3-methoxy-4-(2-methyl-5-oxazolyl)phenyl]-5-methyl-2-(2,2,2-trifluoroethyl)-2H-pyrazolo[4,3-b]pyridin-7-amine,
N-[3-fluoro-4-(4-methyl-1H-imidazol-1-yl)phenyl]-2-(2,2,2-trifluoroethyl)-2H-indazol-7-amine,
2-(3-methoxyphenyl)-3-methyl-N-[4-(1-methyl-1H-pyrazol-5-yl)phenyl]-2H-indazol-7-amine,
2-(3-methoxyphenyl)-3-methyl-N-[4-(1-methyl-1H-pyrazol-5-yl)phenyl]-2H-indazol-7-amine .2HCl .0.5H$_2$O,
N-[6-methoxy-5-(4-methyl-1H-imidazol-1-yl)-2-pyridinyl]-2-(2,2,2-trifluoroethyl)-2H-indazol-7-amine,
N-[3-fluoro-4-(4-methyl-1H-imidazol-1-yl)phenyl]-2-(2,2,2-trifluoroethyl)-2H-pyrazolo[4,3-c]pyridin-7-amine,
N-[3-methoxy-4-(3-methyl-1H-1,2,4-triazol-1-yl)phenyl]-5-(1-methylethyl)-2-(2,2,2-trifluoroethyl)-2H-pyrazolo[4,3-b]pyridin-7-amine,
N-[6-methoxy-5-(4-methyl-1H-imidazol-1-yl)-2-pyridinyl]-5-(1-methylethyl)-2-(2,2,2-trifluoroethyl)-2H-pyrazolo[4,3-b]pyridin-7-amine,
including any stereochemically isomeric form thereof, and the pharmaceutically acceptable addition salts and the solvates thereof.

In an embodiment the compound of Formula (I) is selected from the group comprising N-[3-methoxy-4-(2-methyl-5-oxazolyl)phenyl]-2-(2,2,2-trifluoroethyl)-2H-indazol-7-amine, and N-[3-methoxy-4-(4-methyl-1H-imidazol-1-yl)phenyl]-2-(3-methoxyphenyl)-3-methyl-2H-indazol-7-amine,
including any stereochemically isomeric form thereof, and the pharmaceutically acceptable addition salts and the solvates thereof.

All possible combinations of the above-indicated interesting embodiments are considered to be embraced within the scope of this invention.

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below. All variables are defined as mentioned hereabove unless otherwise is indicated. L is defined as a leaving group such as, for example, Cl, Br, I, tosylate, mesylate or triflate, in particular Cl, Br or I, unless otherwise is indicated.

Experimental Procedure 1

In general, compounds of formula (I), can be prepared as set out below in Scheme 1 wherein all variables are defined as hereabove:

Scheme 1

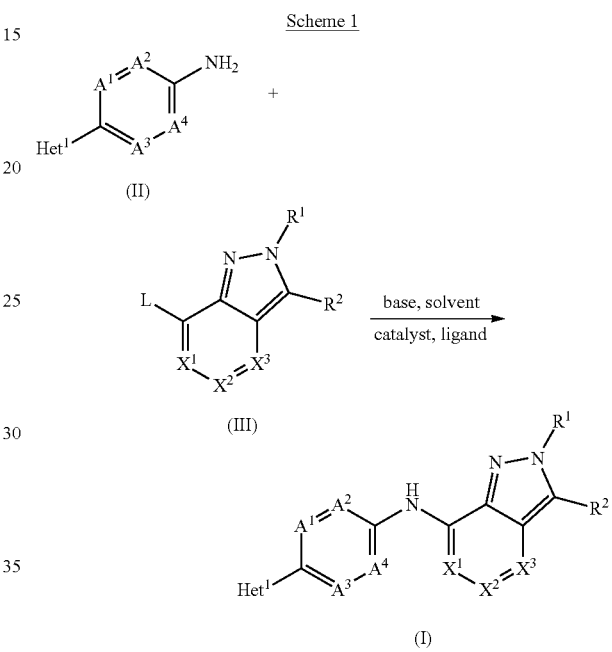

Compounds of formula (I) can be prepared via a coupling reaction between intermediates of formula (II) and (III), as shown in Scheme 1, wherein all variables are as defined hereinbefore. This reaction may be performed in the presence of a suitable base such as, for example, Cs$_2$CO$_3$ or sodium tert-butoxide. The reaction can be performed in a reaction-inert solvent such as, for example, toluene, N,N-dimethylformamide (DMF), tert-butanol or dioxane. The reaction typically is performed in the presence of a catalyst system comprising a suitable catalyst such as palladium(II) acetate (Pd(OAc)$_2$) or tris(dibenzylideneacetone)dipalladium (Pd$_2$(dba)$_3$) and a ligand such as (9,9-dimethyl-9H-xanthene-4,5-diyl)bis[diphenylphosphine] (Xantphos), [1,1'-binaphthalene]-2,2'-diylbis[diphenylphosphine] (BINAP), or dicyclohexyl[2',4',6'-tris(1-methylethyl)[1,1'-biphenyl]-2-yl]-phosphine (X-Phos). Preferably this reaction is carried out under an inert atmosphere, such as a N$_2$ or an Ar atmosphere. Reaction rate and yield may be enhanced by microwave assisted heating.

Experimental Procedure 2

An intermediate of formula (III) wherein R$^2$ is restricted to C$_{1-4}$alkyl, hereby named intermediate of formula (IV), can be prepared by an alkylation reaction of an intermediate of formula (V) according to conventional reaction procedures generally known in the art. The alkylation reaction is performed in the presence of a suitable base such as, for example, lithium diisopropylamide or lithium bis(trimethylsilyl)amide, and an alkylating reagent such as, for example, C$_{1-4}$alkyl-Y wherein Y is a reacting group such as, for example, Cl, Br or I. All other variables are as defined before. The reaction can be performed in an aprotic solvent such as, for example, DMF or tetrahydrofuran (THF).

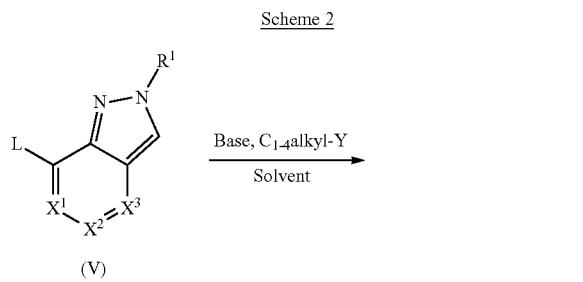

Experimental Procedure 3

An intermediate of formula (III) wherein $R^2$ is restricted to —$CH_2NH_2$, hereby named intermediate of formula (VI), can be prepared by the reduction of an intermediate of formula (VII) according to conventional reaction procedures generally known in the art. This reduction is performed in the presence of a suitable reducing agent such as, for example, Raney Nickel. The reaction can be performed in a protic solvent such as, for example, methanol (MeOH) in the presence of ammonia.

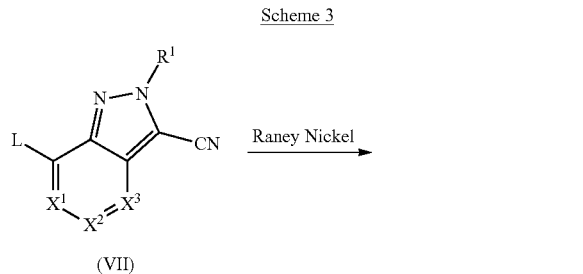

The $NH_2$ group in the intermediate of formula (VI) can be further alkylated and/or acylated to provide further intermediates of formula (III).

Experimental Procedure 4

An intermediate of formula (V) can be prepared by the reduction of an intermediate of formula (VIII) according to conventional reaction procedures generally known in the art. This reduction can be performed in the presence of a suitable reducing agent such as, for example, $SnCl_2.2H_2O$. The reaction can be performed in a protic solvent such as, for example, ethanol (EtOH) at an elevated temperature, typically between 40 and 50° C.

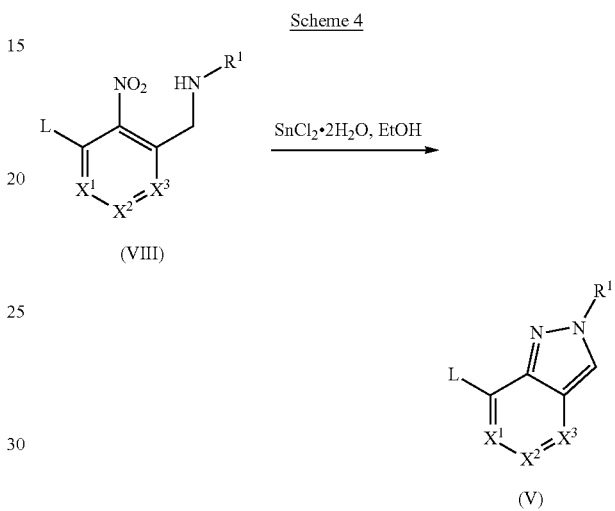

In the particular case of an intermediate of formula (V) wherein $X^1$ is defined as N and $X^2$ and $X^3$ are defined as CH, hereby named an intermediate of formula (V-a), a hydrolysis or ethanolysis reaction can be performed to replace group 'L' by —OH or ethoxy. The intermediate thus obtained can be converted back again to an intermediate of formula (V-a) according to conventional reaction procedures generally known in the art.

Experimental Procedure 5

An intermediate of formula (VIII) can be prepared, according to Scheme 5, by the reductive amination of an intermediate of formula (IX). This reaction is performed in the presence of a suitable reducing agent such as, for example, sodium triacetoxyborohydride ($NaBH(OAc)_3$) and a primary amine such as, for example, $R^1$—$NH_2$. The reaction can be performed in an aprotic solvent such as, for example, 1,2-dichloroethane.

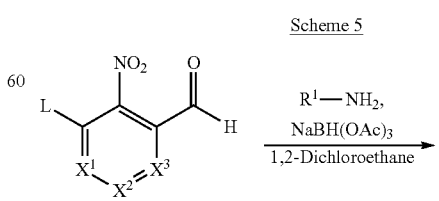

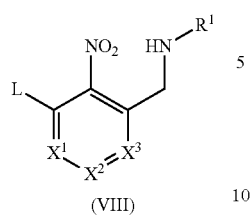

(VIII)

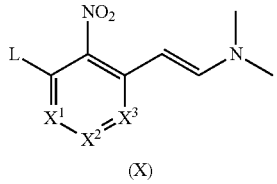

(X)

Experimental Procedure 6

An intermediate of formula (IX) can be prepared by the oxidation of an intermediate of formula (X) as depicted in Scheme 6. This reaction is performed in the presence of, a suitable oxidizing agent such as, for example, sodium periodate ($NaIO_4$). The reaction can be performed in a mixture of solvents such as, for example, water/DMF or water/THF.

Experimental Procedure 8

Alternatively, an intermediate of formula (IX) can also be prepared, according to Scheme 8, by the oxidation of an intermediate of formula (XII) which may be commercially available or may be prepared according to conventional reaction procedures generally known in the art. This reaction is performed in the presence of a suitable oxidizing agent such as, for example, manganese dioxide ($MnO_2$) or pyridinium chlorochromate (PCC). The reaction can be performed in a solvent such as, for example, dichloromethane (DCM) or chloroform ($CHCl_3$), typically dried in the presence of molecular sieves.

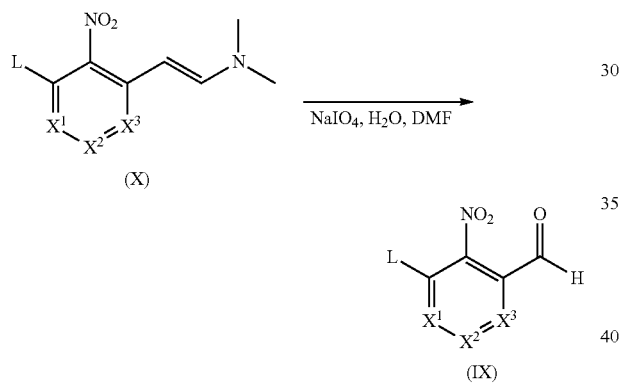

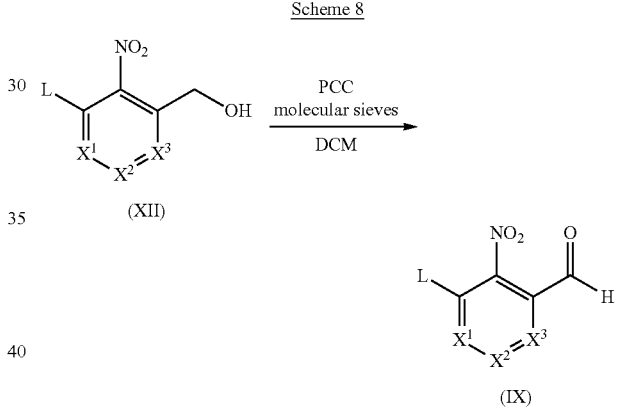

Experimental Procedure 7

An intermediate of formula (X) can be prepared by the condensation of dimethylformamide dimethyl acetal (DMF-DMA) with an intermediate of formula (XI) as depicted in Scheme 7. Intermediate (XI) may be commercially available or may be prepared according to conventional reaction procedures generally known in the art. Stirring and/or elevated temperatures (for example between 70-110° C.) may enhance the rate of the reaction.

Experimental Procedure 9

Alternatively an intermediate of formula (V) can be prepared by the alkylation of an intermediate of formula (XIII) according to conventional reaction procedures generally known in the art. This alkylation typically can be performed in the absence or the presence of a suitable base, such as, for example, cesium carbonate or a tertiary amine such as, for example, N,N-dicyclohexyl-N-methylamine, and an alkylating reagent such as, for example, $R^1$—Y (wherein Y is defined as Cl, Br or I), $R^1$—O—$SO_2$—R (wherein R can be selected from a variety of groups well known to those skilled in the art; typical but non-limiting examples for R are $C_{1-6}$alkyl, perfluoro$C_{1-6}$alkyl or optionally substituted phenyl; more specific examples for R are methyl or p-methylphenyl), or $R^1$—O—$SO_2$—O—$R^1$. These alkylating agents may be commercially available or may be prepared according to conventional reaction procedures generally know in the art. The reaction can be performed in a reaction-inert solvent such as, for example, toluene or DMF. Stirring, elevated temperatures (for example between 70-110° C.) may enhance the rate of the reaction.

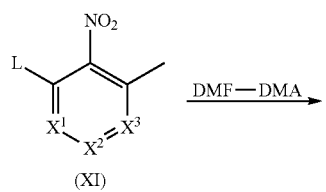

Scheme 9

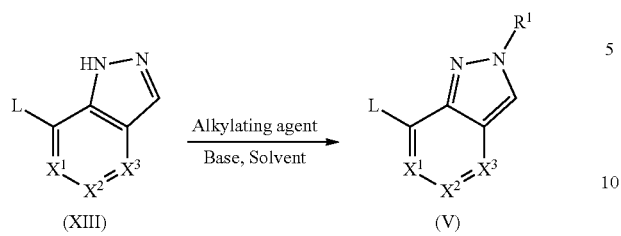

Experimental Procedure 10

An intermediate of formula (XIII) can be prepared by the deprotonation of an intermediate of formula (XIV) according to conventional reaction procedures generally known in the art. This reaction typically is performed in the presence of a suitable base, such as, for example, potassium tert-butoxide (KOtBu), in a solvent such as, for example, dimethylsulfoxide (DMSO).

Scheme 10

Experimental Procedure 11

An intermediate of formula (XIV) can be prepared by the diazotization of an intermediate of formula (XV) according to conventional reaction procedures generally known in the art. This reaction typically can be performed in an aqueous acid solution, such as, for example, a hydrochloric acid solution in the presence of sodium nitrite (NaNO$_2$). The reaction is typically performed at low temperatures (<5° C.). The diazonium species is then quenched, at low temperatures (<5° C.) with tert-butyl mercaptan (t-BuSH) in a protic solvent such as, for example, EtOH.

Scheme 11

Experimental Procedure 12

Alternatively an intermediate of formula (XIII) can be prepared, in one step, by the diazotization of an intermediate of formula (XV) according to conventional reaction procedures generally known in the art. This reaction typically can be performed in an acidic solution such as, for example, glacial acetic acid in the presence of an aqueous solution of sodium nitrite (NaNO$_2$).

Scheme 12

The synthesis of an intermediate of formula (XIII) wherein $X^2$ represents N, hereby named an intermediate of formula (XIII-a), requires preliminary protection of the amino function of an intermediate of formula (XV) wherein $X^2$ is N, as described in WO 2005/016892.

Experimental Procedure 13

An intermediate of formula (VII) can be prepared by the reduction of an intermediate of formula (XVI) according to conventional reaction procedures generally known in the art. This reduction typically can be performed in the presence of a suitable reducing agent such as, for example, phosphorus trichloride (PCl$_3$) or triphenylphosphine. The reaction typically can be performed in a reaction-inert solvent such as, for example, CHCl$_3$ at an elevated temperature (between 50 and 75° C.).

Scheme 13

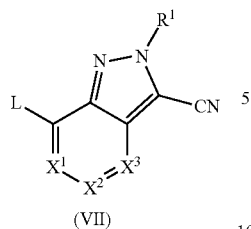

(VII)

Experimental Procedure 14

An intermediate of formula (XVI) can be prepared by the formation of the Schiff base between an intermediate of formula (IX) and a primary amine $R^1$—$NH_2$ according to conventional reaction procedures generally known in the art. Treatment with sodium cyanide or trimethylsilyl cyanide converts the Schiff base to its α-aminonitrile derivative which in turn undergoes basic cyclisation. The cyclisation step is performed in the presence of a suitable base such as, for instance, an aqueous solution of sodium carbonate.

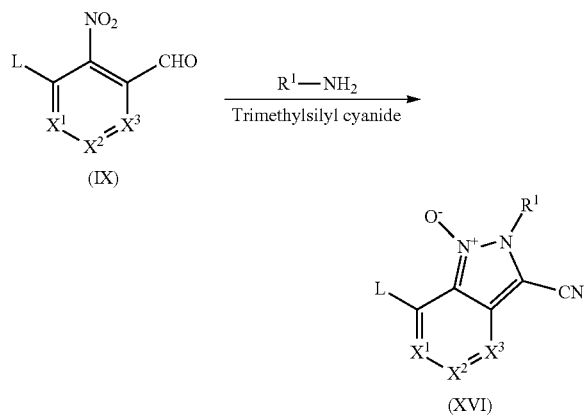

Scheme 14

Experimental Procedure 15

An intermediate of formula (II) can be prepared by the reduction of an intermediate of formula (XVII) as is shown in Scheme 15, wherein all variables are as defined before.

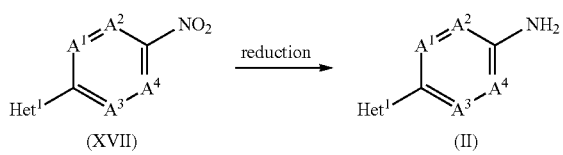

Scheme 15

The reduction of (XVII) to (II) can be conducted by conventional methods such as, for example, a reductive hydrogenation or reduction with a metal or a metal salt and an acid [for example a metal such as iron or a metal salt such as $SnCl_2$ and an acid such as an inorganic acid (hydrochloric acid, sulfuric acid or the like) or an organic acid (acetic acid or the like)], or other well-known methods for converting a nitro-group to the corresponding amine

Experimental Procedure 16

An intermediate of formula (XVII), wherein $Het^1$ is restricted to (a-2) as shown in Scheme 16, hereby named an intermediate of formula (XVIII) can be prepared via a nucleophilic aromatic substitution of an intermediate (XIX) with an optionally substituted imidazole or triazole of formula (XX) according to Scheme 16, wherein $L^a$ is defined as F, Cl, or Br and wherein all other variables are defined as mentioned hereabove. The reaction may be performed under a protecting atmosphere such as, for example, $N_2$ atmosphere. Stirring, elevated temperatures (for example between 70-170° C.) and/or pressure may enhance the rate of the reaction. The reaction typically may be performed in an organic solvent such as, for example, DMSO, DMF or N-methylpyrrolidinone (NMP) in the presence of a base such as, for example, $K_2CO_3$, $Cs_2CO_3$, or $Et_3N$.

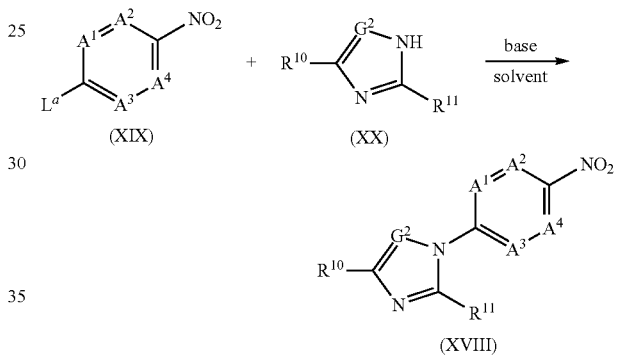

Scheme 16

Intermediates of formula (XIX) and formula (XX) are commercially available or can be easily prepared by those skilled in the art.

Experimental Procedure 17

An intermediate of formula (XVII) wherein $Het^1$ is restricted to an oxazole substituted with $R^{8a}$ ($C_{1-4}$alkyl) in the 2-position as shown in Scheme 17, hereby named an intermediate of formula (XXI), can be prepared by condensation of an intermediate of formula (XXII) with an intermediate of formula (XXIII) which can be activated with iodobenzene diacetate in the presence of trifluoromethanesulfonic acid. Stirring and/or elevated temperatures (for example between 70-100° C.) may enhance the rate of reaction. In Scheme 17, $R^{8a}$ is defined as $C_{1-4}$ alkyl and all other variables are defined as hereinbefore.

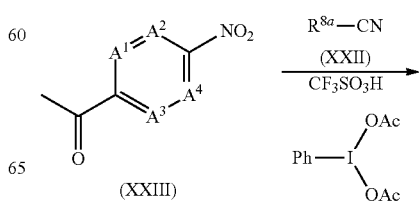

Scheme 17

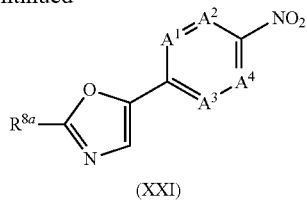

(XXI)

Experimental Procedure 18

An intermediate of formula (XXVII) wherein Het¹ is restricted to oxazole substituted with $R^9$ in the 4-position, hereby named intermediate of formula (XXIV), can be prepared by a condensation reaction of an intermediate of formula (XXV) with an intermediate of formula (XXVI) as is illustrated in Scheme 18. Intermediate (XXVI) may be commercially available or may be prepared according to conventional reaction procedures generally know in the art. This condensation reaction typically can be performed in the presence of a suitable base such as, for example, $K_2CO_3$ or sodium ethoxide (NaOEt). The reaction can be performed in a protic solvent such as, for example, MeOH or EtOH. Stirring and/or elevated temperatures (for example between 70-110° C.) may enhance the rate of the reaction. In Scheme 18, all variables are defined as mentioned here above.

Scheme 18

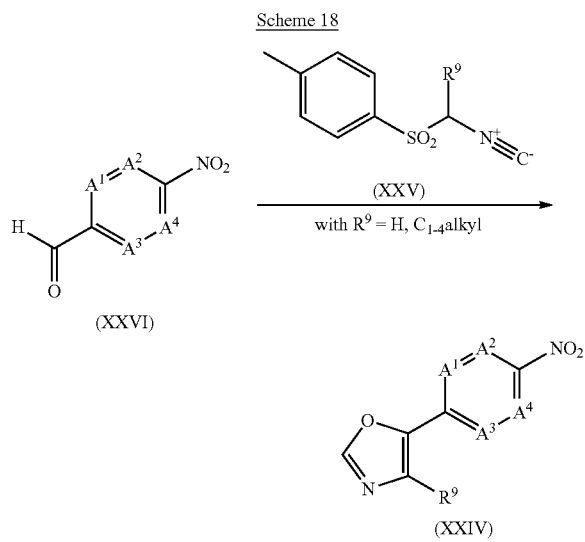

Alternatively, the reaction described in Scheme 18 may also be performed with a benzaldehyde derivative of the intermediate of formula (XXVI) wherein $NO_2$ is replaced by Cl, Br or I.

Experimental Procedure 19

An intermediate of formula (II) can also be prepared according to well-known reaction procedures, by conversion of the L-substituent in an intermediate of formula (XXVII), into an amino-group or a masked or protected amino functionality, which can subsequently be converted into an amino-group, according to Scheme 19. In Scheme 19, $L^x$ is defined as Cl, Br or I, and all other variables are defined as mentioned here above.

Scheme 19

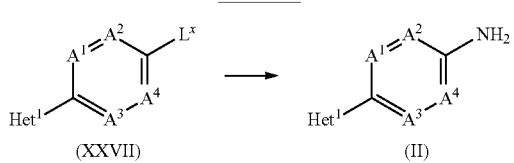

Experimental Procedure 20

Compounds of formula (XVII), can also be prepared via a coupling reaction between an intermediate of formula (XXVIII) and an intermediate of formula (XXIX) according to Scheme 20 wherein $L^y$ is defined as Cl, Br or I and wherein all other variables are as defined before.

Scheme 20

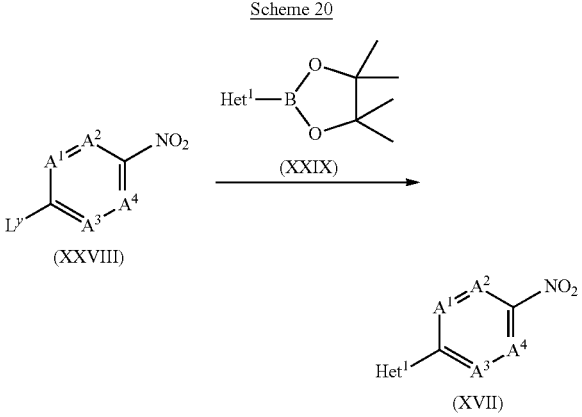

In Scheme 20, an intermediate of formula (XXIX) may be commercially available or may be prepared according to conventional reaction procedures generally known in the art. The coupling reaction typically can be performed in the presence of a suitable base such as, for example, $Cs_2CO_3$, $Na_2CO_3$ or CsF. The reaction can be performed in a reaction-inert solvent such as, for example, toluene, DMF or dioxane. The reaction typically can be performed in the presence of a catalyst such as tetrakis(triphenyl-phosphine) palladium ($Pd(PPh_3)_4$) or 1,1-bis (diphenylphosphinoferrocenedichloro-palladiumII) ($Pd(dppf)Cl_2$). Stirring, elevated temperatures (for example between 70-140° C.) and/or pressure may enhance the rate of the reaction. Preferably this reaction is carried out under an inert atmosphere, such as a nitrogen or argon atmosphere.

Alternatively, the boronic acid picanol ester derivative of formula (XXIX) can be replaced by the corresponding boronic acid derivative.

Experimental Procedure 21

An intermediate of formula (XVII), wherein Het¹ is restricted as shown in Scheme 21, hereby named intermediate of formula (XXX), can be prepared via a coupling reaction between an intermediate of formula (XXXI) and an intermediate of formula (XXXII) according to Scheme 21 wherein $L^b$ is defined as I or Br, and wherein all other variables are defined as before. In Scheme 21, intermediates of formula (XXXI) and (XXXII) may be commercially available or may be prepared according to conventional reaction procedures generally know in the art. The coupling reaction can be performed in the presence of a suitable base such as, for example, $Cs_2CO_3$ or $Ag_2CO_3$. The reaction can be performed in a reaction-inert solvent such as, for example, $H_2O$, $CH_3CN$ or DMF. The reaction typically is performed in the presence of a catalyst system comprising a suitable catalyst such as palladium(II) acetate ($Pd(OAc)_2$) or 1,1-bis(diphenylphosphinoferrocenedichloropalladiumII) ($Pd(dppf)Cl_2$), and a ligand such as triphenylphosphine. Stirring, elevated temperatures (for example between 60 an 140° C.) may enhance the rate of the reaction.

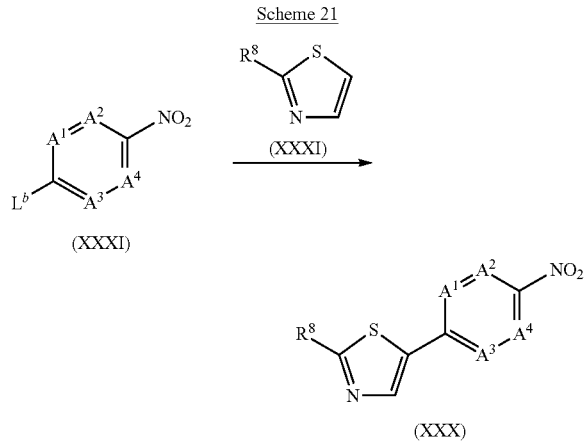

Experimental Procedure 22

An intermediate of formula (XXVII), wherein $Het^1$ is restricted as shown in Scheme 22, hereby named intermediate of formula (XXXIII), can be prepared via a decarboxylation reaction of a compound of formula (XXXIV) as depicted in Scheme 22 wherein $L^x$ is defined as Br, I or Cl, and wherein all other variables are defined as hereinabove. The reaction can be performed in a solvent such as quinoline or DMF in the presence of copper(II) oxide (CuO), or in a mixture of DMF/EtOH or isopropanol, both in the absence of CuO. The reaction can be performed under microwave assisted conditions. The reaction typically requires high temperatures (up to 150° C.).

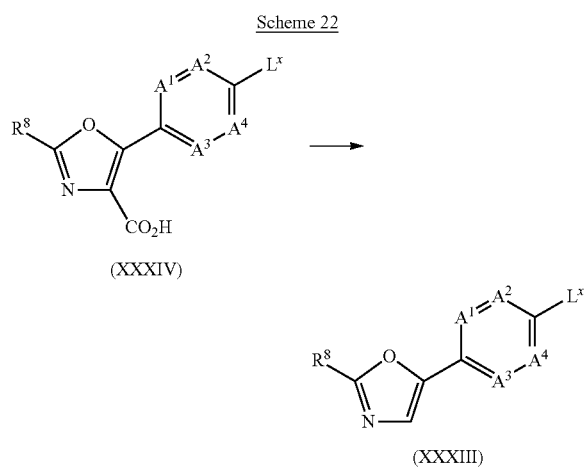

Experimental Procedure 23

An intermediate of formula (XXXIV) can be prepared via hydrolysis of the carboxylic ester function of a compound of formula (XXXV) as depicted in Scheme 23 wherein $L^x$ is defined as Br, I or Cl, and wherein all other variables are defined as before. This reaction can be performed either in acidic conditions or in basic conditions. It will be preferably performed in basic conditions in the presence of a base such as NaOH or LiOH in a mixture of dioxane and water at room temperature.

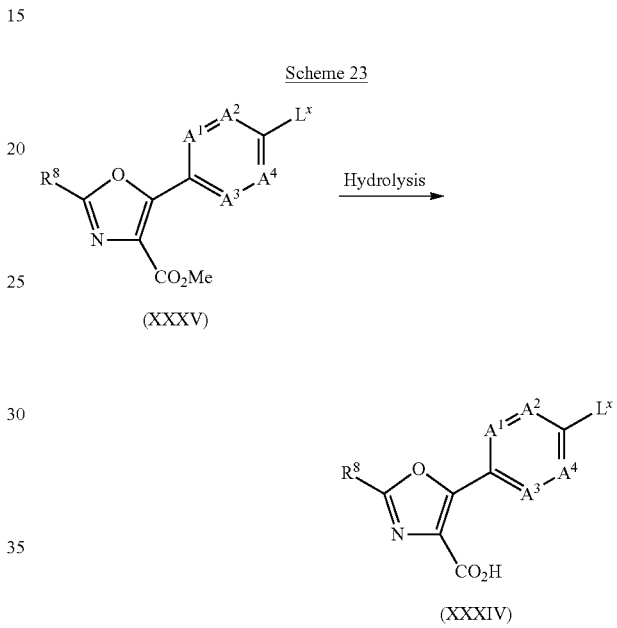

Experimental Procedure 24

An intermediate of formula (XXXV) can be prepared via a coupling reaction between an intermediate of formula (XXXVI) and an intermediate of formula (XXXVII) as depicted in Scheme 24 wherein $L^x$ is defined as Br, I or Cl, wherein $L^c$ is defined as Br or I, and wherein all other variables are defined as hereinbefore. Intermediates of formula (XXXVI) and (XXXVII) may be commercially available or may be prepared according to conventional reaction procedures generally known in the art. The coupling reaction is performed in the presence of a suitable base such as, for example, $Cs_2CO_3$ or $Ag_2CO_3$. The reaction can be performed in a reaction-inert solvent such as, for example, $CH_3CN$, toluene or DMF. The reaction typically is performed in the presence of a catalyst system comprising a suitable catalyst such as palladium(II) acetate ($Pd(OAc)_2$) or [1,1'-Bis(diphenylphosphino)ferrocene]dichloropalladium(II) (Pd(dppf) $Cl_2$), and a ligand such as, for instance, triphenylphosphine or tri-o-tolylphosphine. Stirring, elevated temperatures (for example between 60 an 140° C.) may enhance the rate of the reaction.

Scheme 24

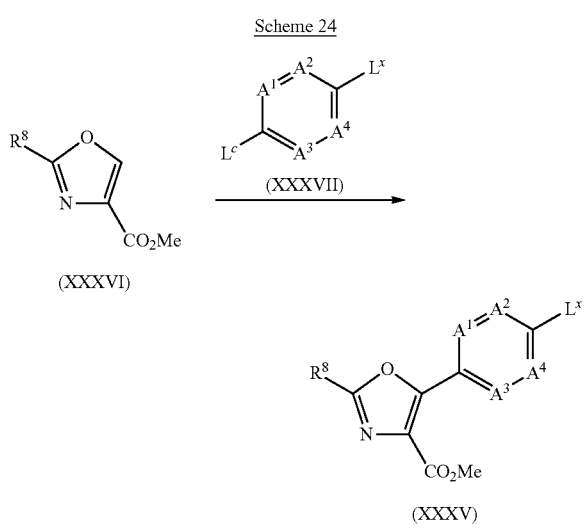

Experimental Procedure 25

An intermediate of formula (III) wherein $X^2$ is restricted to $CR^5$ with $R^5$ being —$CH_2NH_2$, hereby named an intermediate of (XXXVIII), can be prepared by the reduction of an intermediate of formula (XXXIX) according to conventional reaction procedures generally known in the art. This reduction may be performed in the presence of a suitable reducing agent such as, for example, Raney Nickel. The reaction can be performed in a protic solvent such as, for example, MeOH in the presence of ammonia.

Scheme 25

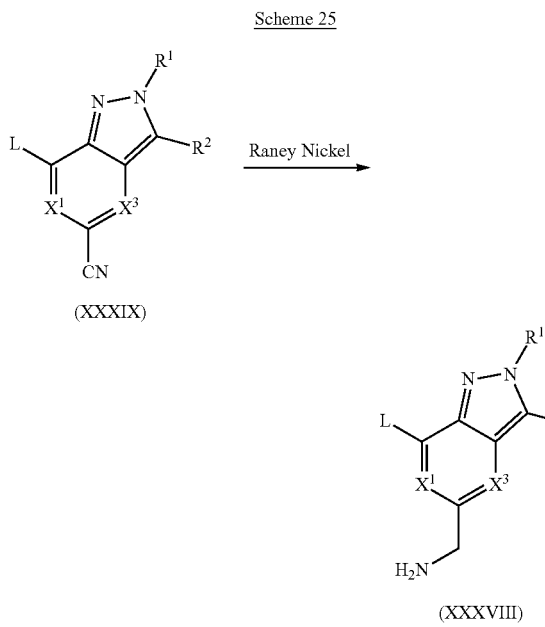

The primary amino group can be further alkylated and/or acylated to provide other intermediates of formula (III) wherein $X^2$ is restricted to $CR^5$ with $R^5$ being —$CH_2NR^3R^4$.

Experimental Procedure 26

An intermediate of formula (XV) wherein $X^2$ is restricted to $CR^5$ with $R^5$ being —CN, hereby named an intermediate of formula (XL), can be prepared by a metal mediated cyanation of an intermediate of formula (XV) wherein $X^2$ is restricted to $CR^5$ with $R^5$ being $L^d$ (wherein $L^d$ is I or Br), hereby named an intermediate of formula (XLI), as illustrated in Scheme 26. An intermediate of formula (XLI) may be commercially available or may be prepared according to conventional reaction procedures generally known in the art. This cyanation reaction typically can be performed in the presence of a suitable reagent, for example, zinc cyanide ($Zn(CN)_2$). The reaction typically can be performed in the presence of a catalyst such as tetrakis(triphenylphosphine)palladium (Pd($PPh_3$)$_4$) in a solvent such as, for example, DMF. Stirring and/or elevated temperatures (for example between 50-100° C.) may enhance the rate of the reaction.

Scheme 26

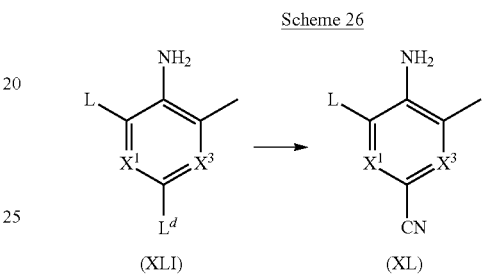

Experimental Procedure 27

Alternatively, an intermediate of formula (IX) can also be prepared, according to Scheme 27, by the reduction of an intermediate of formula (XLII) wherein R is defined as $C_{1-4}$alkyl, which may be commercially available or may be prepared according to conventional reaction procedures generally known in the art. This reaction can be performed in the presence of a suitable reducing agent such as, for example, diisobutylaluminium hydride (DIBAL). The reaction can be performed in a solvent such as, for example, DCM at low temperatures (e.g. −78° C.).

Scheme 27

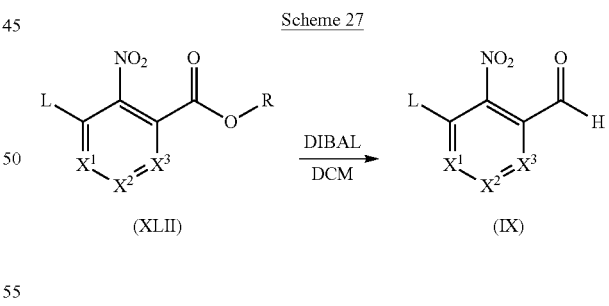

Experimental Procedure 28

An intermediate of formula (XLII) wherein R is defined as $C_{1-4}$alkyl, can be prepared by an alkylation reaction of an intermediate of formula (XLIII) according to conventional reaction procedures generally known in the art. As depicted in Scheme 28, the alkylation reaction is performed in the presence of a suitable base such as, for example, $Cs_2CO_3$ or $K_2CO_3$, and an alkylating reagent such as, for example, $C_{1-4}$alkyl-Y wherein Y is defined as Cl, Br or I. All other variables are as defined before. The reaction can be performed in an aprotic solvent such as, for example, DMF.

Scheme 28

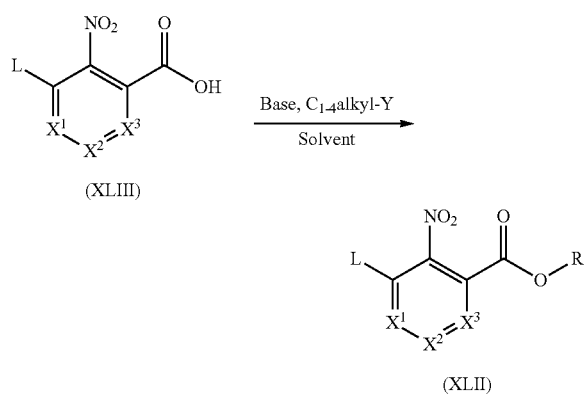

Experimental Procedure 29

An intermediate of formula (XLIII), can be prepared by the oxidation of an intermediate of formula (XLIV) which may be commercially available, according to conventional reaction procedures generally known in the art. The oxidation is performed in the presence of a suitable oxidizing system such as, for example, hydrogen peroxide ($H_2O_2$) in trifluoroacetic anhydride (TFAA), in a solvent such as, for example, DCM or $CH_3CN$.

Scheme 29

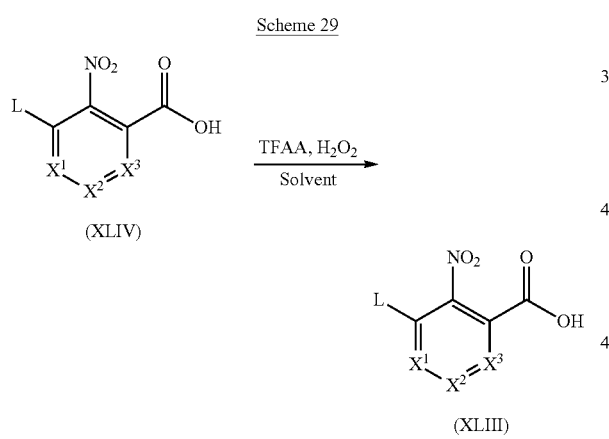

Experimental Procedure 30

An intermediate of formula (XIII), wherein
$X^1$ is restricted to CH;
$X^2$ is restricted to $CR^{5a}$ with $R^{5a}$ being $C_{1-4}$alkyloxy or $C_{1-4}$alkyl optionally substituted with one or more substituents each independently selected from the group consisting of $C_{1-4}$alkyloxy, fluoro, chloro and $NR^3R^4$;
$X^3$ is restricted to N;
L is defined as Br, I, or Cl,
hereby named an intermediate of formula (XLV) as shown in Scheme 30, can be prepared by the halogenation of an intermediate of formula (XLVI) according to conventional reaction procedures generally known in the art. This reaction typically may be performed in the presence of a halogenating reagent, such as, for example, phosphorus oxychloride, in a solvent such as, for example, $CH_3CN$. Stirring and/or elevated temperatures (for example between 50-100° C.) may enhance the rate of the reaction.

Scheme 30

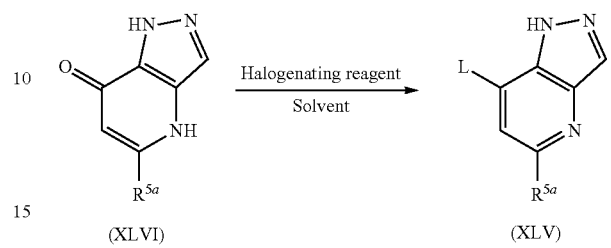

Experimental Procedure 31

An intermediate of formula (XLVI) wherein $^{Rya}$ is defined as in scheme 30, can be prepared by the cyclisation of an intermediate of formula (XLVII) according to conventional reaction procedures generally known in the art. This reaction typically can be performed at a high temperature (above 220° C.) in Dowtherm A (biphenyl-diphenyl ether mixture).

Scheme 31

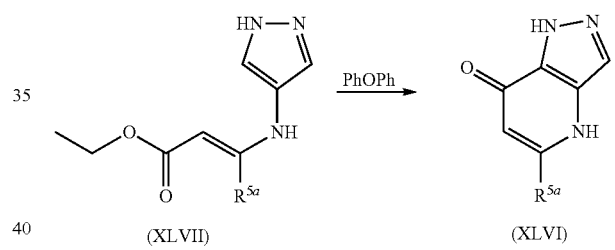

Experimental Procedure 32

An intermediate of formula (XLVII) can be prepared by the condensation of an intermediate of formula (XLVIII) with a β-ketoester of formula (XLIX), wherein $R^{5a}$ is defined as in scheme 30, according to conventional reaction procedures generally known in the art. This reaction typically can be performed in the presence of a catalytical amount of p-toluenesulfonic acid, in a solvent such as, for example benzene or toluene.

Scheme 32

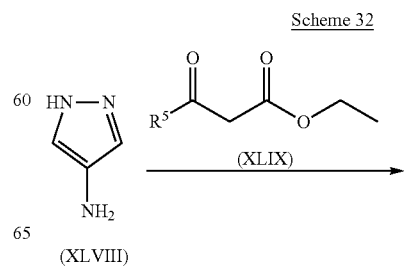

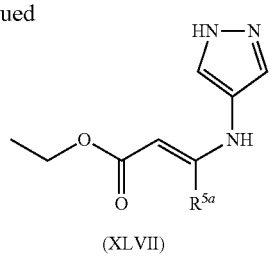

(XLVII)

Experimental Procedure 33

An intermediate of formula (XLVIII), can be prepared by conventional methods such as, for example, a reductive hydrogenation of intermediate (L).

Scheme 33

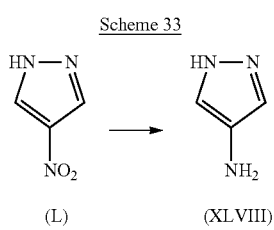

(L)        (XLVIII)

Experimental Procedure 34

An intermediate of formula (L), can be prepared by conventional methods such as, for example, the nitration of intermediate of formula (LI) in a mixture of sulphuric and nitric acids.

Scheme 34

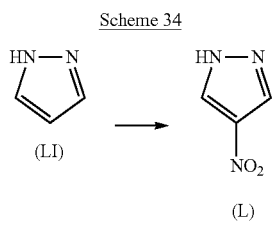 [SMILES: c1cn[nH]c1 ; O=[N+]([O-])c1cn[nH]c1]

(LI)        (L)

Experimental Procedure 35

An intermediate of formula (II), wherein Het[1] is restricted to (a-2) as shown in scheme 35, hereby named an intermediate of formula (LII), can also be prepared by a copper catalysed reaction of an intermediate of formula (LIII) with a (un)substituted imidazole or triazole of formula (XX) according to Scheme 35, wherein halo is defined as Br or I and wherein all other variables are defined as mentioned hereabove. The reaction may be performed under a protecting atmosphere such as, for example, $N_2$. Stirring, elevated temperatures (for example between 70-200° C.) and/or pressure may enhance the rate of the reaction. The reaction typically can be performed in an organic solvent such as, for example, DMSO or DMF. Optionally, the reaction may be performed in the presence of a base such as, for example, $K_2CO_3$, $Cs_2CO_3$, or $Et_3N$, and/or a ligand such as N,N'-dimethylethylenediamine or 1,10-phenanthroline. As a copper catalyst, copper salts such as, for example, $Cu_2O$, CuI or CuBr can be used in catalytic or stoichiometric amounts. The amino-group in intermediate of formula (LIII) can be protected before the reaction, and can be deprotected after reaction via the use of a suitable amino-protecting group in accordance with standard practice, for example, see T. W. Greene and P. G. M. Wuts in "Protective Groups in Organic Chemistry", John Wiley and Sons, 1999.

Scheme 35

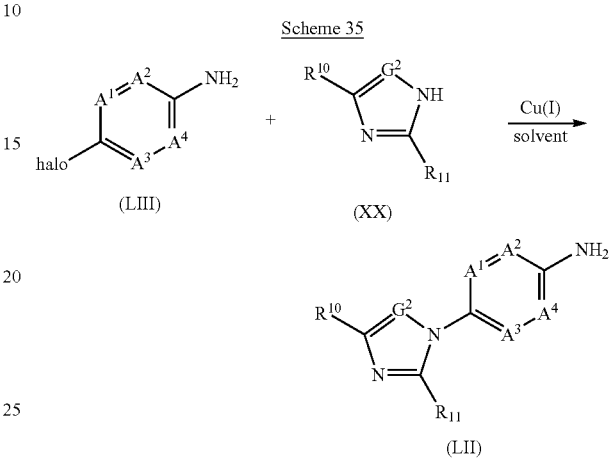

Experimental Procedure 36

An intermediate of formula (XXVII), wherein Het[1] is restricted to (a-2) and wherein in which $G^2$ is specifically CH, as shown in scheme 36, hereby named an intermediate of formula (LIV), can be prepared via acylation of intermediate (LVIII) to yield intermediate (LVII). This acylation reaction can be performed in the presence of a reaction inert solvent, such as THF, and optionally, either a suitable base, such as $Et_3N$, or in acidic conditions, such as a mixture of acetic anhydride and formic acid, according to Scheme 36. Subsequently, an intermediate of formula (LV) can be prepared via alkylation of an intermediate of formula (LVII) with an intermediate of formula (LVI). This reaction can be performed in the presence of a reaction inert solvent such as, for example, DMF, and a suitable base such as, for example, $Cs_2CO_3$ or $K_2CO_3$, and optionally in the presence of a catalytic amount of a iodide salt such as, for example, KI or NaI. Subsequently, a condensation reaction of intermediate (LV) with an ammonia source such as, for example, ammonium acetate ($NH_4OAc$) yields a compound of formula (LIV). In Scheme 36, halo is defined as Cl or Br, and all other variables are defined as mentioned hereinbefore.

Scheme 36

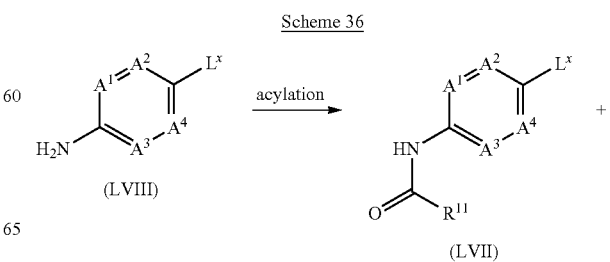

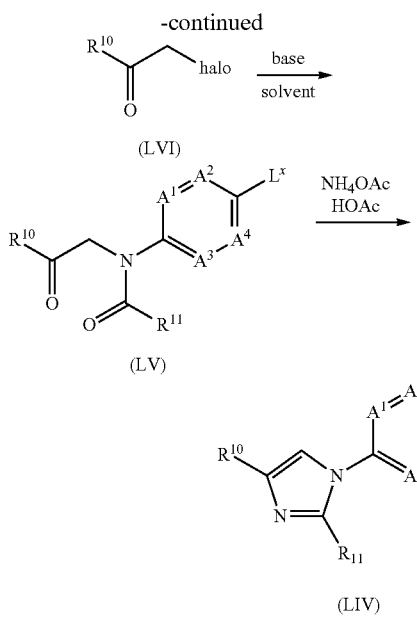

For the construction of the imidazole ring in an intermediate of formula (LIV), the order of introduction of $R^{10}$ and $R^{11}$ can be reversed. This type of reaction is described in US2006/0004013 for 1-(4-bromo-2-methoxyphenyl)-4-methyl-1H-Imidazole.

Where necessary or desired, any one or more of the following further steps in any order may be performed:

Compounds of formula (I), any subgroup thereof, addition salts, solvates, and stereochemical isomeric forms thereof can be converted into further intermediates and compounds according to the invention using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof therefore may be useful in the treatment or prevention of AD, TBI, MCI, senility, dementia, dementia with Lewy bodies, cerebral amyloid angiopathy, multi-infarct dementia, Down's syndrome, dementia associated with Parkinson's disease and dementia associated with beta-amyloid, preferably AD.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for use in the modulation of γ-secretase activity.

The invention also relates to a compound according to the general Formula (I), the stereoisomeric forms thereof and the pharmaceutically acceptable acid or base addition salts and the solvates thereof, for use in the treatment or prevention of diseases or conditions selected from AD, TBI, MCI, senility, dementia, dementia with Lewy bodies, cerebral amyloid angiopathy, multi-infarct dementia, or Down's syndrome.

In an embodiment, said disease or condition is preferably Alzheimer's disease.

The invention also relates to a compound according to the general Formula (I), the stereoisomeric forms thereof and the pharmaceutically acceptable acid or base addition salts and the solvates thereof, for use in the treatment of said diseases.

The invention also relates to a compound according to the general Formula (I), the stereoisomeric forms thereof and the pharmaceutically acceptable acid or base addition salts and the solvates thereof, for the treatment of said diseases.

The invention also relates to a compound according to the general formula (I), the stereoisomeric forms thereof and the pharmaceutically acceptable acid or base addition salts and the solvates thereof, for use in the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

The present invention also concerns to the use of a compound of Formula (I) for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "HPLC" means high-performance liquid chromatography; "sat." means saturated; "aq." means aqueous; "r.t." means room temperature; "AcOH" means acetic acid; "RP" means reversed phase; "min" means minute(s); "h" means hour(s); "I.D." means internal diameter; "EtOAc" means ethyl acetate; "NaOAc" means sodium acetate; "KOtBu" means potassium tert-butoxide; "Et₃N" means triethylamine; "EtOH" means ethanol; "eq" means equivalent; "r.m." means reaction mixture(s); "DIPE" means diisopropyl ether; "THF" means tetrahydrofuran; "DME" means dimethoxyethane; "DMSO" means dimethyl sulfoxide; "BINAP" means [1,1'-binaphthalene]-2,2'-diylbis[diphenylphosphine] (racemic); "NH₄OAc" means ammonium acetate; "DMF" means N,N-dimethyl formamide; "X-Phos" means dicyclohexyl[2',4',6'-tris(1-methylethyl)[1,1'-biphenyl]-2-yl]phosphine; and "Pd₂(dba)₃" means tris[μ-[(1,2-η:4,5-η)-(1E,4E)-1,5-diphenyl-1,4-pentadien-3-one]]dipalladium.

A. Preparation of the Intermediates

Example A1 a) Preparation of Intermediate 1

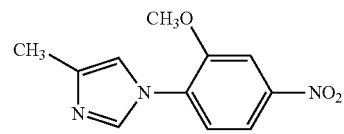

A mixture of 1-chloro-2-methoxy-4-nitrobenzene (50 g, 0.26 mol), 4-methyl-1H-imidazole (43.77 g, 0.53 mol) and K₂CO₃ (36.84 g, 0.26 mol) in DMSO (500 ml) was reacted in an autoclave under N₂ atmosphere for 6 h at 150° C. This reaction was repeated twice with 50 g of 1-chloro-2-methoxy-4-nitrobenzene each (150 g in total). The 3 r.m. were combined and poured out into ice-water (6 l). The solid was filtered off and washed with H₂O. The solid was dissolved in DCM and this solution was washed with H₂O. The separated organic layer was dried (MgSO₄), filtered and the solvent was evaporated. The residue was purified over silica gel on a glass filter (eluent: DCM/MeOH from 100/0 to 97/3). The product fractions were collected and the solvent was evaporated. The residue was suspended in DIPE, filtered off and dried in the oven. Yield: 48.54 g of intermediate 1 (26.0%).

b) Preparation of Intermediate 2a and Intermediate 2

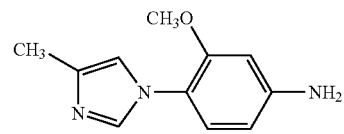

intermediate 2a: free base
intermediate 2: HCl salt (•HCl)

Intermediate 1 (13.2 g, 56.6 mmol) was dissolved in MeOH (250 ml). Pd/C (0.5 g) was added to the solution and the resulting suspension was stirred overnight at 50° C. under H₂ (atmospheric pressure). After uptake of H₂ (1 eq), the catalyst was filtered off. The organic layer was evaporated, yielding intermediate 2a (free base). Intermediate 2a was dissolved in a HCl/EtOH solution and stirred for 30 min. The solvent was removed in vacuo. The residue was crystallized from EtOH with a small amount of petroleum ether to yield the desired product. Yield: 4.7 g of intermediate 2 (41.0%; .HCl).

Example A2 a) Preparation of Intermediate 3 and Intermediate 4

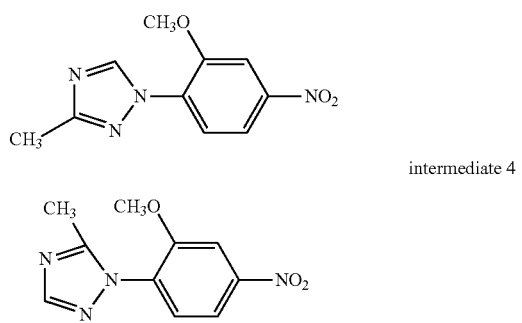

intermediate 3 intermediate 4

A mixture of 1-fluoro-2-methoxy-4-nitrobenzene (821 mg, 4.8 mmol), 5-methyl-1H-1,2,4-triazole (800 mg, 9.63 mmol), $K_2CO_3$ (4.8 mmol) and DMSO (8 ml) was stirred at 120° C. for 1 h. After cooling, the r.m. was poured into ice water. The solid was filtered off, washed with $H_2O$ and dried (in vacuo; 50° C.). Yield: 0.554 g of intermediate 3 (49%). The aq. layer was sat. with NaCl, extracted with DCM and the organic layer was dried ($MgSO_4$), filtered and the solvent was evaporated. The residue was purified by column chromatography over silica gel (eluent: DCM). The desired fraction was collected and the solvent was evaporated. Yield: 0.147 g of intermediate 4 (13%).

b) Preparation of Intermediate 5

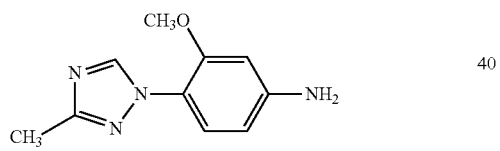

MeOH (50 ml) was added to Pd/C 10% (150 mg) under $N_2$ atmosphere. Subsequently, a 0.4% thiophene solution in DIPE (1 ml) and intermediate 3 (550 mg, 2.348 mmol) were added. The r.m. was stirred at 25° C. under $H_2$ atmosphere until 3 eq of $H_2$ was absorbed. The catalyst was filtered off over diatomaceous earth. The filtrate was evaporated and the residue was suspended in DIPE, filtered off and dried in vacuo. Yield: 0.350 g of intermediate 5 (73.0%).

Example A3 a) Preparation of Intermediate 6

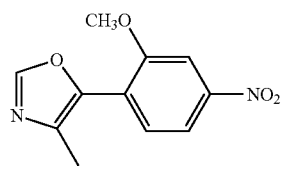

$K_2CO_3$ (9.6 g, 69.5 mmol) and 1-methyl-1-tosylmethylisocyanide (8 g, 38.2 mmol) were added to a solution of 2-formyl-5-nitroanisole (6.29 g, 34.7 mmol) in MeOH (150 ml), and the r.m. was refluxed for 4 h. The r.m. was concentrated under reduced pressure, the residue was dissolved in DCM and the organic phase was washed with $H_2O$, dried ($MgSO_4$), filtered and the solvent was evaporated in vacuo. The residue was purified by flash chromatography over silica gel (eluent: n-heptane/EtOAc from 100/0 to 50/50). The product fractions were collected and the solvent was evaporated. Yield: 6.24 g of intermediate 6 (77%).

b) Preparation of Intermediate 7

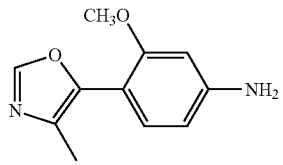

MeOH (150 ml) was added to Pd/C 10% (1 g) under a $N_2$ atmosphere. Subsequently, a 0.4% thiophene solution in DIPE (1 ml) and intermediate 6 (6.24 g, 26.6 mmol) were added. The r.m. was stirred at 25° C. under a $H_2$ atmosphere until 3 eq of $H_2$ was absorbed. The catalyst was filtered off over diatomaceous earth and the filtrate was evaporated. Yield: 5.4 g of intermediate 7 (99%).

Example A4 a) Preparation of Intermediate 8

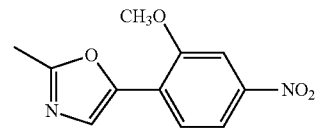

Iodobenzene diacetate (2.47 g, 7.68 mmol) and trifluoromethanesulfonic acid (1.35 ml, 15.3 mmol) were stirred in $CH_3CN$ (40 ml) at r.t. for 1 h under $N_2$. Subsequently, the mixture was heated to reflux temperature. 2'-Methoxy-4'-nitro-acetophenone (1.0 g, 5.12 mmol) was added at once to the solution and the r.m. was refluxed for 2 h, then cooled to r.t., and the solvent was evaporated. The residue was partioned between saturated aqueous sodium hydrogen carbonate (200 ml) and EtOAc (200 ml). The organic layer was separated and washed with brine, dried ($MgSO_4$), filtered and evaporated to give a brown solid. The product was purified by flash column chromatography over silica gel (eluent: DCM/MeOH from 100/0 to 99/1). The product fractions were collected and the solvent was evaporated (reduced pressure). Yield: 0.42 g of intermediate 8 (35%).

b) Preparation of Intermediate 9

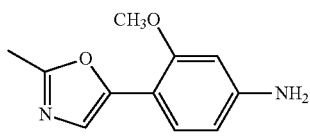

MeOH (50 ml) was added to Pd/C 10% (0.250 g) under a N$_2$ atmosphere. Subsequently, a 0.4% thiophene solution in DIPE (2 ml) and intermediate 8 (0.946 g, 4.04 mmol) were added. The r.m. was stirred at 25° C. under a H$_2$ atmosphere until 3 eq of H$_2$ was absorbed. The catalyst was filtered off over diatomaceous earth and the filtrate was evaporated. The product was triturated in DIPE, filtered off and dried under vacuum. Yield: 0.66 g of intermediate 9 (80%).

Example A5 a) Preparation of Intermediate 10

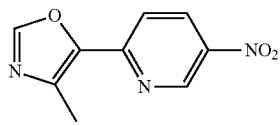

First K$_2$CO$_3$ (36 g, 262 mmol) and then 1-methyl-1-tosyl-methylisocyanide (35 g, 167 mmol) were added to a solution of 5-nitropyridine-2-carboxaldehyde (20 g, 131 mmol) in MeOH (500 ml) and the r.m. was refluxed for 4 h. The r.m. was concentrated under reduced pressure, the residue was dissolved in DCM and the organic phase was washed with H$_2$O, dried (Na$_2$SO$_4$), filtered and the solvent was evaporated in vacuo. The residue was purified by flash chromatography over Silica gel (eluent: petroleum ether/EtOAc 4/1). The product fractions were collected and the solvent was evaporated. Yield: 15 g of intermediate 10 (56%).

b) Preparation of Intermediate 11

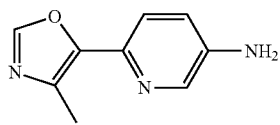

A solution of intermediate 10 (10 g, 48.7 mmol) in THF (300 ml) was added to a solution of NH$_4$Cl (2.6 g, 48.7 mmol) in H$_2$O (100 ml). Iron (16.3 g, 292 mmol) was added and the r.m. was refluxed for 4 h. The precipitate was removed by filtration and the filtrate evaporated in vacuo. The residue was dissolved in EtOAc and the organic layer was washed with H$_2$O, dried (Na$_2$SO$_4$), filtered and the solvent was evaporated in vacuo. The residue was dissolved in a 2 N HCl solution and the aq. phase was washed with DCM, made basic by addition of a 2 N NaOH solution and the product was extracted with EtOAc. The organic layer was washed dried (Na$_2$SO$_4$), filtered and the solvent was evaporated in vacuo to yield 6 g of intermediate 11 (71%).

Example A6 a) Preparation of Intermediate 12

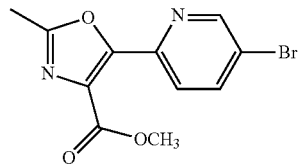 [SMILES: COC(=O)c1nc(C)oc1-c1ccc(Br)cn1]

A solution of 2-iodo-5-bromopyridine (13.7 g, 48.2 mmol), 2-methyl-4-oxazole carboxylic acid methyl ester (3.4 g, 24.1 mmol), palladium(II)acetate (0.54 g, 2.41 mmol), tri-o-tolylphosphine (1.47 g, 4.81 mmol) and Cs$_2$CO$_3$ (15.7 g, 48.2 mmol) in toluene (75 ml) was flushed with N$_2$, sealed and stirred overnight at 110° C. The catalyst was filtered over diatomaceous earth and the filtrate was evaporated. The crude product was purified by flash column chromatography over silica gel (eluent: DCM/MeOH(NH$_3$) from 100/0 to 98/2). The product fractions were collected and the solvent was evaporated. Yield: 5.64 g of intermediate 12 (64%).

b) Preparation of Intermediate 13

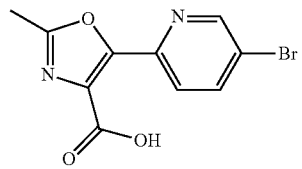 [SMILES: Cc1nc(C(=O)O)c(-c2ccc(Br)cn2)o1]

Intermediate 12 (5.64 g, 15.4 mmol) and LiOH (0.91 g, 38 mmol) were dissolved in a mixture of dioxane (40 ml) and H$_2$O (10 ml). The r.m. was stirred at r.t. for 5 h and was then treated with a 1 M HCl solution until pH 2. The precipitate was filtered off and dried under vacuum. The filtrate was extracted with CHCl$_3$ and the organic layer was dried (MgSO$_4$), filtered and the solvent was removed under reduced pressure to afford a solid. The two solid fractions were combined. Yield: 4.75 g of intermediate 13 (97%).

c) Preparation of Intermediate 14

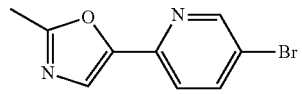

A solution of intermediate 13 (3.3 g, 11.65 mmol) in a mixture of DMF (75 ml) and EtOH (30 ml) was heated at 150° C. for 4 h under microwave conditions. After cooling, the d) Preparation of Intermediate 15

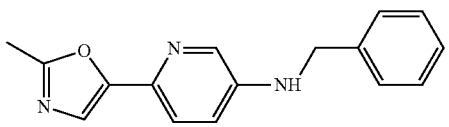 [SMILES: Cc1ncc(-c2ccc(NCc3ccccc3)cn2)o1]

[(R)-1-[(S)-2-(dicyclohexylphosphino)ferrocenyl]ethyl] di-tert-butylphosphine (Josi-Phos, 0.492 g, 0.89 mmol) and Pd(OAc)$_2$ were premixed in DME (2 ml) and then added to a solution of intermediate 14 (4.25 g, 17.8 mmol) and sodium tert-butoxide (2.39 g, 6.69 mmol) in DME (18 ml). Lastly, N-benzylamine (2.28 g, 21.33 mmol) was added and the r.m. was stirred at 100° C. for 9 h. After cooling, the r.m. was diluted with DCM and filtered over diatomaceous earth. The filtrate was concentrated under reduced pressure. The residue was purified by column chromatography over silica gel (eluent: DCM/MeOH(NH$_3$) from 100/0 to 98/2). The product fractions were collected and the solvent was removed under reduced pressure. Yield: 3.23 g of intermediate 15 (67%).

e) Preparation of Intermediate 16

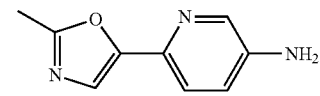

MeOH (50 ml) was added to Pd/C 10% (0.05 g) under a N$_2$ atmosphere. Intermediate 15 (0.15 g, 0.565 mmol) was added, and the r.m. was stirred under a H$_2$ atmosphere at 50° C. until 1 eq of H$_2$ was absorbed. The catalyst was filtered off over diatomaceous earth. The filtrate was evaporated. Yield: 0.105 g of intermediate 16 (95%).

Example A7 a) Preparation of Intermediate 17

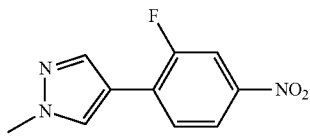 [SMILES: Cn1cc(-c2ccc([N+](=O)[O-])cc2F)cn1]

1-Methyl-4-(4,4,5,5-tetramethyl-1,3,2-dioxaborolan-2-yl)pyrazole (2.83 g, 13.63 mmol), CsF (3.11 g, 20.45 mmol) and [1,1'-bis(diphenylphosphino) ferrocene]dichloropalladium(II) (1.99 g, 13.64 mmol) were added to a solution of 4-bromo-3-fluoronitrobenzene (3.0 g, 4.81 mmol) in DMF (60 ml). The reaction mixture was flushed with N$_2$, sealed and stirred for 8 h at 100° C. After cooling, the solvent was evaporated. The residue was dissolved in DCM and the organic phase was washed with H$_2$O, dried (MgSO$_4$), filtered and the filtrate was concentrated under reduced pressure to give intermediate 17. This fraction was used as a crude in the next reaction step without further purification.

b) Preparation of Intermediate 18

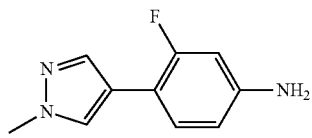

Intermediate 17 (3.0 g, 13.56 mmol) and iron (3.78 g, 67.8 mmol) were shaken in AcOH (24 ml) for 1.5 h. The solvent was evaporated. The residue was taken up in DCM and the organic layer was washed with a sat. Na$_2$CO$_3$ solution, dried (MgSO$_4$), filtered and concentrated under reduced pressure. The residue was triturated in DIPE and the resulting precipitate was filtered off. Yield: 0.72 g of intermediate 18 (28%).

Example A8 a) Preparation of Intermediate 19

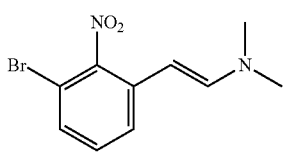

A mixture of 3-bromo-2-toluene (10.0 g, 42.29 mmol), dimethylformamide dimethyl acetal (15.55 g, 139 mmol) and pyrrolidine (3.29 g, 46.29 mmol) was stirred at 115° C. for 22 h. The solution was cooled to r.t. and used as such in the next reaction step.

b) Preparation of Intermediate 20

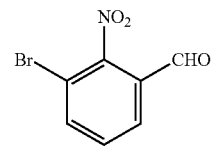 [SMILES: O=Cc1cccc(Br)c1[N+](=O)[O-]]

The crude solution from the previous reaction step, containing intermediate 19, was dropwise added at 0° C. to a stirring solution of sodium periodate (29.7 g, 139 mmol) in DMF (75 ml) and H$_2$O (100 ml). The r.m. was then allowed to warm to r.t. and was stirred for 3 h. The suspension was filtered over diatomaceous earth which was extensively washed with EtOAc. The filtrate was washed with H$_2$O and the organic phase was concentrated under reduced pressure. The residue was purified by chromatography over silica gel (eluent: n-heptane/DCM from 50/50 to 0/100). The product fractions were collected and the solvent was evaporated. Yield: 2.72 g of intermediate 20 (20% yield over two reaction steps).

c) Preparation of Intermediate 21

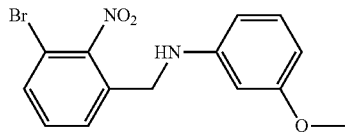 [SMILES: COc1cccc(NCc2cccc(Br)c2[N+](=O)[O-])c1]

Sodium triacetoxyborohydride (1.38 g, 6.5 mmol) was added portionwise to a stirring solution of intermediate 20 (1.0 g, 4.34 mol), 3-methoxyaniline (0.53 g, 4.34 mmol) and acetic acid (1.3 g, 21.7 mmol) in 1,2-dichloroethane (16 ml). The r.m. was stirred at r.t. for 4 h, washed with an aqueous $K_2CO_3$ solution and brine. The organic phase was dried ($MgSO_4$), filtered and the solvent was removed under reduced pressure. The residue was purified by flash chromatography over silica gel (eluent: n-heptane/DCM isocratic 50/50). The product fractions were collected and the solvent was evaporated. Yield: 0.65 g of intermediate 21 (41%).

d) Preparation of Intermediate 22

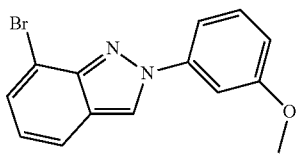 [SMILES: COc1cccc(-n2cc3cccc(Br)c3n2)c1]

A mixture of intermediate 21 (5.68 g, 16.8 mmol) and tin (II) chloride dihydrate (7.6 g, 33.7 mmol) in EtOH (100 ml) was stirred at 40° C. overnight. The solvent was evaporated and the residue was suspended in $H_2O$ and the product was extensively extracted with DCM. The organic phase was dried ($MgSO_4$), filtered and the solvent was removed (reduced pressure). The residue was purified by chromatography over silica gel (eluent: n-heptane/DCM from 40/60 up to 0/100). The product fractions were collected and the solvent was evaporated. Yield: 3.63 g of intermediate 22 (71%).

e) Preparation of Intermediate 23

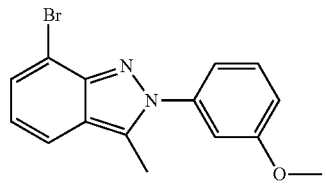 [SMILES: COc1cccc(-n2nc3c(Br)cccc3c2C)c1]

A 2 M solution of lithium diisopropylamide in THF was added dropwise to a solution of intermediate 22 (3.0 g, 9.9 mmol) in THF at −78° C. The r.m. was allowed to warm to 0-5° C. and was stirred for 15 min. The mixture was cooled again to −78° C. and $CH_3I$ (2.1 g, 14.8 mmol) was added. The temperature of the r.m. was allowed to rise slowly to r.t. and was stirred for 16 h. $H_2O$ was added and the product was extracted with diethyl ether. The organic phase was dried ($MgSO_4$), filtered and the solvent was removed under reduced pressure. The residue was purified by chromatography over silica gel (eluent: n-heptane/DCM from 50/50 up to 0/100). The product fractions were collected and the solvent was evaporated. Yield: 3.63 g of intermediate 23 (71%).

Example A9 a) Preparation of Intermediate 24

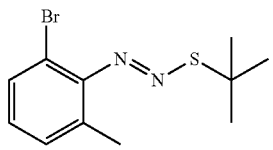

2-Bromo-6-methylaniline (1.18 g, 6.34 mmol) was stirred at 60° C. in a 6 N HCl aq. solution for 30 min and the r.m. was cooled to 0° C. A solution of $NaNO_2$ (0.481 g, 6.98 mmol) in $H_2O$ (1.5 ml) was added dropwise and the r.m. was stirred at 0° C. for an additional hour. The r.m. was buffered (pH between 4 and 5) by the addition of a sat. aqueous NaOAc solution, and subsequently the mixture was added all at once to an ice-cold solution of tert-butyl mercaptan (0.63 g, 6.98 mmol) in EtOH (25 ml). The r.m. was allowed to warm to r.t and stirred overnight. The r.m. was partitioned between EtOAc (100 ml) and $H_2O$ (100 ml). The water phase was extracted with EtOAc and the combined organic layers were dried ($MgSO_4$), filtered and the solvent was removed under reduced pressure. Yield: 1.7 g of intermediate 24 (70%).

b) Preparation of Intermediate 25

A solution of intermediate 24 (1.7 g, 4.44 mmol) in DMSO (20 ml) was dropwise added to a solution of KOtBu (6.64 g, 59 mmol) in DMSO (50 ml). The r.m. was stirred for 2 hours at r.t. and was then poured on ice (300 g) containing a 1 N aqueous HCl solution (300 ml). The mixture was extracted with diethyl ether. The organic layer was separated, dried ($MgSO_4$), filtered and the solvent was removed under reduced pressure. The residue was purified by chromatography over silica gel (eluent: DCM). The product fractions were collected and the solvent was evaporated. Yield: 0.55 g of intermediate 25 (63%).

c) Preparation of Intermediate 26

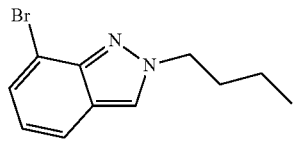

A mixture of intermediate 25 (0.54 g, 2.74 mmol) and dibutyl sulfate (0.493 g, 2.77 mmol) in toluene (7 ml) was stirred at 110° C. for 24 h. The r.m. was cooled to r.t. and washed with a sat. NaHCO₃ aq. solution. The organic phase was dried (MgSO₄) filtered and the solvent was evaporated. The crude oil was purified by chromatography over silica gel (eluent: n-heptane/DCM from 90/10 up to 70/30). The product fractions were collected and the solvent was evaporated. Yield: 0.335 g of intermediate 26 (43%).

Example A12

Preparation of Intermediate 27

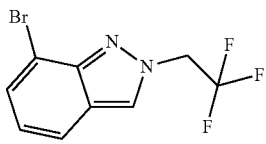 [SMILES: FC(F)(F)Cn1cc2cccc(Br)c2n1]

A solution on intermediate 25 (2 g, 10.1 mmol), 2,2,2-trifluoroethyl perfluorobutylsulfonate (4.9 g, 12.84 mmol), and Cs₂CO₃ (9.92 g, 30.45 mmol) was stirred at r.t. for 4 h. The r.m. was diluted with EtOAc and washed with H₂O. The organic layer was dried (MgSO₄), filtered and the solvent was evaporated. The resulting yellow oil was purified by chromatography over silica gel (eluent: n-heptane/DCM from 80/20 up to 0/100). The product fractions were collected and the solvent was evaporated. Yield: 1.08 g of intermediate 27 (38%).

Example A13 a) Preparation of Intermediate 28

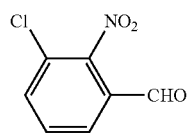

Pyridinium chlorochromate (67 g, 310 mmol) was added to a suspension of 3-chloro-2-nitrobenzylalcohol (25 g, 129 mmol), molecular sieves (40 g), and diatomaceous earth (40 g) in DCM (500 ml). The r.m. was stirred at r.t. for 2 h and then filtrated over silica (eluent: DCM). The product fractions were collected and the solvent was removed under reduced pressure. The residue was purified by chromatography over silica gel (eluent: DCM). The product fractions were collected and the solvent was evaporated. Yield: 22.5 g of intermediate 28 (94%).

b) Preparation of Intermediate 29

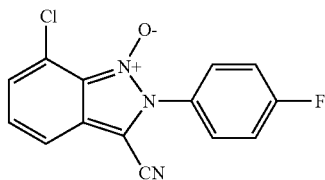 [SMILES: N#Cc1c2cccc(Cl)c2[n+]([O-])n1-c1ccc(F)cc1]

4-Fluoroaniline (1.83 g, 16.1 mmol) was dropwise added over 10 min to a solution of intermediate 28 (3 g, 16.1 mmol) in AcOH (50 ml). Trimethylsilyl cyanide (4.3 ml, 32.3 mmol) was added dropwise and the r.m. was stirred at r.t. for 16 h. The solvent was evaporated and the residue was partitioned between H₂O and DCM. The organic phase was separated, dried (MgSO₄), filtered and the solvent was removed under reduced pressure. The residue was dissolved in EtOH (100 ml) under gentle warming and a 0.5 M Na₂CO₃ solution (1.5 ml, 0.75 mmol) was added. Crystallization of the bright yellow indazole oxide began almost immediately. The mixture was allowed to cool to r.t. The precipitate was filtered off and recrystallised from EtOH/AcOH. Yield: 1.9 g of intermediate 29 (40%).

c) Preparation of Intermediate 30

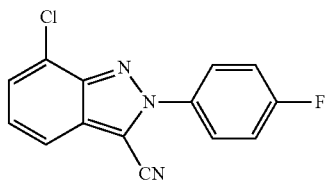 [SMILES: N#Cc1c2cccc(Cl)c2nn1-c1ccc(F)cc1]

Phosphorus trichloride (4.72 g, 34.3 mmol) was added to a suspension of intermediate 29 (1.6 g, 5.56 mmol) in CHCl₃ (25 ml) and the r.m. was refluxed for 1 h. After cooling, the r.m. was poured into ice-water. The aq. layer was basified (NaOH) and the product was extracted with DCM. The organic layer was separated, dried (MgSO₄), filtered and the solvent was evaporated under reduced pressure. The residue was crystallized from CH₃CN, filtered and dried under vacuum. Yield: 0.92 g of intermediate 30 (61%).

Example A14 a) Preparation of Intermediate 31

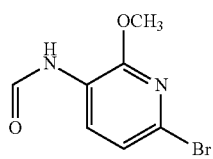 [SMILES: COc1nc(Br)ccc1NC=O]

A mixture of formic acid (12.8 ml, 340 mmol) and acetic acid anhydride (8.54 ml, (91 mmol) was stirred at r.t. for 40 min. Subsequently, a solution of 3-amino-6-bromo-2-methoxy-pyridine (5 g, 24.6 mmol) in THF (30 ml) was added dropwise to the mixture. The resulting r.m. was stirred overnight at 60° C., and was then cooled and poured into ice-water, resulting in the precipitation of a solid. The solid was filtered off, washed with water, and dried. Yield: 5.2 g of intermediate 31 (76%).

b) Preparation of Intermediate 32

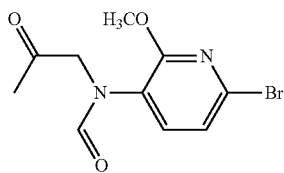 [SMILES: COc1nc(Br)ccc1N(C=O)CC(C)=O]

1-Chloro-propan-2-one (4.34 g, 46.9 mmol) was added dropwise to a mixture of intermediate 31 (5.2 g, 18.8 mmol), KI (0.343 g, 2.06 mmol) and $Cs_2CO_3$ (21.4 g, 65.9 mmol) in DMF (50 ml). The r.m. was stirred overnight at r.t. Subsequently, the r.m. was poured into ice-water and extracted with EtOAc. The combined organic layers were dried ($MgSO_4$), filtered and concentrated in vacuo. The residue was suspended in DIPE and the resulting solid was filtered off, washed with DIPE, and dried. Yield: 4.43 g of intermediate 32 (82%).

c) Preparation of Intermediate 33

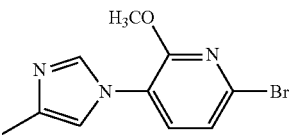

Intermediate 32 (4.4 g, 15.3 mmol) was added to a mixture of $NH_4OAc$ (5.41 g, 70.2 mmol) in AcOH (10 ml). The r.m. was heated at reflux for 1 h. The r.m. was cooled to r.t. and poured into a mixture of ice-water and EtOAc. The mixture was basified with a 50% w/v aq. NaOH solution to pH 9. The organic layer was separated, dried ($MgSO_4$), filtered and concentrated in vacuo. The resulting solid product was used as such in the next step. Yield: 3.78 g of crude intermediate 33.

d) Preparation of Intermediate 34

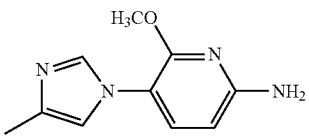

A mixture of 2-methyl-2-propanol sodium salt (0.717 g, 7.46 mmol), BINAP (464 mg, 0.746 mmol), $Pd_2(dba)_3$ (342 mg, 0.373 mmol), intermediate 33 (1.0 g, 3.73 mmol) and benzophenone imine (0.845 g, 4.66 mmol) in toluene (20 ml; previously deoxygenated) was stirred and heated at 100° C. for 2 h under microwave conditions. The mixture was cooled, and the solvent removed in vacuo. THF (50 ml) and a 1 N aq. HCl solution (50 ml) were added to the residue, and the mixture was stirred at r.t. for 1 h. The r.m. was basified with a 10% aq. $Na_2CO_3$ solution and extracted with EtOAc. The organic layers were dried ($MgSO_4$), filtered and the solvent was evaporated in vacuo. The product was purified by flash column chromatography over silica gel (eluent: DCM/MeOH from 100/0 to 95/5). The product fractions were collected and the solvent was evaporated. Yield: 0.6 g of intermediate 34 (52% yield over 2 reaction steps).

Example A15 a) Preparation of Intermediate 35

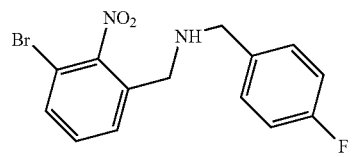 [SMILES: O=[N+]([O-])c1c(Br)cccc1CNCc1ccc(F)cc1]

Sodium triacetoxyborohydride (1.17 g, 5.5 mmol) was added portionwise to a stirring solution of intermediate 20 (0.8 g, 3.69 mol), 4-fluorobenzylamine (0.46 g, 3.69 mmol) and AcOH (1.1 g, 18.48 mmol) in 1,2-dichloroethane (12 ml). The r.m. was stirred at r.t. for 4 h, washed with an aq. $K_2CO_3$ solution and brine. The organic phase was dried ($MgSO_4$), filtered and the solvent was removed under reduced pressure. The residue was purified by flash chromatography over silica gel (eluent: n-heptane/DCM from 30/70 up to 0/100). The product fractions were collected and the solvent was evaporated. Yield: 0.70 g of intermediate 35 (41%).

b) Preparation of Intermediate 36

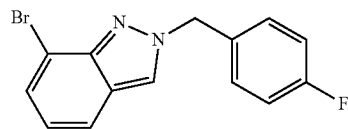

A mixture of intermediate 35 (0.6 g, 1.77 mmol) and tin(II) chloride dihydrate (0.80 g, 3.59 mmol) in EtOH (15 ml) was stirred at 40° C. overnight. The solvent was evaporated and the residue was suspended in $H_2O$ and the product was extensively extracted with DCM. The organic phase was dried ($MgSO_4$), filtered and the solvent was removed (reduced pressure). The residue was purified by RP preparative HPLC [RP Shandon Hyperprep® C18 BDS (8 µm, 250 g, I.D. 5 cm); mobile phase: a gradient of (0.25% $NH_4HCO_3$ solution in water)/MeOH/$CH_3CN$]. The product fractions were collected and the solvent was evaporated. Yield: 0.094 g of intermediate 36 (17%).

B. Preparation of the Compounds

Example B1

Preparation of Compound 1

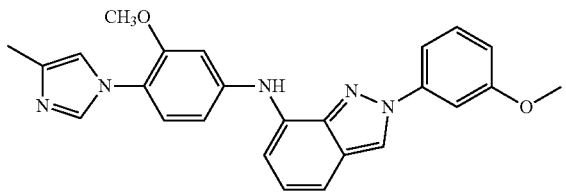

Intermediate 22 (0.28 g, 0.92 mmol), Pd$_2$(dba)$_3$ (0.084 g, 0.092 mmol), X-Phos (0.097 g, 0.203 mmol) and Cs$_2$CO$_3$ (0.90 g, 2.77 mmol) were added to a solution of intermediate 2a (0.187 g, 0.92 mmol) in 2-methyl-2-propanol (10 ml). The r.m. was heated at 110° C. for 20 h. After cooling, H$_2$O was added and the product was extracted with DCM. The organic phase was dried (MgSO$_4$), filtered and concentrated under reduced pressure. The residue was purified by preparative HPLC [RP Shandon Hyperprep® C18 BDS (8 μm, 250 g, I.D. 5 cm); mobile phase: (0.25% NH$_4$CO$_3$ solution in H$_2$O, CH$_3$CN)]. The product fractions were collected and concentrated under reduced pressure. Yield: 0.156 g of compound 1 (40%).

Example B2

Preparation of Compound 2

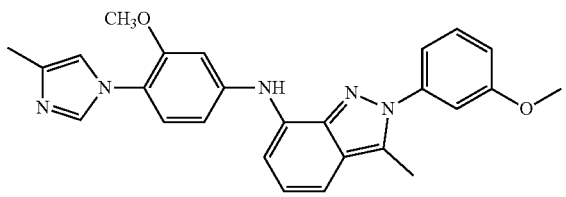

Intermediate 23 (0.152 g, 0.48 mmol), Pd$_2$(dba)$_3$ (0.044 g, 0.048 mmol), X-Phos (0.050 g, 0.105 mmol) and Cs$_2$CO$_3$ (0.47 g, 1.43 mmol) were added to a solution of intermediate 2a (0.097 g, 0.48 mmol) in 2-methyl-2-propanol (10 ml), and the r.m. was heated at 110° C. for 20 h. After cooling, H$_2$O was added and the product was extracted with DCM. The organic phase was dried (MgSO$_4$), filtered and concentrated under reduced pressure. The residue was purified by column chromatography over silica gel (eluent: DCM/MeOH from 100/0 to 95/5) and the product fractions were collected and worked up. The residue was crystallized from DIPE, filtered and dried under vacuum at 60° C. Yield: 0.131 g of compound 2 (62%).

Example B3

Preparation of Compound 3

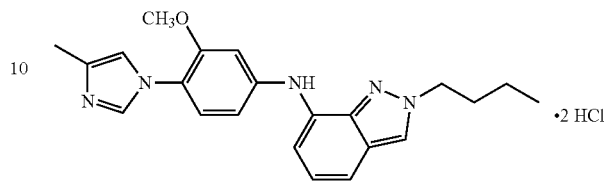

Intermediate 26 (0.10 g, 0.39 mmol), Pd$_2$(dba)$_3$ (0.036 g, 0.039 mmol), X-Phos (0.041 g, 0.087 mmol) and Cs$_2$CO$_3$ (0.38 g, 1.18 mmol) were added to a solution of intermediate 2a (0.080 g, 0.39 mmol) in 2-methyl-2-propanol (7 ml), and the r.m. was heated at 110° C. for 20 h. After cooling, H$_2$O was added and the product was extracted with DCM. The organic phase was dried (MgSO$_4$) filtered and concentrated under reduced pressure. The residue was purified by column chromatography over silica gel (eluent: DCM/MeOH from 100/0 to 96/4) and the product fractions were collected and worked up, yielding the crude compound 3a (free base of compound 3). The product was dissolved DIPE and converted into its HCl-salt by the addition of 1 ml of a 6N HCl solution in 2-propanol, filtered off and dried under vacuum at 60° C. Yield: 0.070 g of compound 3 (39%; .2HCl).

Example B4

Preparation of Compound 4

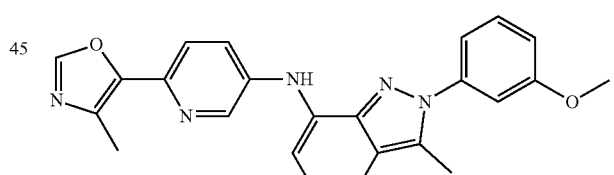

Intermediate 23 (0.317 g, 1 mmol), Pd$_2$(dba)$_3$ (0.091 g, 0.1 mmol), X-Phos (0.095 g, 0.2 mmol) and Cs$_2$CO$_3$ (0.98 g, 3 mmol) were added to a solution of intermediate 11 (0.175 g, 1 mmol) in 2-methyl-2-propanol (10 ml), and the r.m. was heated at 100° C. for 14 h. After cooling, H$_2$O was added and the r.m. was diluted with DCM and filtered over diatomaceous earth. The filtrate was washed with H$_2$O, dried (MgSO$_4$), filtered and concentrated under reduced pressure. The residue was purified by column chromatography over silica gel (eluent: DCM/MeOH(NH$_3$) from 100/0 to 98/2). The product fractions were collected and the solvent was evaporated. Yield: 0.198 g of compound 4 (48%).

Example B5

Preparation of Compound 5

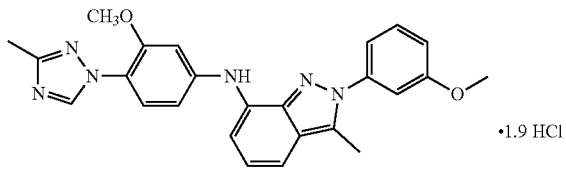

•1.9 HCl

Intermediate 23 (0.348 g, 1.1 mmol), Pd$_2$(dba)$_3$ (0.091 g, 0.1 mmol), X-Phos (0.105 g, 0.22 mmol) and Cs$_2$CO$_3$ (0.98 g, 3 mmol) were added to a solution of intermediate 5 (0.204 g, 1 mmol) in 2-methyl-2-propanol (12 ml), and the r.m. was heated at 110° C. for 20 h. After cooling, H$_2$O was added and the product was extracted with DCM. The organic phase was dried (MgSO$_4$), filtered and concentrated under reduced pressure. The residue was purified by column chromatography over silica gel (eluent: DCM/MeOH from 100/0 to 95/5). The product fractions were collected and worked up, yielding the crude compound 5a (free base of compound 5). The product was dissolved DIPE and converted into its HCl-salt by the addition of 2 ml of a 6N HCl solution in 2-propanol, filtered off and dried under vacuum at 60° C. Yield: 0.344 g of compound 5 (67%; 1.9HCl).

Example B6

Preparation of Compound 6

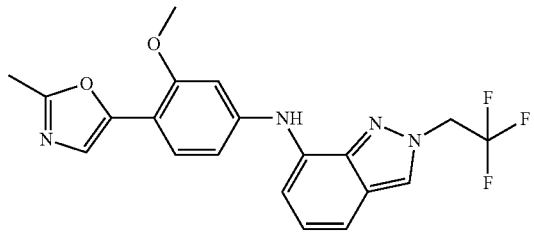 [SMILES: COc1cc(Nc2cccc3cn(CC(F)(F)F)nc23)ccc1-c1cnc(C)o1]

Intermediate 27 (0.204 g, 0.73 mmol), Pd$_2$(dba)$_3$ (0.064 g, 0.07 mmol), X-Phos (0.073 g, 0.15 mmol) and Cs$_2$CO$_3$ (0.68 g, 2.1 mmol) were added to a solution of intermediate 9 (0.142 g, 0.7 mmol) in 2-methyl-2-propanol (10 ml), and the r.m. was heated at 60° C. for 16 h. After cooling, H$_2$O was added and the r.m. was diluted with DCM and filtered over diatomaceous earth. The filtrate was washed with H$_2$O, was dried (MgSO$_4$), filtered and concentrated under reduced pressure. The residue was purified by column chromatography over silica gel (eluent: DCM/MeOH(NH$_3$) from 100/0 to 99/1) and the product fractions were collected and the solvent was evaporated. Yield: 0.081 g of compound 6 (29%).

Example B7

Preparation of Compound 7

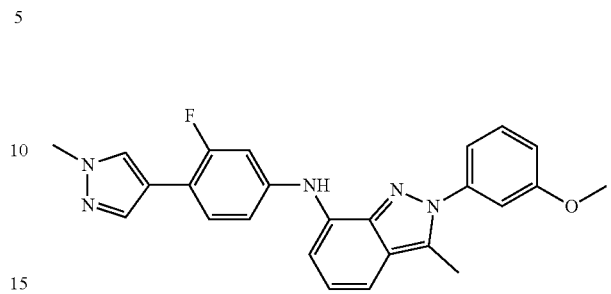

Intermediate 23 (0.222 g, 0.7 mmol), Pd$_2$(dba)$_3$ (0.064 g, 0.07 mmol), X-Phos (0.073 g, 0.154 mmol) and Cs$_2$CO$_3$ (0.684 g, 2.1 mmol) were added to a solution of intermediate 18 (0.175 g, 1 mmol) in 2-methyl-2-propanol (12 ml). The r.m. was heated for 20 h at 100° C. After cooling, H$_2$O was added and the r.m. was diluted with DCM and filtered over diatomaceous earth. The filtrate was washed with H$_2$O, was dried (MgSO$_4$), filtered and concentrated under reduced pressure. The residue was purified by column chromatography over silica gel (eluent: DCM/MeOH(NH$_3$) from 100/0 to 98/2) and the product fractions were collected and the solvent was evaporated. Yield: 0.054 g of compound 7 (18%).

Example B8 a) Preparation of Compound 32

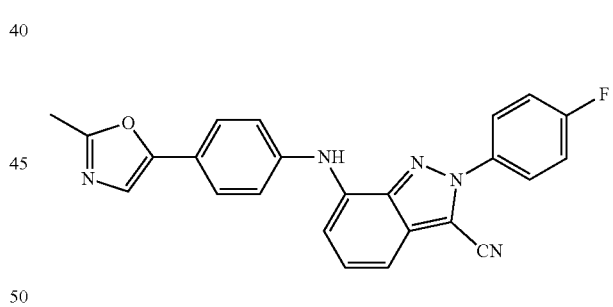

Intermediate 30 (0.198 g, 0.73 mmol), Pd$_2$(dba)$_3$ (0.066 g, 0.073 mmol), X-Phos (0.076 g, 0.16 mmol) and Cs$_2$CO$_3$ (0.714 g, 2.2 mmol) were added to a solution of 4-(2-methyl-1,3-oxazol-5-yl)aniline (0.127 g, 0.73 mmol) in 2-methyl-2-propanol (12 ml), and the r.m. was heated for 20 h at 110° C. After cooling, H$_2$O was added and the product was extracted with DCM. The organic phase was dried (MgSO$_4$) filtered and concentrated under reduced pressure. The residue was purified by column chromatography over silica gel (eluent: DCM/MeOH from 100/0 to 98/2) and the product fractions were collected and worked up. The product was crystallized from CH$_3$CN, filtered off and dried (in vacuo; 60° C.). Yield: 0.098 g of compound 32 (33%).

Preparation of Compound 8

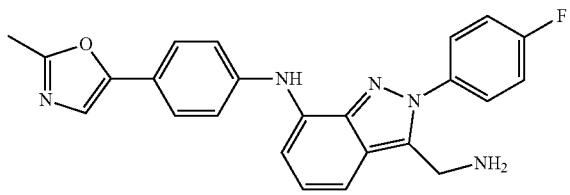 [SMILES: Cc1ncc(-c2ccc(Nc3cccc4c(CN)n(-c5ccc(F)cc5)nc34)cc2)o1]

MeOH/NH$_3$ (40 ml) was added to Raney Nickel (0.05 g) under a N$_2$ atmosphere. Subsequently, compound 32 (0.042 g, 0.10 mmol) was added. The r.m. was stirred at 14° C. under a H$_2$ atmosphere until 2 eq of H$_2$ was absorbed. The catalyst was filtered off over diatomaceous earth and the filtrate was evaporated. The residue was purified by flash chromatography over silica gel (eluent: DCM/MeOH(NH$_3$) 95/5). The product fractions were collected and the solvent was evaporated. Yield: 0.010 g of compound 8 (23%).

Example B9

Preparation of Compound 9

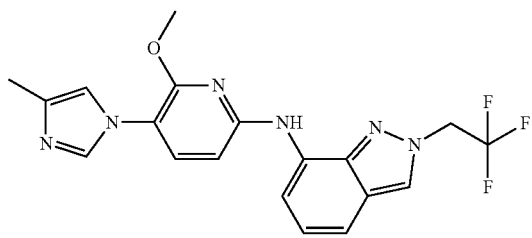 [SMILES: COc1nc(Nc2cccc3cn(CC(F)(F)F)nc23)ccc1-n1cnc(C)c1]

Intermediate 27 (0.278 g, 0.99 mmol), Pd$_2$(dba)$_3$ (0.083 g, 0.09 mmol), X-Phos (0.095 g, 0.2 mmol) and Cs$_2$CO$_3$ (0.885 g, 2.72 mmol) were added to a solution of intermediate 34 (0.185 g, 0.91 mmol) in 2-methyl-2-propanol (10 ml). The r.m. was heated at 70° C. for 16 h. After cooling, H$_2$O was added and the r.m. was diluted with DCM and filtered over diatomaceous earth. The filtrate was washed with H$_2$O, was dried (MgSO$_4$), filtered and concentrated under reduced pressure. The residue was purified by column chromatography over silica gel (eluent: DCM/MeOH(NH$_3$) from 100/0 to 98/2) and the product fractions were collected and the solvent was evaporated. Yield: 0.092 g of compound 9 (25%).

Example B10

Preparation of Compound 10

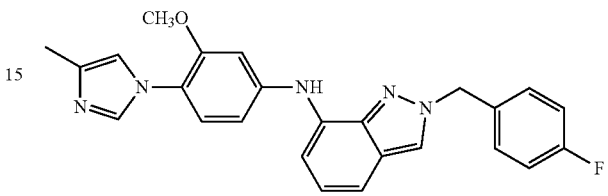

Intermediate 36 (0.094 g, 0.308 mmol), Pd$_2$(dba)$_3$ (0.028 g, 0.031 mmol), X-Phos (0.032 g, 0.068 mmol) and Cs$_2$CO$_3$ (0.301 g, 0.92 mmol) were added to a solution of intermediate 2a (0.062 g, 0.308 mmol) in 2-methyl-2-propanol (5 ml). The r.m. was heated at 110° C. for 20 h. After cooling, H$_2$O was added and the product was extracted with DCM. The organic phase was dried (MgSO$_4$), filtered and concentrated under reduced pressure. The residue was purified by column chromatography over silica gel (eluent: DCM/MeOH from 100/0 to 98/2. The product fractions were collected and concentrated under reduced pressure. Yield: 0.070 g of compound 10 (53%).

Compounds 1 to 57 in tables 1a and 1b list the compounds that were prepared by analogy to one of the above Examples. In case no salt form is indicated, the compound was obtained as a free base. 'Pr.' refers to the Example number according to which protocol the compound was synthesized. 'Co. No.' means compound number.

In order to obtain the HCl salt forms, several procedures known to those skilled in the art were used. In a typical procedure, for example, the crude residue (free base) was dissolved in DIPE or Et$_2$O and subsequently, a 6 N HCl solution in 2-propanol or a 1 N HCl solution in Et$_2$O was added dropwise. The mixture was stirred for 10 minutes and the product was filtered off. The HCl salt was dried in vacuo.

TABLE 1a

| Co. No. | Pr. | Het$^1$ | A$^1$ | X$^1$ | R$^1$ | R$^2$ | R$^5$ | salt form |
|---|---|---|---|---|---|---|---|---|
| 7 | B7 | 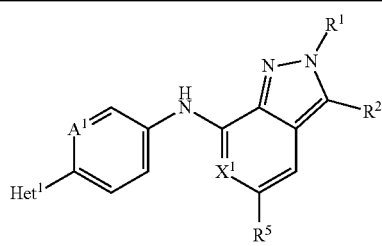 | CF | CH | |  | CH$_3$ | H | |

TABLE 1a-continued
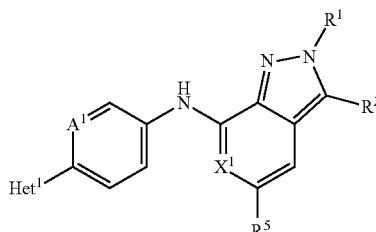
| Co. No. | Pr. | Het¹ | A¹ | X¹ | R¹ | R² | R⁵ | salt form |
|---|---|---|---|---|---|---|---|---|
| 9 | B3 | 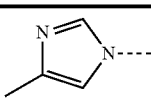 | COCH₃ | CH | CH₃ | H | H | |
| 3a | B3 | 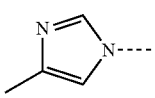 | COCH₃ | CH | 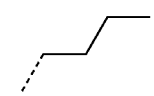 | H | H | |
| 3 | B3 | 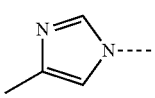 | COCH₃ | CH | 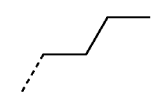 | H | H | •2 HCl |
| 10 | B3 | 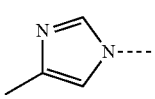 | COCH₃ | CH | 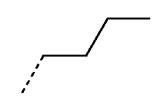 | CH₃ | H | •2 HCl |
| 11 | B3 | 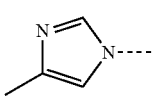 | COCH₃ | CH | 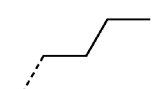 | H | CN | •2 HCl |
| 12 | B8.b | 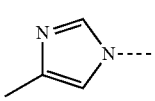 | COCH₃ | CH | 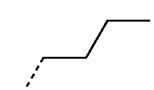 | H | 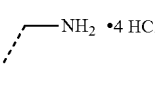 | •4 HCl |
| 13 | B3 | 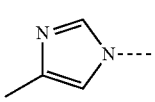 | COCH₃ | CH | 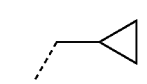 | H | H | •2 HCl |
| 1 | B1 | 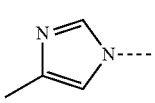 | COCH₃ | CH | 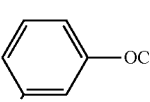 | H | H | |
| 2 | B2 | 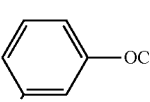 | COCH₃ | CH | 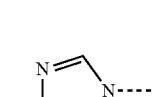 | CH₃ | H | |
| 14 | B2 | 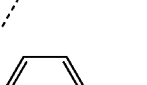 | COCH₃ | CH | 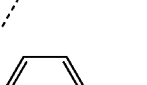 | CH₃ | H | |
| 15 | B2 B10 | 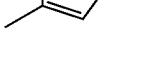 | COCH₃ | CH | 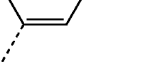 | H | H | |

TABLE 1a-continued

| Co. No. | Pr. | Het¹ | A¹ | X¹ | R¹ | R² | R⁵ | salt form |
|---|---|---|---|---|---|---|---|---|
| 16 | B2 | 4-methyl-imidazol-1-yl | COCH₃ | CH | 2,5-difluorophenyl | CH₃ | H | |
| 17 | B2 | 3-methyl-1,2,4-triazol-1-yl | COCH₃ | CH | CH₃ | H | H | |
| 18 | B6 | 3-methyl-1,2,4-triazol-1-yl | COCH₃ | CH | CH₂CF₃ | H | H | |
| 19 | B2 | 3-methyl-1,2,4-triazol-1-yl | COCH₃ | CH | 3-methoxyphenyl | H | H | |
| 5a | B5 | 3-methyl-1,2,4-triazol-1-yl | COCH₃ | CH | 3-methoxyphenyl | CH₃ | H | |
| 5 | B5 | 3-methyl-1,2,4-triazol-1-yl | COCH₃ | CH | 3-methoxyphenyl | CH₃ | H | •1.9 HCl |
| 20 | B2 | 3-methyl-1,2,4-triazol-1-yl | COCH₃ | CH | 2-isopropyl-4-methyl-6-(ethoxy)phenyl | CH₃ | H | |
| 21 | B6 | 3-methyl-1,2,4-triazol-1-yl | COCH₃ | N | CH₂CF₃ | H | CH₃ | |
| 22 | B2 | 3-methyl-1,2,4-triazol-1-yl | CF | CH | CH₂CH₂CF₃ | CH₃ | H | |

TABLE 1a-continued
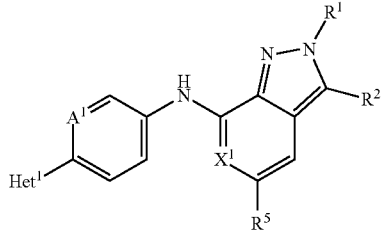
| Co. No. | Pr. | Het¹ | A¹ | X¹ | R¹ | R² | R⁵ | salt form |
|---|---|---|---|---|---|---|---|---|
| 23 | B2 | 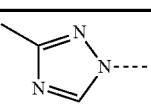 | CF | CH | 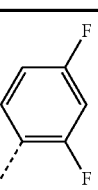 | CH₃ | H | |
| 24 | B2 | 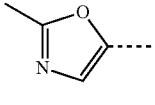 | CH | CH | CH₃ | H | H | |
| 25 | B3 | 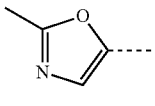 | CH | CH |  | H | H | •2 HCl |
| 26 | B3 | 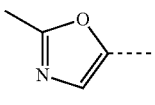 | CH | CH | 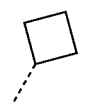 | H | H | •1.2 HCl |
| 27 | B3 | 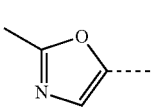 | CH | CH | 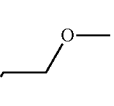 | H | H | •1.5 HCl •1.25 H₂O |
| 28 | B2 | 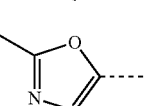 | CH | CH | 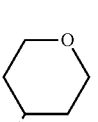 | H | H | |
| 29 | B2 | 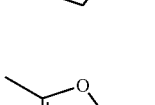 | CH | CH | 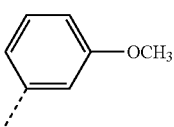 | CH₃ | H | |
| 30 | B2 | 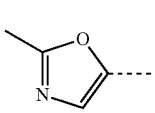 | CH | CH | 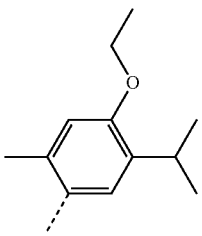 | CH₃ | H | |
| 8 | B8.b | 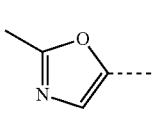 | CH | CH | 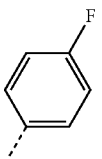 |  | H | |

TABLE 1a-continued
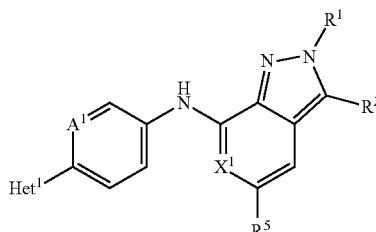
| Co. No. | Pr. | Het¹ | A¹ | X¹ | R¹ | R² | R⁵ | salt form |
|---|---|---|---|---|---|---|---|---|
| 31 | B3 | 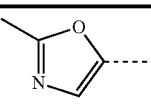 | CH | CH | 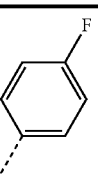 4-F-phenyl | CH₃ | H | •1.5 HCl |
| 32 | B8.a | 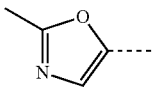 | CH | CH | 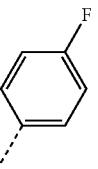 4-F-phenyl | CN | H | |
| 33 | B2 | 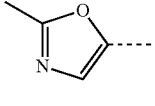 | CH | CH | 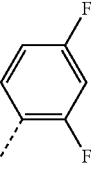 2,5-diF-phenyl | CH₃ | H | |
| 34 | B2 | 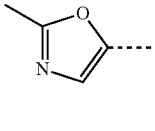 | CH | CH | 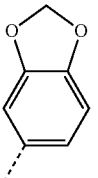 benzodioxole | H | H | |
| 35 | B2 | 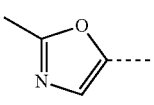 | CH | N | 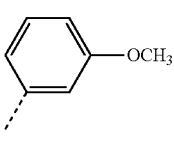 3-OCH₃-phenyl | CH₃ | H | |
| 36 | B3 | 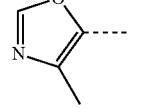 | COCH₃ | CH | 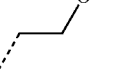 CH₂CH₂OCH₃ | H | H | •1.5 HCl •0.18 H₂O |
| 6 | B6 | 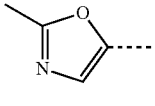 | COCH₃ | CH |  CH₂CF₃ | H | H | |
| 37 | B3 | 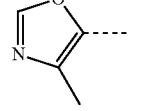 | COCH₃ | CH |  CH₂-cyclopropyl | H | H | •2 HCl |
| 38 | B3 | 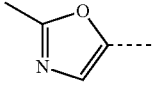 | COCH₃ | CH |  CH₂-cyclopropyl | H | H | •HCl |

TABLE 1a-continued
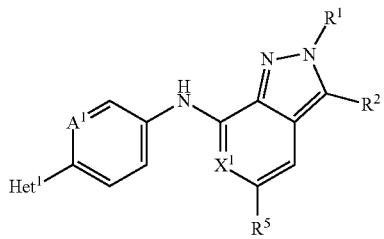
| Co. No. | Pr. | Het¹ | A¹ | X¹ | R¹ | R² | R⁵ | salt form |
|---|---|---|---|---|---|---|---|---|
| 39 | B3 | 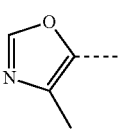 | COCH₃ | CH | 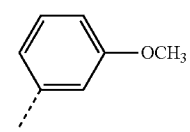 | CH₃ | H | •1.9 HCl |
| 40 | B2 | 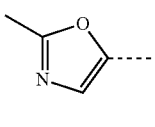 | COCH₃ | CH | 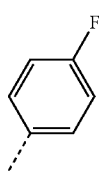 | CH₃ | H | |
| 41 | B6 | 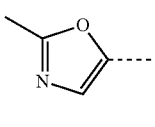 | COCH₃ | N |  | H | CH₃ | |
| 42 | B2 | 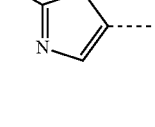 | COCH₃ | N | 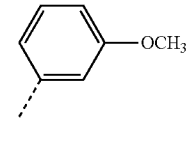 | CH₃ | H | |
| 43 | B3 | 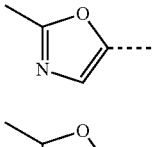 | N | CH |  | H | H | •2 HCl |
| 44 | B6 | 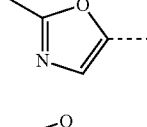 | N | CH |  | H | H | |
| 4 | B4 | 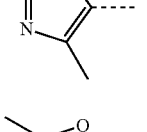 | N | CH | 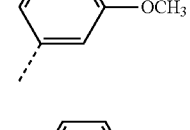 | CH₃ | H | |
| 45 | B2 | 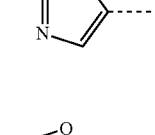 | N | CH | 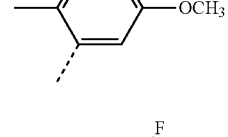 | CH₃ | H | |
| 46 | B2 | 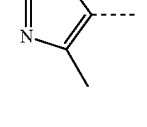 | N | CH | 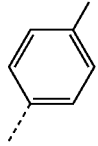 | CH₃ | H | |

TABLE 1a-continued

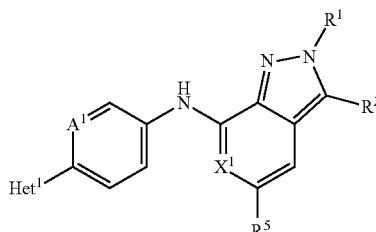

| Co. No. | Pr. | Het¹ | A¹ | X¹ | R¹ | R² | R⁵ | salt form |
|---|---|---|---|---|---|---|---|---|
| 47 | B2 | 2-methyl-oxazol-5-yl | N | CH | 4-fluorophenyl | CH₃ | F | |
| 48 | B2 | 2-isopropyl-oxazol-5-yl | CH | CH | —CH₂CF₃ | H | H | |
| 49 | B2 | 2-methyl-thiazol-5-yl | COCH₃ | CH | CH₃ | H | H | |
| 50 | B2 | 2-methyl-thiazol-5-yl | COCH₃ | CH | 2,5-difluorophenyl | CH₃ | H | |
| 52 | B9 | 4-methyl-imidazol-1-yl | CF | CH | —CH₂CF₃ | H | H | |
| 53 | B1 | 1-methyl-pyrazol-5-yl | CH | CH | 3-methoxyphenyl | CH₃ | H | •2 HCl •0.5 H₂O |

TABLE 1B

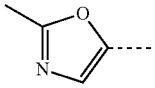

| Co. No. | Pr. | Het¹ | A¹ | A² | X² | X³ | salt form |
|---|---|---|---|---|---|---|---|
| 51 | B4 | 2-methyl-oxazol-5-yl | COCH₃ | CH | C—CH₃ | N | |
| 54 | B9 | 4-methyl-imidazol-1-yl | COCH₃ | N | CH | CH | |

TABLE 1B-continued

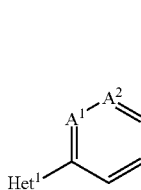

| Co. No. | Pr. | Het¹ | A¹ | A² | X² | X³ | salt form |
|---|---|---|---|---|---|---|---|
| 55 | B3 | 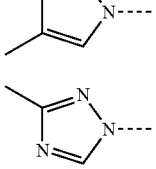 | CF | CH | N | CH | |
| 56 | B4 | 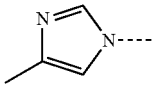 | COCH₃ | CH | C—CH(CH₃)₂ | N | |
| 57 | B4 | 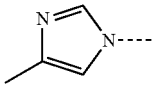 | COCH₃ | N | C—CH(CH₃)₂ | N | |

Analytical Part
LCMS (Liquid Chromatography/Mass Spectrometry)
General Procedure A The LC measurement was performed using an Acquity HPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. $N_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 45° C., unless otherwise indicated), a DAD and a column as specified in the respective methods below. Flow from the column was split to a MS spectrometer. The MS detector was configured with an electrospray ionization source. Mass spectra were acquired by scanning from 100 to 1000 in 1 sec using a dwell time of 0.1 sec. The capillary needle voltage was 3 kV and the source temperature was maintained at 140° C. $N_2$ was used as the nebulizer gas. Data acquisition was performed with a Waters-Micromass MassLynx-Openlynx data system.

LCMS Method 1

In addition to general procedure A: Reversed phase HPLC was carried out on a bridged ethylsiloxane/silica hybrid (BEH) C18 column (1.7 μm, 2.1×50 mm; Waters Acquity) with a flow rate of 0.8 ml/min. 2 Mobile phases (25 mM $NH_4OAc$ in $H_2O/CH_3CN$ 95/5; mobile phase B: $CH_3CN$) were used to run a gradient condition from 95% A and 5% B to 5% A and 95% B in 1.3 minutes (min) and hold for 0.3 min. An injection volume of 0.5 μl was used. Cone voltage was 10 V for positive ionization mode and 20 V for negative ionization mode.

LCMS Method 2

In addition to general procedure A: Reversed phase HPLC was carried out on a BEH C18 column (1.7 μm, 2.1×50 mm; Waters Acquity) with a flow rate of 0.8 ml/min. 2 Mobile phases (mobile phase A: 0.1% formic acid in $H_2O$/MeOH 95/5; mobile phase B: MeOH) were used to run a gradient condition from 95% A and 5% B to 5% A and B in 1.3 min and hold for 0.2 min. An injection volume of 0.5 μl was used. Cone voltage was 10 V for positive ionization mode and 20 V for negative ionization mode.

LCMS Method 3

In addition to general procedure B: Reversed phase HPLC was carried out on an Atlantis C18 column (3.5 μm, 4.6×100 mm) with a flow rate of 1.6 ml/min. 2 Mobile phases (mobile phase A: 70% MeOH+30% $H_2O$; mobile phase B: 0.1% formic acid in $H_2O$/MeOH 95/5) were employed to run a gradient condition from 100% B to 5% B+95% A in 9 min and hold these conditions for 3 min. An injection volume of 10 μl was used. Cone voltage was 10 V for positive ionization mode and 20 V for negative ionization mode.

LCMS Method 4

In addition to general procedure A: Reversed phase HPLC (Ultra Performance Liquid Chromatography) was carried out on a BEH C18 column (1.7 μm, 2.1×50 mm; Waters Acquity) with a flow rate of 0.8 ml/min. 2 Mobile phases (25 mM $NH_4OAc/CH_3CN$ 95/5; mobile phase B: $CH_3CN$) were used to run a gradient condition from 95% A and 5% B to 5% A and 95% B in 1.3 min and hold for 0.3 min. An injection volume of 0.5 μl was used. Cone voltage was 30 V for positive ionization mode and 30 V for negative ionization mode.

LCMS Method 5

In addition to general procedure B: Column heater was set at 60° C. Reversed phase HPLC was carried out on an Xterra MS C18 column (3.5 μm, 4.6×100 mm) with a flow rate of 1.6 ml/min. 3 Mobile phases (mobile phase A: 95% 25 mM $NH_4OAc$+5% $CH_3CN$; mobile phase B: $CH_3CN$; mobile phase C: MeOH) were employed to run a gradient condition from 100% A to 50% B and 50% C in 6.5 min, to 100% B in 0.5 min and hold these conditions for 1 min and reequilibrate with 100% A for 1.5 min. An injection volume of 10 μl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./min. Maximum temperature was 400° C. Values are peak values.

The results of the analytical measurements are shown in table 2.

TABLE 2

Retention time ($R_t$) in min., [M + H]⁺ peak (protonated molecule), LCMS method and m.p. (melting point in ° C.).
(n.d. means not determined)

| Co. No. | $R_t$ | [M + H]⁺ | LCMS Method | m.p. (° C.) |
|---|---|---|---|---|
| 1 | 1.16 | 426 | 1 | n.d. |
| 2 | 1.17 | 440 | 1 | 184.4 |
| 3 | 1.10 | 376 | 1 | n.d. |
| 4 | 1.19 | 412 | 1 | n.d. |
| 5 | 1.17 | 441 | 1 | n.d. |
| 6 | 1.09 | 403 | 4 | n.d. |
| 7 | 1.47 | 428 | 2 | 239.1 |
| 8 | 0.97 | 414 | 4 | 137.0 |
| 9 | 0.89 | 334 | 1 | n.d. |

TABLE 2-continued

Retention time (R$_t$) in min., [M + H]$^+$ peak (protonated molecule), LCMS method and m.p. (melting point in ° C.).
(n.d. means not determined)

| Co. No. | R$_t$ | [M + H]$^+$ | LCMS Method | m.p. (° C.) |
|---|---|---|---|---|
| 10 | 1.15 | 390 | 1 | n.d. |
| 11 | 1.00 | 401 | 2 | 134.7 |
| 12 | 0.70 | 405 | 2 | n.d. |
| 13 | 1.01 | 374 | 2 | n.d. |
| 14 | 1.34 | 510 | 2 | n.d. |
| 15 | 1.07 | 428 | 1 | n.d. |
| 16 | 6.70 | 446 | 5 | n.d. |
| 17 | 7.60 | 335 | 3 | n.d. |
| 18 | 0.95 | 403 | 4 | n.d. |
| 19 | 1.11 | 427 | 1 | n.d. |
| 20 | 10.06 | 511 | 3 | n.d. |
| 21 | 0.99 | 418 | 4 | 203.4 |
| 22 | 1.09 | 433 | 1 | 135.6 |
| 23 | 1.21 | 435 | 1 | 146.9 |
| 24 | 8.52 | 305 | 3 | 168.7 |
| 25 | 1.38 | 345 | 2 | n.d. |
| 26 | 1.41 | 345 | 2 | n.d. |
| 27 | 1.30 | 349 | 2 | n.d. |
| 28 | 1.01 | 375 | 4 | 224.8 |
| 29 | 1.25 | 411 | 1 | 152.2 |
| 30 | 1.63 | 481 | 2 | n.d. |
| 31 | 1.23 | 399 | 1 | n.d. |
| 32 | 1.26 | 410 | 4 | 237.9 |
| 33 | 1.32 | 417 | 1 | 139.9 |
| 34 | 1.47 | 411 | 2 | 175.0 |
| 35 | 1.03 | 412 | 2 | 185.0 |
| 36 | 1.29 | 379 | 2 | n.d. |
| 37 | 1.36 | 375 | 2 | n.d. |
| 38 | 1.41 | 375 | 2 | n.d. |
| 39 | 1.23 | 441 | 1 | n.d. |
| 40 | 1.25 | 429 | 1 | 164.4 |
| 41 | 1.13 | 418 | 4 | 213.8 |
| 42 | 1.10 | 442 | 2 | 194.4 |
| 43 | 1.29 | 346 | 2 | n.d. |
| 44 | 1.25 | 374 | 2 | 153.4 |
| 45 | 1.13 | 426 | 4 | n.d. |
| 46 | 1.17 | 400 | 1 | n.d. |
| 47 | 1.12 | 418 | 4 | n.d. |
| 48 | 1.42 | 401 | 2 | 103.9 |
| 49 | 1.31 | 351 | 2 | n.d. |
| 50 | 1.39 | 463 | 4 | n.d. |
| 51 | 0.89 | 418 | 4 | 211.5 |
| 52 | n.d. | n.d. | — | 144.9 |
| 53 | 1.21 | 410 | 4 | n.d. |
| 54 | 1.02 | 403 | 4 | 206.0 |
| 55 | 0.77 | 391 | 4 | n.d. |
| 56 | 0.90 | 446 | 4 | n.d. |
| 57 | 0.96 | 446 | 4 | 172.5 |

$^1$H NMR

For a number of compounds, $^1$H NMR spectra were recorded on a Bruker DPX-360 or on a Bruker DPX-400 spectrometer with standard pulse sequences, operating at 360 MHz and 400 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

Co. No. 1: (360 MHz, CDCl$_3$) δ ppm 2.31 (s, 3 H), 3.84 (s, 3 H), 3.92 (s, 3 H), 6.89 (s, 1 H), 6.92-7.01 (m, 4 H), 7.02-7.09 (m, 1 H), 7.09-7.15 (m, 1 H), 7.19 (d, J=8.3 Hz, 1 H), 7.24 (d, J=8.3 Hz, 1 H), 7.39-7.48 (m, 2 H), 7.49-7.56 (m, 1 H), 7.64 (s, 1 H), 8.38 (s, 1 H).

Co. No. 2: (360 MHz, DMSO-d$_6$) δ ppm 2.14 (s, 3 H), 2.64 (s, 3 H), 3.75 (s, 3 H), 3.84 (s, 3 H), 6.92-7.00 (m, 2 H), 7.01 (s, 1 H), 7.09-7.16 (m, 3 H), 7.19 (d, J=8.5 Hz, 1 H), 7.23-7.31 (m, 3 H), 7.52 (t, J=8.4 Hz, 1 H), 7.63 (d, J=1.1 Hz, 1 H), 8.33 (s, 1 H).

Co. No. 3: (360 MHz, DMSO-d$_6$) δ ppm 0.91 (t, J=7.3 Hz, 3 H), 1.27 (sxt, J=7.3 Hz, 2 H), 1.92 (quin, J=7.3 Hz, 2 H), 2.34 (s, 3 H), 3.79 (s, 3 H), 4.44 (t, J=6.9 Hz, 2 H), 6.91-7.01 (m, 2 H), 7.10 (d, J=7.3 Hz, 1 H), 7.16 (d, J=2.2 Hz, 1 H), 7.28 (d, J=8.4 Hz, 1 H), 7.37 (d, J=8.4 Hz, 1 H), 7.65 (s, 1 H), 8.38 (s, 1 H), 8.54 (br. s., 1 H), 9.28 (d, J=1.5 Hz, 1 H), 14.84 (br. s., 1 H).

Co. No. 4: (360 MHz, CDCl$_3$) δ ppm 2.61 (s, 3 H), 2.65 (s, 3 H), 3.88 (s, 3 H), 6.89 (s, 1 H), 6.99-7.06 (m, 2 H), 7.10-7.16 (m, 2 H), 7.20 (d, J=8.1 Hz, 1 H), 7.46 (t, J=8.4 Hz, 1 H), 7.58 (d, J=8.8 Hz, 1 H), 7.72 (dd, J=8.8, 2.6 Hz, 1 H), 7.83 (s, 1 H), 8.64 (d, J=2.6 Hz, 1 H).

Co. No. 5: (360 MHz, DMSO-d$_6$) δ ppm 2.39 (s, 3 H) 2.64 (s, 3 H) 3.80 (s, 3 H) 3.84 (s, 3 H) 6.95-7.04 (m, 2 H) 7.09-7.19 (m, 3 H) 7.22-7.35 (m, 3 H) 7.43 (d, J=8.78 Hz, 1 H) 7.52 (t, J=8.42 Hz, 1 H) 9.05 (br. s., 1 H).

Co. No. 6: (360 MHz, CDCl$_3$) δ ppm 2.53 (s, 3 H) 3.95 (s, 3 H) 5.00 (q, J=8.42 Hz, 2 H) 6.83 (s, 1 H) 6.92 (d, J=1.83 Hz, 1 H) 6.99 (dd, J=8.42, 1.83 Hz, 1 H) 7.06 (t, J=7.68 Hz, 1 H) 7.14 (d, J=6.95 Hz, 1 H) 7.18 (d, J=8.42 Hz, 1 H) 7.30 (s, 1 H) 7.67 (d, J=8.42 Hz, 1 H) 8.01 (s, 1 H).

Co. No. 7: (360 MHz, DMSO-d$_6$) δ ppm 2.63 (s, 3 H) 3.84 (s, 3 H) 3.87 (s, 3 H) 6.98 (t, J=7.68 Hz, 1 H) 7.07 (d, J=7.32 Hz, 1 H) 7.09-7.17 (m, 3 H) 7.22-7.32 (m, 3 H) 7.48-7.58 (m, 2 H) 7.79 (s, 1 H) 7.93-8.03 (m, 1 H) 8.41 (s, 1 H).

Co. No. 8: (360 MHz, DMSO-d$_6$) δ ppm 2.02 (br. s., 2 H) 2.45 (s, 3 H) 4.06 (s, 2 H) 6.94-7.02 (m, 1 H) 7.08 (d, J=7.32 Hz, 1 H) 7.31 (s, 1 H) 7.35 (m, J=8.78 Hz, 2 H) 7.43 (d, J=6.22 Hz, 1 H) 7.44-7.50 (m, 2 H) 7.53 (m, J=8.42 Hz, 2 H) 7.84-7.92 (m, 2 H) 8.41 (s, 1 H).

Co. No. 9: (360 MHz, CDCl$_3$) δ ppm 2.30 (s, 3 H), 3.82 (s, 3 H), 4.23 (s, 3 H), 6.76 (s, 1 H), 6.88 (s, 1 H), 6.90-6.96 (m, 2 H), 7.01 (t, J=7.7 Hz, 1 H), 7.11 (d, J=7.3 Hz, 1 H), 7.14-7.22 (m, 2 H), 7.63 (s, 1 H), 7.88 (s, 1 H).

Co. No. 10: (360 MHz, DMSO-d$_6$) δ ppm 0.92 (t, J=7.3 Hz, 3 H), 1.32 (sxt, J=7.3 Hz, 2 H), 1.85 (quin, J=7.3 Hz, 2 H), 2.34 (s, 3 H), 2.63 (s, 3 H), 3.79 (s, 3 H), 4.37 (t, J=7.3 Hz, 2 H), 6.87-6.99 (m, 2 H), 7.09 (d, J=7.2 Hz, 1 H), 7.14 (d, J=2.2 Hz, 1 H), 7.26 (d, J=8.3 Hz, 1 H), 7.37 (d, J=8.6 Hz, 1 H), 7.64 (s, 1 H), 8.48 (br. s., 1 H), 9.28 (d, J=1.5 Hz, 1 H), 15.01 (br. s., 1 H).

Co. No. 11: (360 MHz, DMSO-d$_6$) δ ppm 0.91 (t, J=7.32 Hz, 3 H) 1.28 (sxt, J=7.32 Hz, 2 H) 1.94 (quin, J=7.32 Hz, 2 H) 2.35 (d, J=0.73 Hz, 3 H) 3.82 (s, 3 H) 4.50 (t, J=7.32 Hz, 2 H) 7.08-7.15 (m, 2 H) 7.27 (d, J=2.20 Hz, 1 H) 7.47 (d, J=8.78 Hz, 1 H) 7.68 (t, J=1.10 Hz, 1 H) 7.91 (d, J=1.10 Hz, 1 H) 8.65 (s, 1 H) 8.89 (br. s., 1 H) 9.32 (d, J=1.46 Hz, 1 H) 14.99 (br. s., 1 H).

Co. No. 12: (400 MHz, DMSO-d$_6$) δ ppm 0.91 (t, J=7.27 Hz, 3 H), 1.26 (sxt, J=7.27 Hz, 2 H) 1.92 (quin, J=7.27 Hz, 2 H) 2.36 (s, 3 H), 3.83 (s, 3 H), 4.01 (q, J=5.65 Hz, 2 H) 4.44 (t, J=6.86 Hz, 2 H) 7.16 (dd, J=8.68, 2.22 Hz, 1 H) 7.23 (d, J=1.21 Hz, 1 H) 7.24 (d, J=2.02 Hz, 1 H) 7.35 (s, 1 H) 7.40 (d, J=8.48 Hz, 1 H) 7.63 (t, J=1.21 Hz, 1 H) 8.42 (br. s., 2 H) 8.45 (s, 1 H) 8.59 (br. s., 1 H) 9.29 (d, J=1.61 Hz, 1 H) 15.04 (br. s., 1 H).

Co. No. 13: (360 MHz, CDCl$_3$) δ ppm 0.54-0.63 (m, 2 H) 0.77-0.85 (m, 2 H) 1.47-1.61 (m, 1 H) 2.54 (s, 3 H) 3.87 (s, 3 H) 4.44 (d, J=7.32 Hz, 2 H) 6.94-7.09 (m, 3 H) 7.14-7.23 (m, 2 H) 7.30-7.39 (m, 2 H) 7.90 (br. s., 1 H) 8.22 (s, 1 H) 8.40 (br. s., 1 H).

Co. No. 14: (360 MHz, CDCl$_3$) δ ppm 1.21 (d, J=6.9 Hz, 6 H), 1.48 (t, J=6.9 Hz, 3 H), 2.00 (s, 3 H), 2.30 (s, 3 H), 2.42 (s, 3 H), 3.23-3.43 (m, 1 H), 3.80 (s, 3 H), 4.11 (q, J=6.9 Hz, 2 H), 6.80 (s, 1 H), 6.87 (s, 1 H), 6.90-6.96 (m, 3 H), 6.99-7.06 (m, 1 H), 7.11 (s, 1 H), 7.13-7.21 (m, 3 H), 7.63 (d, J=1.3 Hz, 1 H).

Co. No. 15: (360 MHz, CDCl$_3$) δ ppm 2.30 (s, 3 H), 3.81 (s, 3 H), 5.57 (s, 2 H), 6.83 (s, 1 H), 6.88 (s, 1 H), 6.90-6.97 (m, 2 H), 7.00-7.13 (m, 4 H), 7.14-7.19 (m, 2 H), 7.23-7.28 (m, 2 H), 7.63 (s, 1 H), 7.87 (s, 1 H).

Co. No. 16: (360 MHz, CDCl$_3$) δ ppm 2.31 (s, 3 H), 2.34 (t, J=1.8 Hz, 3 H), 3.83 (s, 3 H), 6.89 (d, J=5.1 Hz, 2 H), 6.92-6.99 (m, 2 H), 7.01-7.10 (m, 2 H), 7.14 (d, J=6.9 Hz, 1 H), 7.19 (d, J=8.3 Hz, 1 H), 7.25 (d, J=6.9 Hz, 1 H), 7.64 (d, J=1.1 Hz, 1 H), 7.81 (td, J=8.8, 5.8 Hz, 1 H), 8.37 (d, J=2.7 Hz, 1 H).

Co. No. 17: (360 MHz, CDCl$_3$) δ ppm 2.49 (s, 3 H) 3.87 (s, 3 H) 4.23 (s, 3 H) 6.81 (s, 1 H) 6.94-6.99 (m, 2 H) 7.03 (t, J=7.68 Hz, 1 H) 7.12 (d, J=6.95 Hz, 1 H) 7.20 (d, J=8.05 Hz, 1 H) 7.58 (d, J=9.15 Hz, 1 H) 7.88 (s, 1 H) 8.48 (s, 1 H).

Co. No. 19: (360 MHz, CDCl$_3$) δ ppm 2.50 (s, 3 H), 3.90 (s, 3 H), 3.93 (s, 3 H), 6.93-7.09 (m, 5 H), 7.13 (d, J=7.3 Hz, 1 H), 7.24 (d, J=7.3 Hz, 1 H), 7.42-7.48 (m, 2 H), 7.50-7.53 (m, 1 H), 7.62 (d, J=8.3 Hz, 1 H), 8.38 (s, 1 H), 8.50 (s, 1 H).

Co. No. 20: (360 MHz, CDCl$_3$) δ ppm 1.21 (d, J=6.6 Hz, 6 H), 1.48 (t, J=7.0 Hz, 3 H), 2.00 (s, 3 H), 2.42 (s, 3 H), 2.49 (s, 3 H), 3.33 (spt, J=6.8, 6.6 Hz, 1 H), 3.86 (s, 3 H), 4.11 (q, J=7.0 Hz, 2 H), 6.79 (s, 1 H), 6.92-6.96 (m, 2 H), 6.97-7.06 (m, 2 H), 7.11 (s, 1 H), 7.15-7.22 (m, 2 H), 7.56 (d, J=8.8 Hz, 1 H), 8.46 (s, 1 H).

Co. No. 22: (360 MHz, CDCl$_3$) δ ppm 2.10-2.32 (m, 4 H), 2.50 (s, 3 H), 2.63 (s, 2 H), 4.42 (t, J=6.7 Hz, 2 H), 6.79 (s, 1 H), 6.96-7.05 (m, 1 H), 7.05-7.23 (m, 4 H), 7.67 (t, J=8.4 Hz, 1 H), 8.42 (d, J=2.6 Hz, 1 H).

Co. No. 23: (360 MHz, CDCl$_3$) δ ppm 2.34 (s, 3 H), 2.51 (s, 3 H), 6.96 (s, 1 H), 7.01-7.26 (m, 5 H), 7.31 (d, J=8.4 Hz, 1 H), 7.70 (t, J=8.8 Hz, 1 H), 7.80 (td, J=8.8, 5.8 Hz, 1 H), 8.38 (d, J=2.6 Hz, 1 H), 8.44 (d, J=2.6 Hz, 1 H).

Co. No. 24: (360 MHz, CDCl$_3$) δ ppm 2.52 (s, 3 H) 4.23 (s, 3 H) 6.78 (br. s., 1 H) 7.00 (t, J=7.87 Hz, 1 H) 7.07-7.13 (m, 2 H) 7.17 (d, J=8.42 Hz, 1 H) 7.32 (m, J=8.42 Hz, 2 H) 7.56 (m, J=8.78 Hz, 2 H) 7.86 (s, 1 H).

Co. No. 25: (360 MHz, DMSO-d$_6$) δ ppm 0.42-0.51 (m, 2 H) 0.54-0.63 (m, 2 H) 1.33-1.52 (m, 1 H) 2.50 (s, 3 H) 4.30 (d, J=7.32 Hz, 2 H) 6.91-6.99 (m, 1 H) 7.04 (d, J=7.32 Hz, 1 H) 7.24 (d, J=8.05 Hz, 1 H) 7.34 (m, J=8.78 Hz, 2 H) 7.42 (s, 1 H) 7.54 (m, J=8.78 Hz, 2 H) 8.41 (s, 1 H).

Co. No. 26: (360 MHz, DMSO-d$_6$) δ ppm 1.80-1.98 (m, 2 H) 2.47 (s, 3 H) 2.48-2.56 (m, 2 H) 2.61-2.76 (m, 2 H) 5.16 (quin, J=8.42 Hz, 7.32 Hz, 1 H) 6.95 (t, J=8.42, 7.32 Hz, 1 H) 7.02 (d, J=7.32 Hz, 1 H) 7.20 (d, J=8.05 Hz, 1 H) 7.29-7.39 (m, 3 H) 7.54 (m, 2 H) 8.44 (s, 1 H).

Co. No. 27: (360 MHz, DMSO-d$_6$) δ ppm 2.47 (s, 3 H) 3.25 (s, 3 H) 3.84 (t, J=5.12 Hz, 2 H) 4.59 (t, J=5.12 Hz, 2 H) 6.95 (t, J=8.05, 7.32 Hz, 1 H) 7.02 (d, J=7.32 Hz, 1 H) 7.22 (d, J=8.05 Hz, 1 H) 7.29-7.39 (m, 3 H) 7.53 (m, 2 H) 8.33 (s, 1 H).

Co. No. 28: (360 MHz, CDCl$_3$) δ ppm 2.14-2.38 (m, 4 H) 2.52 (s, 3 H) 3.62 (td, J=11.25, 3.11 Hz, 2 H) 4.10-4.27 (m, 2 H) 4.57-4.72 (m, 1 H) 6.84 (s, 1 H) 7.00 (t, J=7.68 Hz, 1 H) 7.07-7.13 (m, 2 H) 7.18 (d, J=8.05 Hz, 1 H) 7.34 (m, 2 H) 7.56 (m, 2 H) 7.94 (s, 1 H).

Co. No. 29: (360 MHz, DMSO-d$_6$) δ ppm 2.45 (s, 3 H), 2.64 (s, 3 H), 3.84 (s, 3 H), 6.93-7.00 (m, 1 H), 7.07 (d, J=6.9 Hz, 1 H), 7.10-7.15 (m, 1 H), 7.23-7.29 (m, 3 H), 7.31 (s, 1 H), 7.35 (d, J=8.8 Hz, 2 H), 7.46-7.58 (m, 3 H), 8.39 (s, 1 H).

Co. No. 30: (360 MHz, CDCl$_3$) δ ppm 1.21 (d, J=6.9 Hz, 6 H), 1.47 (t, J=6.9 Hz, 3 H), 2.00 (s, 3 H), 2.41 (s, 3 H), 2.52 (s, 3 H), 3.33 (spt, J=6.9 Hz, 1 H), 4.11 (q, J=6.9 Hz, 2 H), 6.79 (s, 1 H), 6.94 (br. s., 1 H), 6.99-7.05 (m, 1 H), 7.09 (s, 1 H), 7.11 (s, 1 H), 7.16 (d, J=8.1 Hz, 2 H), 7.32 (m, J=8.4 Hz, 2 H), 7.54 (m, J=8.4 Hz, 2 H).

Co. No. 31: (360 MHz, DMSO-d$_6$) δ ppm 2.46 (s, 3 H), 2.61 (s, 3 H), 6.94-7.00 (m, 2 H), 7.08 (d, J=7.0 Hz, 1 H), 7.26 (d, J=8.3 Hz, 1 H), 7.30-7.39 (m, 3 H), 7.46 (t, J=8.8 Hz, 2 H), 7.53 (d, J=8.8 Hz, 2 H), 7.70-7.81 (m, 2 H).

Co. No. 32: (360 MHz, DMSO-d$_6$) δ ppm 2.47 (s, 3 H) 7.21 (dd, J=6.59, 1.46 Hz, 1 H) 7.28-7.38 (m, 3 H) 7.42 (d, J=8.78 Hz, 2 H) 7.52-7.64 (m, 4 H) 7.96-8.08 (m, 2 H) 8.97 (s, 1 H).

Co. No. 33: (360 MHz, CDCl$_3$) δ ppm 2.34 (t, J=1.8 Hz, 3 H), 2.53 (s, 3 H), 6.91 (s, 1 H), 7.00-7.09 (m, 2 H), 7.11 (s, 1 H), 7.13 (d, J=7.3 Hz, 1 H), 7.23 (d, J=8.1 Hz, 1 H), 7.35 (m, J=8.8 Hz, 2 H), 7.58 (m, J=8.4 Hz, 2 H), 7.82 (td, J=8.8, 5.8 Hz, 1 H), 8.36 (d, J=2.6 Hz, 1 H).

Co. No. 34: (360 MHz, CDCl$_3$) δ ppm 2.53 (s, 3 H) 6.08 (s, 2 H) 6.93 (d, J=8.42 Hz, 1 H) 6.96 (s, 1 H) 7.00-7.07 (m, 1 H) 7.09-7.13 (m, 2 H) 7.20 (d, J=8.05 Hz, 1 H) 7.32 (dd, J=8.42, 2.20 Hz, 1 H) 7.35 (m, 2 H) 7.42 (d, J=2.20 Hz, 1 H) 7.57 (m, 2 H) 8.25 (s, 1 H).

Co. No. 35: (360 MHz, DMSO-d$_6$) δ ppm 2.47 (s, 3 H) 2.60 (s, 3 H) 3.85 (s, 3 H) 7.09 (d, J=6.22 Hz, 1 H) 7.14-7.20 (m, 1 H) 7.27-7.33 (m, 2 H) 7.37 (s, 1 H) 7.54 (t, J=8.23 Hz, 1 H) 7.59 (m, 2 H) 7.66 (d, J=6.22 Hz, 1 H) 8.22 (m, 2 H) 9.43 (s, 1 H).

Co. No. 36: (360 MHz, DMSO-d$_6$) δ ppm 2.10 (s, 3 H) 3.25 (s, 3 H) 3.76 (s, 3 H) 3.85 (t, J=5.31 Hz, 2 H) 4.60 (t, J=5.31 Hz, 2 H) 6.90-6.99 (m, 2 H) 7.06 (d, J=1.83 Hz, 1 H) 7.11 (d, J=6.95 Hz, 1 H) 7.20 (d, J=8.42 Hz, 1 H) 7.24 (d, J=8.05 Hz, 1 H) 8.28 (s, 1 H) 8.34 (s, 1 H).

Co. No. 37: (360 MHz, DMSO-d$_6$) δ ppm 0.40-0.53 (m, 2 H) 0.53-0.65 (m, 2 H) 1.31-1.53 (m, 1 H) 2.10 (s, 3 H) 3.76 (s, 3 H) 4.30 (d, J=7.32 Hz, 2 H) 6.92-7.00 (m, 2 H) 7.06 (d, J=1.83 Hz, 1 H) 7.11 (d, J=7.32 Hz, 1 H) 7.20 (d, J=8.42 Hz, 1 H) 7.24 (d, J=8.05 Hz, 1 H) 8.27 (s, 1 H) 8.40 (s, 1 H).

Co. No. 38: (360 MHz, DMSO-d$_6$) δ ppm 0.42-0.50 (m, 2 H) 0.54-0.63 (m, 2 H) 1.29-1.51 (m, 1 H) 2.46 (s, 3 H) 3.87 (s, 3 H) 4.30 (d, J=7.32 Hz, 2 H) 6.92-7.01 (m, 2 H) 7.06-7.11 (m, 2 H) 7.21 (s, 1 H) 7.23 (d, J=8.05 Hz, 1 H) 7.49 (d, J=8.42 Hz, 1 H) 8.39 (s, 1 H).

Co. No. 39: (400 MHz, DMSO-d$_6$) δ ppm 2.10 (s, 3 H) 2.64 (s, 3 H) 3.76 (s, 3 H) 3.84 (s, 3 H) 6.94-7.03 (m, 2 H) 7.07 (d, J=2.02 Hz, 1 H) 7.10-7.18 (m, 2 H) 7.21 (d, J=8.07 Hz, 1 H) 7.24-7.31 (m, 3 H) 7.52 (t, J=8.28 Hz, 1 H) 8.25 (s, 1 H).

Co. No. 40: (360 MHz, DMSO-d$_6$) δ ppm 2.45 (s, 3 H), 2.62 (s, 3 H), 3.86 (s, 3 H), 6.98-7.05 (m, 2 H), 7.09 (d, J=2.2 Hz, 1 H), 7.14 (d, J=6.9 Hz, 1 H), 7.19 (s, 1 H), 7.27 (d, J=8.1 Hz, 1 H), 7.41-7.53 (m, 3 H), 7.71-7.82 (m, 2 H), 8.39 (s, 1 H).

Co. No. 42: (360 MHz, CDCl$_3$) δ ppm 2.52 (s, 3 H) 2.61 (s, 3 H) 3.90 (s, 3 H) 4.02 (s, 3 H) 6.93 (d, J=6.22 Hz, 1 H) 7.04-7.16 (m, 3 H) 7.32 (s, 1 H) 7.38 (dd, J=8.42, 1.83 Hz, 1 H) 7.49 (t, J=8.23 Hz, 1 H) 7.63-7.69 (m, 2 H) 7.79 (d, J=6.22 Hz, 1 H) 7.98 (d, J=1.83 Hz, 1 H).

Co. No. 43: (360 MHz, DMSO-d$_6$) δ ppm 0.38-0.50 (m, 2 H) 0.54-0.65 (m, 2 H) 1.30-1.50 (m, 1 H) 2.53 (s, 3 H) 4.28 (br. s., 2 H) 7.02 (t, J=7.68 Hz, 1 H) 7.11 (d, J=6.95 Hz, 1 H) 7.42 (d, J=8.05 Hz, 1 H) 7.72-7.87 (m, 2 H) 7.87-7.98 (m, 1 H) 8.43 (s, 1 H) 8.47 (s, 1 H) 9.22 (br. s., 1 H).

Co. No. 44: (360 MHz, CDCl$_3$) δ ppm 2.57 (s, 3 H) 5.01 (q, J=8.42 Hz, 2 H) 6.79 (s, 1 H) 7.01-7.11 (m, 2 H) 7.23 (dd, J=7.68, 1.83 Hz, 1 H) 7.43 (s, 1 H) 7.57 (d, J=8.42 Hz, 1 H) 7.71 (dd, J=8.42, 2.56 Hz, 1 H) 8.03 (s, 1 H) 8.61 (d, J=2.56 Hz, 1 H).

Co. No. 46: (360 MHz, CDCl$_3$) δ ppm 2.61 (s, 3 H), 2.62 (s, 3 H), 6.85 (s, 1 H), 6.97-7.07 (m, 1 H), 7.12 (d, J=6.9 Hz, 1 H), 7.19 (d, J=8.1 Hz, 1 H), 7.22-7.32 (m, 2 H), 7.52-7.61 (m, 3 H), 7.71 (dd, J=8.8, 2.9 Hz, 1 H), 7.83 (s, 1 H), 8.64 (d, J=2.6 Hz, 1 H).

Co. No. 48: (360 MHz, CDCl$_3$) δ ppm 1.41 (d, J=6.95 Hz, 6 H) 3.15 (spt, J=6.95 Hz, 1 H) 5.00 (q, J=8.29 Hz, 2 H) 6.82 (s, 1 H) 7.05 (t, J=7.68 Hz, 1 H) 7.10 (d, J=6.95 Hz, 1 H) 7.13

(s, 1 H) 7.17 (d, J=8.05 Hz, 1 H) 7.34 (m, J=8.42 Hz, 2 H) 7.59 (m, J=8.42 Hz, 2 H) 8.01 (s, 1 H).

Co. No. 49: (360 MHz, CDCl$_3$) δ ppm 2.71 (s, 3 H) 3.90 (s, 3 H) 4.22 (s, 3 H) 6.81 (s, 1 H) 6.88-6.96 (m, 2 H) 7.02 (t, J=7.68 Hz, 1 H) 7.13 (d, J=7.68 Hz, 1 H) 7.17 (d, J=8.42 Hz, 1 H) 7.49 (d, J=8.42 Hz, 1 H) 7.86 (s, 1 H) 7.90 (s, 1 H).

Co. No. 50: (360 MHz, CDCl$_3$) δ ppm 2.34 (t, J=2.0 Hz, 3 H), 2.72 (s, 3 H), 3.92 (s, 3 H), 6.90-6.95 (m, 2 H), 6.97 (dd, J=8.2, 2.0 Hz, 1 H), 7.01-7.08 (m, 2 H), 7.16 (d, J=6.9 Hz, 1 H), 7.24 (dd, J=8.4, 0.7 Hz, 1 H), 7.51 (d, J=8.1 Hz, 1 H), 7.82 (td, J=8.5, 6.0 Hz, 1 H), 7.92 (s, 1 H), 8.36 (d, J=2.6 Hz, 1 H).

Co. No. 51: (360 MHz, DMSO-d$_6$) δ ppm 2.43 (s, 3 H) 2.47 (s, 3 H) 3.91 (s, 3 H) 5.46 (q, J=9.03 Hz, 2 H) 6.85 (s, 1 H) 7.15 (dd, J=8.42, 1.83 Hz, 1 H) 7.22 (d, J=1.83 Hz, 1 H) 7.30 (s, 1 H) 7.61 (d, J=8.42 Hz, 1 H) 8.47 (s, 1 H) 9.11 (s, 1 H).

Co. No. 52: (360 MHz, CDCl$_3$) δ ppm 2.31 (d, J=0.73 Hz, 3 H) 5.00 (q, J=8.42 Hz, 2 H) 6.84 (s, 1 H) 6.93 (q, J=1.46 Hz, 1 H) 7.03-7.09 (m, 2 H) 7.13 (dd, J=7.32, 0.73 Hz, 1 H) 7.20 (dd, J=12.62, 2.38 Hz, 1 H) 7.23-7.30 (m, 2 H) 7.66 (t, J=1.46 Hz, 1 H) 8.03 (s, 1 H).

Co. No. 53: (360 MHz, DMSO-d$_6$) δ ppm 2.64 (s, 3 H) 3.84 (s, 3 H) 3.86 (s, 3 H) 6.34 (d, J=1.83 Hz, 1 H) 6.98 (t, J=7.86 Hz, 1 H) 7.06-7.16 (m, 2 H) 7.23-7.29 (m, 3 H) 7.35-7.43 (m, 4 H) 7.45 (d, J=1.83 Hz, 1 H) 7.52 (t, J=8.23 Hz, 1 H).

Co. No. 54: (360 MHz, CDCl$_3$) δ ppm 2.30 (d, J=0.73 Hz, 3 H) 4.07 (s, 3 H) 5.01 (q, J=8.42 Hz, 2 H) 6.60 (d, J=8.05 Hz, 1 H) 6.89 (t, J=1.10 Hz, 1 H) 7.12 (dd, J=8.60, 7.50 Hz, 1 H) 7.22-7.29 (m, 1 H) 7.44 (d, J=8.42 Hz, 1 H) 7.56 (s, 1 H) 7.64 (d, J=1.10 Hz, 1 H) 8.03 (s, 1 H) 8.05 (d, J=7.32 Hz, 1 H).

Co. No. 55: (360 MHz, CDCl$_3$d) δ ppm 2.31 (s, 3 H) 5.06 (q, J=8.05 Hz, 2 H) 6.58 (s, 1 H) 6.94 (s, 1 H) 7.10 (dd, J=8.60, 2.38 Hz, 1 H) 7.19 (dd, J=12.26, 2.38 Hz, 1 H) 7.30 (t, J=8.60 Hz, 1 H) 7.68 (s, 1 H) 8.25 (s, 1 H) 8.33 (s, 1 H) 8.83 (s, 1 H).

Co. No. 56: (360 MHz, CDCl$_3$) δ ppm 1.32 (d, J=6.95 Hz, 6 H) 2.51 (s, 3 H) 2.96-3.13 (m, J=13.79, 6.89, 6.89, 6.89, 6.89 Hz, 1 H) 3.93 (s, 3 H) 4.98 (q, J=8.29 Hz, 2 H) 6.87 (s, 1 H) 7.02-7.14 (m, 3 H) 7.75 (d, J=8.42 Hz, 1 H) 8.15 (s, 1 H) 8.58 (s, 1 H).

Co. No. 57: (360 MHz, DMSO-d$_6$) δ ppm 1.27 (d, J=6.95 Hz, 6 H) 2.16 (s, 3 H) 3.05 (spt, J=6.95 Hz, 1 H) 4.06 (s, 3 H) 5.47 (q, J=9.15 Hz, 2 H) 7.13 (s, 1 H) 7.16 (d, J=8.42 Hz, 1 H) 7.74 (d, J=8.42 Hz, 1 H) 7.77 (d, J=1.10 Hz, 1 H) 8.26 (s, 1 H) 8.57 (s, 1 H) 9.82 (s, 1 H).

Pharmacology

A) Screening of the Compounds of the Invention for γ-Secretase-Modulating Activity A1) Method 1

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67. Briefly, cells were plated in a 96-well plate at about $10^5$ cells/ml one day prior to addition of compounds. Compounds were added to the cells in Ultraculture (Lonza, BE12-725F) supplemented with 1% glutamine (Invitrogen, 25030-024) for 18 hours. The media were assayed by two sandwich ELISAs, for Aβ42 and Aβtotal. Toxicity of the compounds was assayed by WST-1 cell proliferation reagent (Roche, 1 644 807) according to the manufacturer's protocol.

To quantify the amount of Aβ42 in the cell supernatant, commercially available Enzyme-Linked-Immunosorbent-Assay (ELISA) kits were used (Innotest® β-Amyloid$_{(1-42)}$, Innogenetics N.V., Ghent, Belgium). The Aβ42 ELISA was performed essentially according to the manufacturer's protocol. Briefly, the standards (dilutions of synthetic Aβ1-42) were prepared in polypropylene Eppendorf with final concentrations of 8000 down to 3.9 µg/ml (½ dilution step). Samples, standards and blanks (100 µl) were added to the anti-Aβ42-coated plate supplied with the kit (the capture antibody selectively recognizes the C-terminal end of the antigen). The plate was allowed to incubate 3 h at 25° C. in order to allow formation of the antibody-amyloid complex. Following this incubation and subsequent wash steps a selective anti-A13-antibody conjugate (biotinylated 3D6) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of 3,3',5,5'-tetramethylbenzidine (TMB)/peroxide mixture, resulting in the conversion of the substrate into a coloured product. This reaction was stopped by the addition of sulfuric acid (0.9 N) and the colour intensity was measured by means of photometry with an ELISA-reader with a 450 nm filter.

To quantify the amount of Aβtotal in the cell supernatant, samples and standards were added to a 6E10-coated plate. The plate was allowed to incubate overnight at 4° C. in order to allow formation of the antibody-amyloid complex. Following this incubation and subsequent wash steps a selective anti-AB-antibody conjugate (biotinylated 4G8) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of Quanta Blu fluorogenic peroxidase substrate according to the manufacturer's instructions (Pierce Corp., Rockford, Il).

To obtain the values reported in Table 3a, the sigmoidal dose response curves were analysed by computerised curve-fitting, with percent of inhibition plotted against compound concentration. A 4-parameter equation (model 205) in XLfit was used to determine the IC$_{50}$. The top and the bottom of the curve were fixed to 100 and 0, respectively, and the hill slope was fixed to 1. The IC$_{50}$ represents the concentration of a compound that is required for inhibiting a biological effect by 50% (Here, it is the concentration where Aβ peptide level is reduced by 50%).

The IC$_{50}$ values are shown in Table 3a:

| Co. No. | IC$_{50}$ Aβ42 (µM) | IC$_{50}$ Aβtotal (µM) | Co. No. | IC$_{50}$ Aβ42 (µM) | IC$_{50}$ Aβtotal (µM) | Co. No. | IC$_{50}$ Aβ42 (µM) | IC$_{50}$ Aβtotal (µM) |
|---|---|---|---|---|---|---|---|---|
| 1 | 0.046 | >3 | 29 | 0.028 | >1 | 11 | 0.077 | >3 |
| 15 | 0.075 | >3 | 16 | 0.190 | >3 | 32 | 2.131 | >3 |
| 2 | 0.007 | >1 | 30 | 0.127 | >3 | 25 | 1.74 | >150 |
| 19 | 0.126 | >3 | 23 | 1.036 | n.d. | 34 | 0.359 | n.d. |
| 3 | 0.113 | >3 | 14 | 0.029 | n.d. | 37 | 2.658 | >3 |
| 10 | 0.099 | >3 | 20 | 0.067 | >3 | 35 | 0.382 | >3 |
| 40 | 0.186 | >3 | 50 | 0.865 | n.d. | 7 | 0.229 | >3 |
| 4 | 0.055 | >3 | 39 | 0.029 | >3 | 38 | 0.518 | >3 |
| 46 | 0.199 | >3 | 5 | 0.031 | >3 | 8 | 0.180 | >10 |
| 22 | >3 | >3 | 42 | 0.091 | >3 | 44 | 0.513 | >3 |
| 9 | 1.467 | >10 | 13 | 0.283 | >3 | 18 | 0.479 | >3 |
| 31 | 0.126 | >3 | 6 | 0.152 | >3 | 45 | 0.023 | >3 |

A2) Method 2

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Invitrogen (cat no. 10371-029)

containing 5% Serum/Fe supplemented with 1% non-essential amino acids, 1-glutamine 2 mM, Hepes 15 mM, penicillin 50 U/ml (units/ml) en streptomycin 50 µg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 µg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of AB (JRF/AβN/25) was used to react with the donor beads. To quantify the amount of Aβtotal in the cell supernatant, monoclonal antibody specific to the N-terminus of AB (JRF/AβN/25) was coupled to the receptor beads and biotinylated antibody specific to the mid region of Aβ (biotinylated 4G8) was used to react with the donor beads.

To obtain the values reported in Table 3b, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

The IC50 values are shown in Table 3b ('n.d.' means not determined):

| Co. No. | $IC_{50}$ Aβ42 (µM) | $IC_{50}$ Aβtotal (µM) |
|---|---|---|
| 1 | 0.081 | 8.318 |
| 2 | 0.007 | 6.457 |
| 3 | <3 | >3 |
| 4 | 0.022 | 4.786 |
| 5 | 0.018 | 8.128 |
| 6 | 0.162 | 3.981 |
| 7 | 0.055 | >10 |
| 8 | 0.177 | >10 |
| 9 | <3 | >3 |
| 10 | <3 | >3 |
| 11 | <3 | >3 |
| 12 | >3 | n.d. |
| 13 | 0.079 | >10 |
| 14 | 0.020 | 7.079 |
| 15 | 0.014 | 6.607 |
| 16 | 0.054 | 8.511 |
| 17 | >3 | >3 |
| 18 | 0.331 | >10 |
| 19 | 0.123 | 3.020 |
| 20 | 0.059 | 6.026 |
| 21 | >3 | >3 |
| 22 | >3 | >3 |
| 23 | 0.724 | >10 |
| 24 | >3 | >3 |
| 25 | 1.259 | 48.978 |
| 26 | >3 | >3 |
| 27 | >3 | n.d. |
| 28 | >3 | n.d. |
| 29 | 0.015 | >10 |
| 30 | 0.129 | >10 |
| 31 | 0.037 | >10 |
| 32 | >3 | >3 |
| 33 | 0.166 | >10 |
| 34 | 0.479 | >10 |
| 35 | 0.166 | >10 |
| 36 | >3 | n.d. |
| 37 | >3 | >3 |
| 38 | 0.234 | 4.677 |
| 39 | 0.030 | >10 |
| 40 | 0.032 | 5.495 |
| 41 | >3 | >3 |
| 42 | 0.120 | 4.365 |
| 43 | 1.413 | n.d. |
| 44 | 0.363 | >10 |
| 45 | 0.018 | 6.761 |
| 46 | 0.066 | 4.266 |
| 47 | 0.035 | 6.918 |
| 48 | >3 | >3 |
| 49 | >3 | >3 |
| 50 | 0.676 | >10 |
| 51 | 0.234 | 5.248 |
| 52 | 0.339 | >10 |
| 53 | 0.631 | >10 |
| 54 | 0.066 | >10 |
| 55 | 0.603 | >10 |
| 56 | 0.708 | >10 |
| 57 | 0.107 | 1.660 |

B) Demonstration of In Vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K.U.Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (A13) in the brain, eventually resulting in amyloid plaques within the subiculum, hippocampus and cortex. Animals treated with the Aβ42 lowering agent were examined and compared to those untreated or treated with vehicle and brain levels of soluble Aβ42 and total Aβ would be quantitated by standard techniques, for example, using ELISA. Treatment periods varied from hours to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After four hours, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains were resuspended in 10 volumes of 0.4% DEA (diethylamine)/50 mM NaCl pH 10 (for non-transgenic animals) or 0.1% 3-[(3-cholamidopropyl)-dimethyl-ammonio]-1-propanesulfonate (CHAPS) in tris buffered saline (TBS) (for transgenic animals) containing protease inhibitors (Roche-11873580001 or 04693159001) per gram of tissue, e.g. for 0.158 g brain, add 1.58 ml of 0.4% DEA. All samples were sonicated for 30 sec on ice at 20% power output (pulse mode). Homogenates were centrifuged at 221.300×g for 50 min. The resulting high speed supernatants were then transferred to fresh tubes and were optionally further purified before the next step. A portion of the supernatant was neutralized with 10% 0.5 M Tris-HCl and this was used to quantify Aβtotal.

The obtained supernatants were purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 ml/min, so the vacuum pressure was adjusted accordingly throughout the procedure. Columns were preconditioned with 1 ml of 100% MeOH, before equilibration with 1 ml of H$_2$O, Non-neutralized brain lysates were loaded onto the columns. The loaded samples were then washed twice with the first wash performed with 1 ml of 5% MeOH, and the second wash with 1 ml of 30% MeOH. Finally, the Aβ was eluted from the columns and into 100×30 mm glass tubes, with a solution of 90% MeOH with 2% NH$_4$OH. The eluate was then transferred into 1.5 ml tubes and concentrated in a speed-vac concentrator on high heat for about 1.5-2 h at 70° C. The concentrated Aβ was then resuspended in UltraCULTURE General Purpose Serum-Free Medium (Cambrex Corp., Walkersville, Md.) plus Protease Inhibitors added according to the manufacturers recommendation.

To quantify the amount of Aβ42 in the soluble fraction of the brain homogenates, commercially available Enzyme-Linked-Immunosorbent-Assay (ELISA) kits were used (e.g. Innotest® β-Amyloid$_{(1-42)}$, Innogenetics N.V., Ghent, Belgium). The Aβ42 ELISA was performed using the plate provided with the kit only. Briefly, the standards (a dilution of synthetic Aβ1-42) were prepared in 1.5 ml Eppendorf tube in Ultraculture, with final concentrations ranging from 25000 to 1.5 µg/ml. Samples, standards and blanks (60 µl) were added to the anti-Aβ42-coated plate (the capture antibody selectively recognizes the C-terminal end of the antigen). The plate was allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) was added and incubated for a minimum of 1 h in order to allow formation of the antibody-Amyloid-antibody-complex. After incubation and appropriate wash steps, a Streptavidine-Peroxidase-Conjugate was added, followed 50 min later by an addition of Quanta Blu fluorogenic peroxidase substrate according to the manufacturer's instructions (Pierce Corp., Rockford, Il). A kinetic reading was performed every 5 min for 30 min (excitation 320 nm/emission 420 nm). To quantify the amount of Aβtotal in the soluble fraction of the brain homogenates, samples and standards were added to JRF/rAβ/2-coated plate. The plate was allowed to incubate overnight at 4° C. in order to allow formation of the antibody-amyloid complex. The ELISA was then performed as for Aβ42 detection.

In this model at least 20% Aβ42 lowering compared to untreated animals would be advantageous.

The results are shown in table 4:

| Co. No. | Aβ42 (% Ctrl) _Mean | Aβtotal (% Ctrl) _Mean | Co. No. | Aβ42 (% Ctrl) _Mean | Aβtotal (% Ctrl) _Mean | Co. No. | Aβ42 (% Ctrl) _Mean | Aβtotal (% Ctrl) _Mean |
|---|---|---|---|---|---|---|---|---|
| 1 | 94 | 108 | | | | | | |
| 15 | 69 | 94 | | | | | | |
| 2 | 59 | 90 | | | | | | |
| | | | 42 | 104 | 100 | | | |
| | | | | | | 38 | 123 | 106 |
| 29 | 96 | 98 | 6 | 79 | 95 | | | |
| | | | | | | 54 | 72 | 109 |

C) Effect on the Notch-Processing Activity of the γ-Secretase-Complex

Notch Cell-free Assay

The Notch transmembrane domain is cleaved by gamma secretase to release Notch Intracellular C-terminal Domain (NICD). Notch is a signaling protein which plays a crucial role in developmental processes, and thus compounds are preferred which do not show an effect on the Notch-processing activity of the γ-secretase-complex.

To monitor the effect of compounds on NICD production, a recombinant Notch substrate (N99) was prepared. The Notch substrate, comprised of mouse Notch fragment (V1711-E1809), an N-terminal methionine and a C-terminal FLAG sequence (DYDDDDK), was expressed in *E. coli* and purified on a column containing an anti-FLAG M2 affinity matrix.

A typical Notch cell-free assay consisted of 0.3-0.5 nM Notch substrate, an enriched preparation of gamma secretase and 1 nM of a test compound (compound 45 of the present invention). Controls included a gamma secretase inhibitor (GSI), such as (2S)-N-[2-(3,5-difluorophenyl)acetyl]-L-alanyl-2-phenyl-glycine 1,1-dimethylethyl ester (DAPT) or (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide (Semagacestat), and DMSO, the final concentration of DMSO being 1%. Recombinant Notch substrate was pre-treated with 17 μM DTT (1,4-dithiothreitol) and 0.02% SDS (Sodium Dodecyl Sulfate) and heated at 65° C. for 10 min. The mixture of substrate, gamma secretase and compound/DMSO was incubated at 37° C. for 6 to 22 hours (h). Six-hour incubation was sufficient to produce the maximal amount of NICD and the cleaved product remained stable for an additional 16 h. Reaction products were processed for SDS PAGE (Sodium Dodecyl Sulfate—Poly Acrylamide Gel Electrophoresis) and western blotting. Blots were probed with an anti-Flag M2 antibody, followed by LI-COR infrared secondary antibody, and analyzed with the Odyssey Infrared Imaging System (LI-COR® Biosciences).

In the cell-free Notch assay, no test compounds (compound 45 of the present invention) inhibited the cleavage of C99 by γ-secretase, whereas the production of NICD was blocked by the control GSI (DAPT or Semagacestat). Thus it was demonstrated that compound 45 of the present invention did not show an effect on the Notch-processing activity of the γ-secretase-complex (production of NICD).

Composition Examples

"Active ingredient" (a.i.) as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
| Stearyl alcohol | 3 g |

-continued

| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

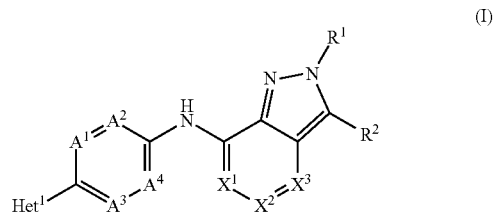

(I)

or a stereoisomeric form thereof, wherein $R^1$ is $C_{1-6}$alkyl optionally substituted with one or more substituents each independently selected from the group consisting of halo, $C_{1-4}$alkyloxy, cyclo$C_{3-7}$alkyl, tetrahydropyranyl, tetrahydrofuranyl and phenyl; cyclo$C_{3-7}$ alkyl; tetrahydropyranyl; tetrahydrofuranyl; 1,3-benzodioxolyl; or phenyl;

wherein each phenyl independently is optionally substituted with one or more substituents each independently selected from the group consisting of halo, cyano, $C_{1-4}$alkyl optionally substituted with one or more halo substituents, and $C_{1-4}$alkyloxy optionally substituted with one or more halo substituents;

$R^2$ is hydrogen; cyano; or $C_{1-4}$alkyl optionally substituted with one or more substituents each independently selected from the group consisting of $C_{1-4}$alkyloxy, halo and $NR^3R^4$;

$X^1$ is CH or N;

$X^2$ is $CR^5$ or N;

$R^5$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

$X^3$ is $CR^6$ or N;

$R^6$ is hydrogen; halo; cyano; $C_{1-4}$alkyloxy; or $C_{1-4}$alkyl optionally substituted with one or more substituents each independently selected from the group consisting of halo, $C_{1-4}$alkyloxy and $NR^3R^4$;

wherein each $R^3$ is independently hydrogen; $C_{1-4}$alkyl; or $C_{1-4}$acyl;

wherein each $R^4$ is independently hydrogen; $C_{1-4}$alkyl; or $C_{1-4}$acyl;

provided that no more than two of $X^1$, $X^2$ and $X^3$ are N;

$A^1$ is $CR^7$ or N; wherein $R^7$ is hydrogen, halo or $C_{1-4}$alkyloxy;

$A^2$, $A^3$ and $A^4$ each independently are CH or N; provided that no more than two of $A^1$, $A^2$, $A^3$ and $A^4$ are N;

Het$^1$ is a 5-membered aromatic heterocycle, having formula (a-1), (a-2), (a-3) or (a-4)

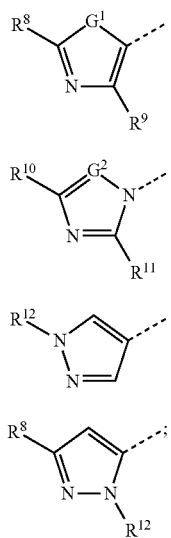

R$^8$ is hydrogen or C$_{1-4}$alkyl;
R$^9$ is hydrogen or C$_{1-4}$alkyl;
R$^{10}$ is hydrogen or C$_{1-4}$alkyl;
R$^{11}$ is hydrogen or C$_{1-4}$alkyl;
R$^{12}$ is C$_{1-4}$alkyl;
G$^1$ is O or S;
G$^2$ is CH or N;
or a pharmaceutically acceptable addition salt or a solvate thereof.

2. The compound according to claim 1 or a stereoisomeric form thereof, wherein
R$^1$ is C$_{1-6}$alkyl optionally substituted with one or more substituents each independently selected from the group consisting of halo, C$_{1-4}$alkyloxy, cycloC$_{3-7}$alkyl and phenyl;
cycloC$_{3-7}$alkyl; tetrahydropyranyl; 1,3-benzodioxolyl; or phenyl;
wherein each phenyl independently is substituted with one or more substituents each independently selected from the group consisting of halo, C$_{1-4}$alkyl and C$_{1-4}$alkyloxy;
R$^2$ is hydrogen; cyano; or C$_{1-4}$alkyl optionally substituted with one or more NH$_2$ substituents;
X$^2$ is CR$^5$ or N; in particular X$^2$ is CR$^5$;
R$^5$ is hydrogen; halo; cyano; or C$_{1-4}$alkyl optionally substituted with one or more NH$_2$ substituents;
X$^3$ is CH or N;
A$^2$ is CH or N, and A$^3$ and A$^4$ are CH;
Het$^1$ is a 5-membered aromatic heterocycle, having formula (a-1), (a-2), (a-3) or (a-4);
R$^{10}$ is C$_{1-4}$alkyl;
R$^{11}$ is hydrogen;
R$^8$ is hydrogen;
R$^{12}$ is C$_{1-4}$alkyl;
or a pharmaceutically acceptable addition salt or a solvate thereof.

3. The compound according to claim 1 or a stereoisomeric form thereof, wherein
R$^1$ is phenyl substituted with one C$_{1-4}$alkyloxy substituent; or R$^1$ is C$_{1-6}$alkyl substituted with one or more halo substituents;
R$^2$ is hydrogen;
X$^1$, X$^2$ and X$^3$ are CH;
A$^1$ is CR$^7$; wherein R$^7$ is C$_{1-4}$alkyloxy; A$^2$, A$^3$ and A$^4$ are CH;
Het$^1$ has formula (a-1) or (a-2);
G$^1$ is O; G$^2$ is CH;
R$^8$ is C$_{1-4}$alkyl;
R$^{10}$ is C$_{1-4}$alkyl;
R$^9$ is hydrogen;
or a pharmaceutically acceptable addition salt or a solvate thereof.

4. The compound according to claim 1, or a stereoisomeric form thereof, wherein
R$^1$ is phenyl substituted with one or more substituents each independently selected from the group consisting of C$_{1-4}$alkyl and C$_{1-4}$alkyloxy;
or a pharmaceutically acceptable addition salt or a solvate thereof.

5. The compound according to claim 1, or a stereoisomeric form thereof, wherein
R$^1$ is C$_{1-6}$alkyl optionally substituted with one or more halo substituents;
or a pharmaceutically acceptable addition salt or a solvate thereof.

6. The compound according to claim 1 wherein the compound is selected from the group comprising N-[3-methoxy-4-(2-methyl-5-oxazolyl)phenyl]-2-(2,2,2-trifluoroethyl)-2H-indazol-7-amine, and N-[3-methoxy-4-(4-methyl-1H-imidazol-1-yl)phenyl]-2-(3-methoxyphenyl)-3-methyl-2H-indazol-7-amine,
including any stereochemically isomeric form thereof,
and the pharmaceutically acceptable addition salts and the solvates thereof.

7. A pharmaceutical composition comprising a pharmaceutically acceptable carrier and, as active ingredient, a therapeutically effective amount of a compound as defined in any one of claims 1 to 6.

8. A pharmaceutical composition comprising a compound as defined in any one of claims 1 to 6 and a pharmaceutically acceptable carrier.

9. A method for the treatment of a disease or condition selected from Alzheimer's disease, traumatic brain injury, mild cognitive impairment, senility, dementia, dementia with Lewy bodies, cerebral amyloid angiopathy, multi-infarct dementia, Down's syndrome, dementia associated with Parkinson's disease and dementia associated with beta-amyloid comprising administering to a subject a compound as defined in any one of claims 1 to 6.

10. The method according to claim 9 wherein the disease is Alzheimer's disease.

* * * * *